United States Patent
Kang et al.

(10) Patent No.: US 10,087,248 B2
(45) Date of Patent: Oct. 2, 2018

(54) ANTI-TNF-α/CXCL10 DOUBLE-TARGETING ANTIBODY AND USE THEREOF

(71) Applicant: METABOLIC ENGINEERING LABORATORIES CO., LTD., Seoul (KR)

(72) Inventors: Heun-Soo Kang, Gwacheon-si (KR); So-Hyun Park, Namyangju-si (KR); Yeong Wook Song, Seoul (KR); Ki Chul Shin, Seoul (KR); Eun Young Lee, Seoul (KR); Eun Bong Lee, Seoul (KR); Young Woo Park, Daejeon (KR); Bum-Chan Park, Daejeon (KR); Dong Hee Lee, Daejeon (KR); Dong Jin Kim, Daejeon (KR); Seon Ha Yun, Daejeon (KR); Ke Se Lee, Daejeon (KR); Hyun Ju Lee, Daejeon (KR); Kyung Jin Kim, Daejeon (KR); Hee Chan Kim, Daejeon (KR); Seok Ho Yoo, Daejeon (KR); Myeoung Hee Jang, Daejeon (KR); Seil Jang, Daejeon (KR)

(73) Assignee: METABOLIC ENGINEERING LABORATORIES CO., LTD., Seoul (KR)

( * ) Notice: Subject to any disclaimer, the term of this patent is extended or adjusted under 35 U.S.C. 154(b) by 0 days.

(21) Appl. No.: 14/893,071

(22) PCT Filed: May 22, 2014

(86) PCT No.: PCT/KR2014/004579
§ 371 (c)(1),
(2) Date: Nov. 22, 2015

(87) PCT Pub. No.: WO2014/189306
PCT Pub. Date: Nov. 27, 2014

(65) Prior Publication Data
US 2016/0108118 A1    Apr. 21, 2016

(30) Foreign Application Priority Data

May 22, 2013    (KR) .................. 10-2013-0057475
May 22, 2013    (KR) .................. 10-2013-0057762

(51) Int. Cl.
| | | |
|---|---|---|
| *A61K 39/395* | (2006.01) | |
| *C07K 16/24* | (2006.01) | |
| *C12N 5/10* | (2006.01) | |
| *C07K 16/46* | (2006.01) | |
| *A61K 39/00* | (2006.01) | |

(52) U.S. Cl.
CPC ............ *C07K 16/241* (2013.01); *C07K 16/24* (2013.01); *C07K 16/46* (2013.01); *A61K 2039/505* (2013.01); *A61K 2039/545* (2013.01); *C07K 2317/31* (2013.01); *C07K 2317/565* (2013.01); *C07K 2317/622* (2013.01); *C07K 2317/64* (2013.01); *C07K 2317/76* (2013.01); *C07K 2317/92* (2013.01)

(58) Field of Classification Search
None
See application file for complete search history.

(56) References Cited

U.S. PATENT DOCUMENTS 8,258,268 B2    9/2012    Wu et al.
2005/0053600 A1    10/2005    Lane
2007/0071675 A1    3/2007    Wu et al.

FOREIGN PATENT DOCUMENTS

KR    10-2010-0097720 A    9/2010
KR    10-2012-0125611 A    11/2012
KR    1020130121601 A    11/2013
(Continued)

OTHER PUBLICATIONS

Agusti et al. Evaluation of COPD Longitudinally to Identify Predictive Surrogate Endpoints (ECLIPSE) Investigators. Persistent systemic inflammation is associated with poor clinical outcomes in COPD: a novel phenotype. PLoS One. 2012;7(5):e37483. Epub May 18, 2012.*

(Continued)

*Primary Examiner* — Christine J Saoud
(74) *Attorney, Agent, or Firm* — Don D. Cha; Hamilton DeSanctis & Cha, LLP

(57) ABSTRACT

The present invention relates to a TNF-α (tumor necrosis factor-alpha)/CXCL-10 (C-X-C motif chemokine 10) double targeting antibody based on the IgG format. Specifically, it was verified that an antibody, in which scFv having a heavy chain variable domain and a light chain variable domain of the CXCL10 specific antibody links to the C-terminus of the heavy chain constant domain of the TNF-α specific antibody, is a bispecific antibody that effectively binds to both TNF-α and CXCL10, and thus the antibody can be useful as a double targeting antibody capable of identifying TNF-α/CXCL10. A composition of the present invention comprises a TNF-α/CXCL-10 double targeting antibody which effectively binds to both TNF-α and CXCL10. The double targeting antibody of the present invention has excellent TNF-α inhibitory activity and osteoclast differentiation inhibitory activity compared with the TNF-α or CXCL10 single targeting antibody. The composition of the present invention can be used in preventing or treating immunological disease.

13 Claims, 61 Drawing Sheets
Specification includes a Sequence Listing.

(56) References Cited

FOREIGN PATENT DOCUMENTS

WO          2005023201 A2    3/2005
WO          2013/055958 A1   4/2013

OTHER PUBLICATIONS

Jordana et al. Immune-inflammatory functions of fibroblasts. Eur Respir J. Dec. 1994;7(12):2212-22.*
Wiendl et al. Therapeutic approaches in multiple sclerosis: lessons from failed and interrupted treatment trials. BioDrugs. 2002;16(3):183-200.*
Zuvich et al. Genetics and pathogenesis of multiple sclerosis. Semin Immunol. Dec. 2009;21(6):328-33.*
Eun Young Lee, et al., "Potential role and mechanism of IFN-gamma inducible protein-10 on receptor activator of nuclear factor kappa-B ligand (RANKL) expression in rheumatoid arthritis", Arthritis Research & Therapy, 2011.
Palanisamy Kanakaraj et al. "Simultaneous targeting of TNF and Ang2 with a novel bispecific antibody enhances efficacy in an in vivo model of arthritis". 2012. Landes Bioscience vol. 4, Issue 5. pp. 600-613.
Severine Fagete et al. "Specificity tuning of antibody fragments to neutralize two human chemokines with a single agent". 2009. Landes Bioscience vol. 1, Issue 3. pp. 288-296.
Beck, A et al., "Strategies and challenges for the next generation of therapeutic antibodies," in Nat Rev Immunology, 2010, vol. 10, pp. 345-352.
Bostrom, Jenny et al., "Variants of the Antibody Herceptin That Interact with HER2 and VEGF at the Antigen Binding Site," Science, Mar. 20, 2009, vol. 323. pp. 1610-1614.
Gregory Gregoriadis Judith Senior and Andre Trouet eds., "Targeting of Antitumour and Antiprotozoal Drugs by Covalent Linkage to Protein Carriers," Targeting of Drugs, 1982, pp. 19-30, Plenum Press, New York and London.
Moolton, F. L.; Schreiber, B. M.; and Zajdel, S. H., "Antibodies Conjugated to Potent Cytotoxins as Specific Antitumor Agents," Immunological Rev., 1982, vol. 62. pp. 47-73.
Arnon et al., "Antibodies as Carriers for Oncostatic Materials," in Recent Results in Cancer Res. 1980, v. 75. pp. 236-245, Mathe, G. and Muggia eds., Springer-Verlag, Berlin Heidelberg New York.

* cited by examiner

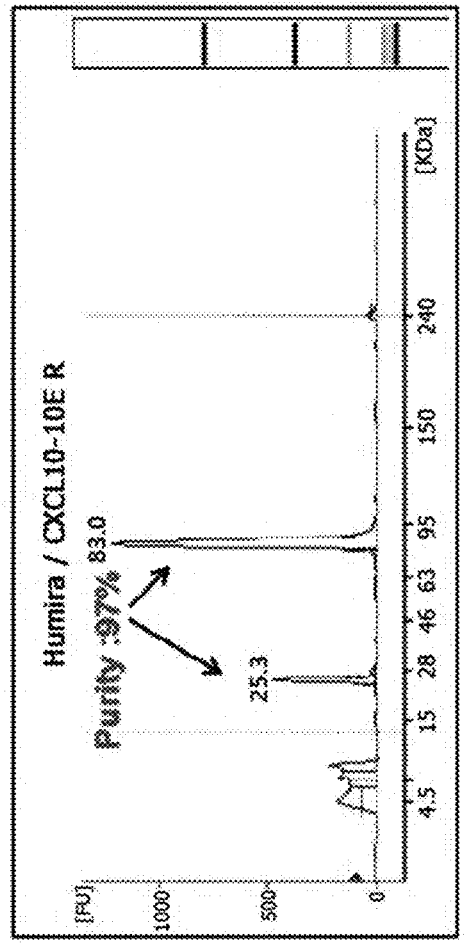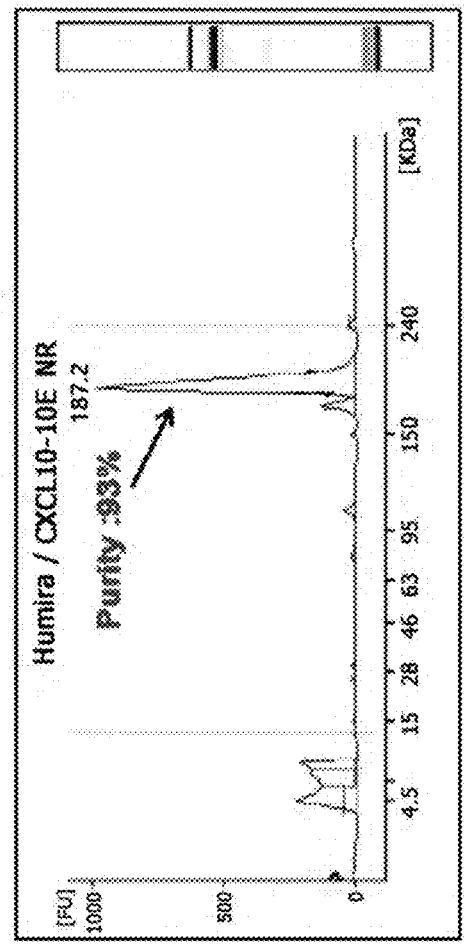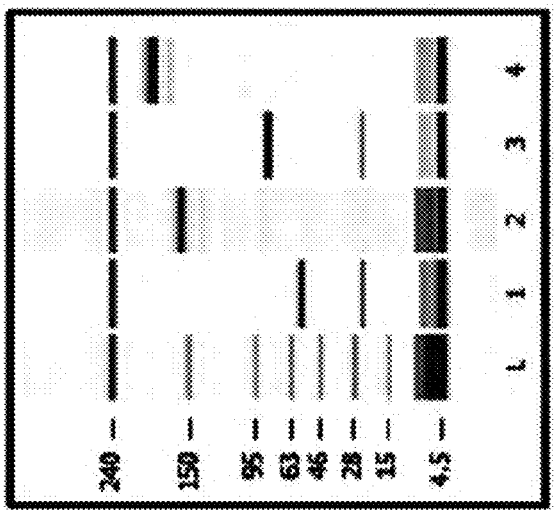
FIG. 6

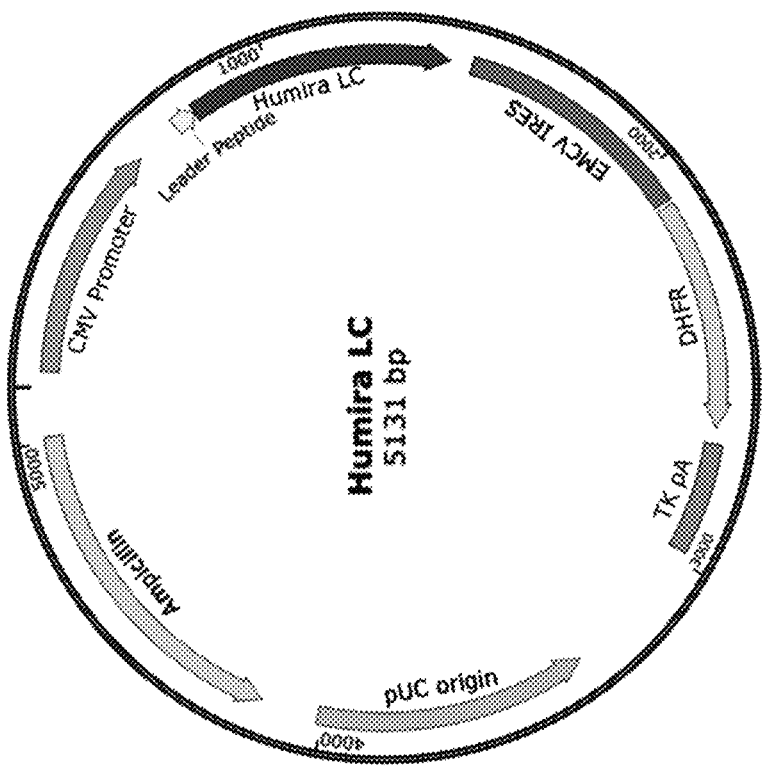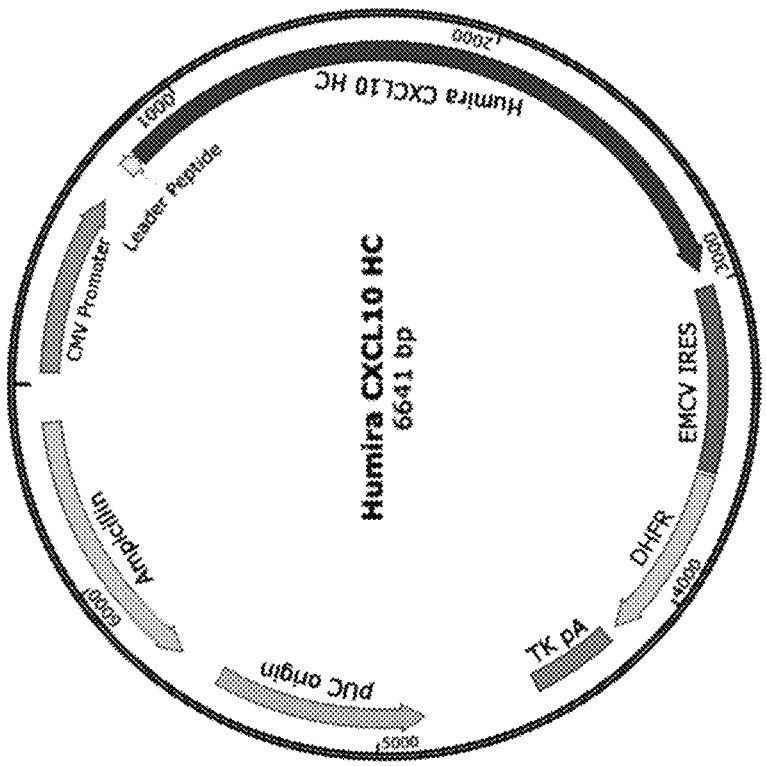
FIG. 9

1 : DNA : Lipofectamine = 1:1
2 : DNA : Lipofectamine = 1:1.5
3 : DNA : Lipofectamine = 1:2

FIG. 13

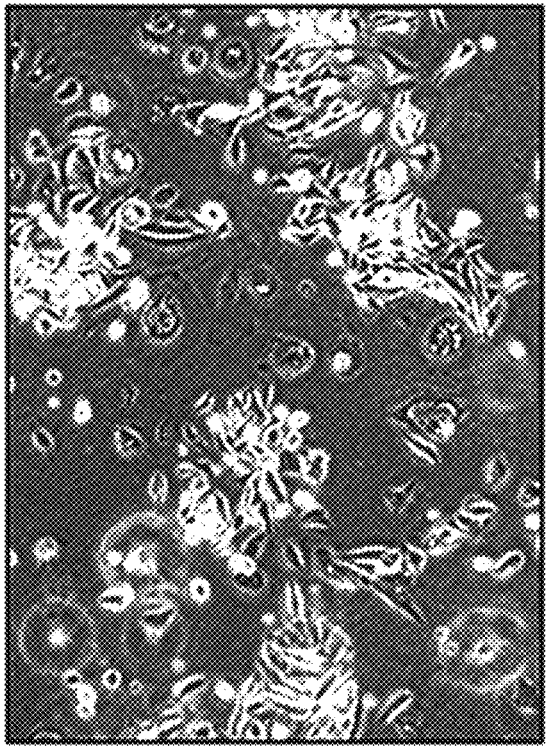
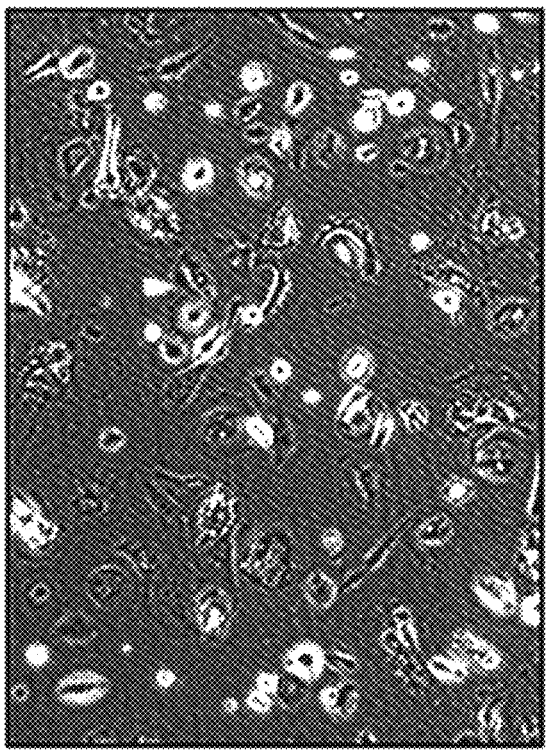
FIG. 16

<Heavy chain>
1    EVQLV ESGGG LVQPG RSLRL SCAAS GFTFD DYAMH WVRQA PGKGL EWVSA
51   ITWNS GHIDY ADSVE GRFTI SRDNA KNSLY LQMNS LRAED TAVYY CARVS
101  YLSTA SSLDY WGQGT LVTVS SASTK GPSVF PLAPS SKSTS GGTAA LGCLV
151  KDYFP EPVTV SWNSG ALTSG VHTFP AVLQS SGLYS LSSVV TVPSS SLGTQ
201  TYICN VNHKP SNTKV DKRVE PKSCD KTHTC PPCPA PELLG GPSVF LFPPK
251  PKDTL MISRT PEVTC VVVDV SHEDP EVKFN WYVDG VEVHN AKTKP REEQY
301  NSTYR VVSVL TVLHQ DWLNG KEYKC KVSNK ALPAP IEKTI SKAKG QPREP
351  QVYTL PPSRD ELTKN QVSLT CLVKG FYPSD IAVEW ESNGQ PENNY KTTPP
401  VLDSD GSFFL YSKLT VDKSR WQQGN VFSCS VMHEA LHNHY TQKSL SLSPG
451  KQVQL VQSGG GVVQP GRSLR LSCAA SGFTF NSYGM HWVRQ APGKG LEWVA
501  VISYD GNSKY YADSV KGRFT ISRDN SKNTL YLQMN SLRAE DTAVY YCARD
551  SGSYL DWYFD LWGRG TLVTV SSGLG GLGGG GSGGG GSGGS SGVGS QFVLT
601  QPPSV SGAPG QRVTI SCTGS RSNIG AGHDV HWYQQ LPGTA PKLLI YGNNN
651  RPSGV PDRFS GSKSG TSASL AITGL QAEDE ADYYC QSYDS RLGVV FGGGT
701  KLTVL <Light chain>
1    DIQMT QSPSS LSASV GDRVT ITCRA SQGIR NYLAW YQQKP GKAPK LLIYA
51   ASTLQ SGVPS RFSGS GSGTD FTLTI SSLQP EDVAT YYCQR YNRAP YTFGQ
101  GTKVE IKRSV AAPSV FIFPP SDEQL KSGTA SVVCL LNNFY PREAK VQWKV
151  DNALQ SGNSQ ESVTE QDSKD STYSL SSTLT LSKAD YEKHK VYACE VTHQG
201  LSSPV TKSFN RGEC Matched amino acid : 902/919
Sequence coverage : 98.1%

FIGURE 21

SEQUENCE LISTING

```
<160> NUMBER OF SEQ ID NOS: 60

<210> SEQ ID NO 1
<211> LENGTH: 5
<212> TYPE: PRT
<213> ORGANISM: Artificial
<220> FEATURE:
<223> OTHER INFORMATION: TNF_VH_CDR1

<400> SEQUENCE: 1

Asp Tyr Ala Met His
1               5

<210> SEQ ID NO 2
<211> LENGTH: 17
<212> TYPE: PRT
<213> ORGANISM: Artificial
<220> FEATURE:
<223> OTHER INFORMATION: TNF_VH_CDR2

<400> SEQUENCE: 2

Ala Ile Thr Trp Asn Ser Gly His Ile Asp Tyr Ala Asp Ser Val Glu
1               5                   10                  15

Gly

<210> SEQ ID NO 3
<211> LENGTH: 13
<212> TYPE: PRT
<213> ORGANISM: Artificial
<220> FEATURE:
<223> OTHER INFORMATION: TNF_VH_CDR3

<400> SEQUENCE: 3

Ala Lys Val Ser Tyr Leu Ser Thr Ala Ser Ser Leu Asp
1               5                   10

<210> SEQ ID NO 4
<211> LENGTH: 121
<212> TYPE: PRT
```

```
<213> ORGANISM: Artificial
<220> FEATURE:
<223> OTHER INFORMATION: TNF_VH_total

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 5
<211> LENGTH: 11
<212> TYPE: PRT
<213> ORGANISM: Artificial
<220> FEATURE:
<223> OTHER INFORMATION: TNF_VL_CDR1

<400> SEQUENCE: 5

Arg Ala Ser Gln Gly Ile Arg Asn Tyr Leu Ala
1               5                   10

<210> SEQ ID NO 6
<211> LENGTH: 7
<212> TYPE: PRT
<213> ORGANISM: Artificial
<220> FEATURE:
<223> OTHER INFORMATION: TNF_VL_CDR2

<400> SEQUENCE: 6

Ala Ala Ser Thr Leu Gln Ser
1               5

<210> SEQ ID NO 7
<211> LENGTH: 7
<212> TYPE: PRT
<213> ORGANISM: Artificial
<220> FEATURE:
<223> OTHER INFORMATION: TNF_VL_CDR3

<400> SEQUENCE: 7

Gln Arg Tyr Asn Arg Ala Pro
1               5

<210> SEQ ID NO 8
<211> LENGTH: 107
<212> TYPE: PRT
<213> ORGANISM: Artificial
<220> FEATURE:
<223> OTHER INFORMATION: TNF_VL_total

<400> SEQUENCE: 8
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 9
<211> LENGTH: 5
<212> TYPE: PRT
<213> ORGANISM: Artificial
<220> FEATURE:
<223> OTHER INFORMATION: 10E_VH_CDR1

<400> SEQUENCE: 9

```
Ser Tyr Gly Met His
1               5
```

<210> SEQ ID NO 10
<211> LENGTH: 20
<212> TYPE: PRT
<213> ORGANISM: Artificial
<220> FEATURE:
<223> OTHER INFORMATION: 10E_VH_CDR2

<400> SEQUENCE: 10

```
Trp Val Ala Val Ile Ser Tyr Asp Gly Asn Ser Lys Tyr Tyr Ala Asp
1               5                   10                  15

Ser Val Lys Gly
            20
```

<210> SEQ ID NO 11
<211> LENGTH: 12
<212> TYPE: PRT
<213> ORGANISM: Artificial
<220> FEATURE:
<223> OTHER INFORMATION: 10E_VH_CDR3

<400> SEQUENCE: 11

```
Asp Ser Gly Ser Tyr Leu Asp Trp Tyr Phe Asp Leu
1               5                   10
```

<210> SEQ ID NO 12
<211> LENGTH: 121
<212> TYPE: PRT
<213> ORGANISM: Artificial
<220> FEATURE:
<223> OTHER INFORMATION: 10E_VH_total

<400> SEQUENCE: 12

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Asn Ser Tyr
            20                  25                  30
```

```
Gly Met His Trp Val Arg Gln Ala Pro Gly Lys Gly Pro Glu Trp Val
        35                  40                  45
Ala Val Ile Ser Tyr Asp Gly Asn Ser Lys Tyr Tyr Ala Asp Ser Val
    50                  55                  60
Lys Gly Arg Phe Thr Ile Ser Arg Asp Asn Ser Lys Thr Thr Leu Tyr
65                  70                  75                  80
Leu Gln Met Asn Ser Leu Arg Ser Glu Asp Thr Ala Val Tyr Tyr Cys
                85                  90                  95
Ala Arg Asp Ser Gly Ser Tyr Leu Asp Trp Tyr Phe Asp Leu Trp Gly
            100                 105                 110
Arg Gly Thr Leu Val Thr Val Ser Ser
        115                 120

<210> SEQ ID NO 13
<211> LENGTH: 15
<212> TYPE: PRT
<213> ORGANISM: Artificial
<220> FEATURE:
<223> OTHER INFORMATION: 10E_VL_CDR1

<400> SEQUENCE: 13

Cys Thr Gly Ser Arg Ser Asn Phe Gly Ala Gly His Asp Val His
1               5                   10                  15

<210> SEQ ID NO 14
<211> LENGTH: 7
<212> TYPE: PRT
<213> ORGANISM: Artificial
<220> FEATURE:
<223> OTHER INFORMATION: 10E_VL_CDR2

<400> SEQUENCE: 14

Gly Asn Asn Asn Arg Pro Ser
1               5

<210> SEQ ID NO 15
<211> LENGTH: 10
<212> TYPE: PRT
<213> ORGANISM: Artificial
<220> FEATURE:
<223> OTHER INFORMATION: 10E_VL_CDR3

<400> SEQUENCE: 15

Gln Ser Tyr Asp Ser Arg Leu Gly Val Val
1               5                   10

<210> SEQ ID NO 16
<211> LENGTH: 106
<212> TYPE: PRT
<213> ORGANISM: Artificial
<220> FEATURE:
<223> OTHER INFORMATION: 10E_VL_total

<400> SEQUENCE: 16

Gln Pro Pro Ser Val Ser Gly Ala Pro Gly Gln Arg Val Thr Ile Ser
1               5                   10                  15

Cys Thr Gly Ser Arg Ser Asn Phe Gly Ala Gly His Asp Val His Trp
            20                  25                  30

Tyr Gln Gln Leu Pro Gly Thr Ala Pro Lys Leu Leu Ile Tyr Gly Asn
        35                  40                  45

Asn Asn Arg Pro Ser Gly Val Pro Asp Arg Phe Ser Gly Ser Lys Ser
    50                  55                  60
```

Gly Thr Ser Ala Ser Leu Ala Ile Thr Gly Leu Gln Ala Glu Asp Glu
65                  70                  75                  80

Ala Asp Tyr Tyr Cys Gln Ser Tyr Asp Ser Arg Leu Gly Val Val Phe
                85                  90                  95

Gly Gly Gly Thr Lys Leu Thr Val Leu Gly
            100                 105

<210> SEQ ID NO 17
<211> LENGTH: 5
<212> TYPE: DNA
<213> ORGANISM: Artificial
<220> FEATURE:
<223> OTHER INFORMATION: 10D_VH_CDR1

<400> SEQUENCE: 17 sygmh                                                                         5

<210> SEQ ID NO 18
<211> LENGTH: 20
<212> TYPE: PRT
<213> ORGANISM: Artificial
<220> FEATURE:
<223> OTHER INFORMATION: 10D_VH_CDR2

<400> SEQUENCE: 18

Trp Val Ala Val Ile Ser Tyr Asp Gly Ser Asn Lys Tyr Tyr Ala Asp
1               5                   10                  15

Ser Val Lys Gly
            20

<210> SEQ ID NO 19
<211> LENGTH: 8
<212> TYPE: PRT
<213> ORGANISM: Artificial
<220> FEATURE:
<223> OTHER INFORMATION: 10D_VH_CDR3

<400> SEQUENCE: 19

Asp Lys Arg Ala Ala Phe Asp Ile
1               5

<210> SEQ ID NO 20
<211> LENGTH: 117
<212> TYPE: PRT
<213> ORGANISM: Artificial
<220> FEATURE:
<223> OTHER INFORMATION: 10D_VH_total

<400> SEQUENCE: 20

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Asp Lys Arg Ala Ala Phe Asp Ile Trp Gly Gln Gly Lys Met

Val Thr Val Ser Ser
        115

<210> SEQ ID NO 21
<211> LENGTH: 5
<212> TYPE: PRT
<213> ORGANISM: Artificial
<220> FEATURE:
<223> OTHER INFORMATION: 12D_VH_CDR1

<400> SEQUENCE: 21

Arg Tyr Gly Met His
1               5

<210> SEQ ID NO 22
<211> LENGTH: 20
<212> TYPE: PRT
<213> ORGANISM: Artificial
<220> FEATURE:
<223> OTHER INFORMATION: 12D_VH_CDR2

<400> SEQUENCE: 22

Trp Val Ala Leu Ile Ser Tyr Asp Gly Ser Ser Glu Tyr Tyr Ala Asp
1               5                   10                  15

Ser Val Lys Gly
            20

<210> SEQ ID NO 23
<211> LENGTH: 9
<212> TYPE: PRT
<213> ORGANISM: Artificial
<220> FEATURE:
<223> OTHER INFORMATION: 12D_VH_CDR3

<400> SEQUENCE: 23

Asp Gly Leu Ala Ala Lys Leu Gly His
1               5

<210> SEQ ID NO 24
<211> LENGTH: 118
<212> TYPE: PRT
<213> ORGANISM: Artificial
<220> FEATURE:
<223> OTHER INFORMATION: 12D_VH_total

<400> SEQUENCE: 24

Gln Val Gln Leu Val Gln Ser Gly Gly Gly Val Val Gln Pro Gly Arg
1               5                   10                  15

Ser Leu Arg Leu Ser Cys Val Ala Ser Ala Phe Thr Phe Ser Arg Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Ser Ser Glu Tyr Tyr Ala Asp Ser Val
    50                  55                  60

Lys Gly Arg Phe Asn Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Gly Leu Ala Ala Lys Leu Gly His Trp Gly Gln Gly Thr
            100                 105                 110

Leu Val Thr Val Ser Ser

```
<210> SEQ ID NO 25
<211> LENGTH: 5
<212> TYPE: PRT
<213> ORGANISM: Artificial
<220> FEATURE:
<223> OTHER INFORMATION: 9E_VH_CDR1

<400> SEQUENCE: 25

Ser Tyr Gly Met His
1               5

<210> SEQ ID NO 26
<211> LENGTH: 20
<212> TYPE: PRT
<213> ORGANISM: Artificial
<220> FEATURE:
<223> OTHER INFORMATION: 9E_VH_CDR2

<400> SEQUENCE: 26

Trp Val Ala Val Ile Ser Tyr Asp Gly Asn Asn Lys Tyr Tyr Val Asp
1               5                   10                  15

Ser Val Lys Gly
            20

<210> SEQ ID NO 27
<211> LENGTH: 12
<212> TYPE: PRT
<213> ORGANISM: Artificial
<220> FEATURE:
<223> OTHER INFORMATION: 9E_VH_CDR3

<400> SEQUENCE: 27

Asp Ser Gly Ser Tyr Leu Asp Trp Tyr Phe Asp Leu
1               5                   10

<210> SEQ ID NO 28
<211> LENGTH: 121
<212> TYPE: PRT
<213> ORGANISM: Artificial
<220> FEATURE:
<223> OTHER INFORMATION: 9E_VH_total

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Asp Ser Gly Ser Tyr Leu Asp Trp Tyr Phe Asp Leu Trp Gly
            100                 105                 110

Arg Gly Thr Leu Val Thr Val Ser Ser
        115                 120
```

```
<210> SEQ ID NO 29
<211> LENGTH: 12
<212> TYPE: PRT
<213> ORGANISM: Artificial
<220> FEATURE:
<223> OTHER INFORMATION: 10D_VL_CDR1

<400> SEQUENCE: 29

Cys Ser Gly Asp Asn Leu Arg Thr Lys Tyr Val Ser
1               5                   10

<210> SEQ ID NO 30
<211> LENGTH: 7
<212> TYPE: PRT
<213> ORGANISM: Artificial
<220> FEATURE:
<223> OTHER INFORMATION: 10D_VL_CDR2

<400> SEQUENCE: 30

Gln Asp Thr Arg Arg Pro Ser
1               5

<210> SEQ ID NO 31
<211> LENGTH: 11
<212> TYPE: PRT
<213> ORGANISM: Artificial
<220> FEATURE:
<223> OTHER INFORMATION: 10D_VL_CDR3

<400> SEQUENCE: 31

Met Thr Trp Asp Val Asp Thr Thr Ser Met Ile
1               5                   10

<210> SEQ ID NO 32
<211> LENGTH: 104
<212> TYPE: PRT
<213> ORGANISM: Artificial
<220> FEATURE:
<223> OTHER INFORMATION: 10D_VL_total

<400> SEQUENCE: 32

Gln Ala Pro Ser Leu Ser Val Ser Pro Gly Gln Thr Ala Asn Ile Ile
1               5                   10                  15

Cys Ser Gly Asp Asn Leu Arg Thr Lys Tyr Val Ser Trp Tyr Gln Gln
            20                  25                  30

Lys Pro Gly Gln Ser Pro Leu Leu Val Ile Tyr Gln Asp Thr Arg Arg
        35                  40                  45

Pro Ser Gly Ile Pro Ala Arg Phe Ser Gly Ser Asn Ser Gly Asn Thr
    50                  55                  60

Ala Thr Leu Thr Ile Ser Gly Thr Gln Thr Glu Arg Glu Ser Thr Tyr
65                  70                  75                  80

Tyr Cys Met Thr Trp Asp Val Asp Thr Thr Ser Met Ile Phe Gly Gly
                85                  90                  95

Gly Thr Lys Leu Thr Val Leu Gly
            100

<210> SEQ ID NO 33
<211> LENGTH: 12
<212> TYPE: PRT
<213> ORGANISM: Artificial
<220> FEATURE:
<223> OTHER INFORMATION: 12D_VL_CDR1

<400> SEQUENCE: 33
```

```
Cys Ser Gly Asp Asn Leu Arg Thr Lys Tyr Val Ser
1               5                   10
```

<210> SEQ ID NO 34
<211> LENGTH: 7
<212> TYPE: PRT
<213> ORGANISM: Artificial
<220> FEATURE:
<223> OTHER INFORMATION: 12D_VL_CDR2

<400> SEQUENCE: 34

```
Gln Asp Thr Arg Arg Pro Ser
1               5
```

<210> SEQ ID NO 35
<211> LENGTH: 11
<212> TYPE: PRT
<213> ORGANISM: Artificial
<220> FEATURE:
<223> OTHER INFORMATION: 12D_VL_CDR3

<400> SEQUENCE: 35

```
Met Thr Trp Asp Val Asp Thr Thr Ser Met Ile
1               5                   10
```

<210> SEQ ID NO 36
<211> LENGTH: 104
<212> TYPE: PRT
<213> ORGANISM: Artificial
<220> FEATURE:
<223> OTHER INFORMATION: 12D_VL_total

<400> SEQUENCE: 36

```
Gln Ala Pro Ser Leu Ser Val Ser Pro Gly Gln Thr Ala Asn Ile Ile
1               5                   10                  15

Cys Ser Gly Asp Asn Leu Arg Thr Lys Tyr Val Ser Trp Tyr Gln Gln
                20                  25                  30

Lys Pro Gly Gln Ser Pro Leu Leu Val Ile Tyr Gln Asp Thr Arg Arg
            35                  40                  45

Pro Ser Gly Ile Pro Ala Arg Phe Ser Gly Ser Asn Ser Gly Asn Thr
    50                  55                  60

Ala Thr Leu Thr Ile Ser Gly Thr Gln Thr Glu Arg Glu Ser Thr Tyr
65                  70                  75                  80

Tyr Cys Met Thr Trp Asp Val Asp Thr Thr Ser Met Ile Phe Gly Gly
                85                  90                  95

Gly Thr Lys Leu Thr Val Leu Gly
            100
```

<210> SEQ ID NO 37
<211> LENGTH: 12
<212> TYPE: PRT
<213> ORGANISM: Artificial
<220> FEATURE:
<223> OTHER INFORMATION: 9E_VL_CDR1

<400> SEQUENCE: 37

```
Cys Gly Gly Gly Asn Ile Gly Asp Lys Ser Val His
1               5                   10
```

<210> SEQ ID NO 38
<211> LENGTH: 7
<212> TYPE: PRT
<213> ORGANISM: Artificial
<220> FEATURE:

<223> OTHER INFORMATION: 9E_VL_CDR2

<400> SEQUENCE: 38

Tyr Asp Ser Asp Arg Pro Ser
1               5

<210> SEQ ID NO 39
<211> LENGTH: 11
<212> TYPE: PRT
<213> ORGANISM: Artificial
<220> FEATURE:
<223> OTHER INFORMATION: 9E_VL_CDR3

<400> SEQUENCE: 39

Gln Val Trp Asp Ser Ser Asp Arg Pro Val
1               5                   10

<210> SEQ ID NO 40
<211> LENGTH: 104
<212> TYPE: PRT
<213> ORGANISM: Artificial
<220> FEATURE:
<223> OTHER INFORMATION: 9E_VL_total

<400> SEQUENCE: 40

Gln Pro Pro Ser Val Ser Val Ala Pro Gly Lys Thr Ala Arg Ile Ala
1               5                   10                  15

Cys Gly Gly Gly Asn Ile Gly Asp Lys Ser Val His Trp Tyr Gln Gln
            20                  25                  30

Lys Pro Gly Gln Ala Pro Val Leu Val Ile Phe Tyr Asp Ser Asp Arg
        35                  40                  45

Pro Ser Gly Ile Pro Lys Arg Leu Ser Gly Ser Asn Ser Gly Asn Thr
    50                  55                  60

Ala Thr Leu Thr Ile Ser Arg Val Glu Ala Gly Asp Glu Gly Asp Tyr
65                  70                  75                  80

Tyr Cys Gln Val Trp Asp Ser Ser Asp Arg Pro Val Phe Gly Gly
                85                  90                  95

Gly Thr Lys Leu Thr Val Leu Gly
            100

<210> SEQ ID NO 41
<211> LENGTH: 23
<212> TYPE: DNA
<213> ORGANISM: Artificial
<220> FEATURE:
<223> OTHER INFORMATION: pelB5

<400> SEQUENCE: 41
ctagataacg agggcaaatc atg                                        23

<210> SEQ ID NO 42
<211> LENGTH: 19
<212> TYPE: DNA
<213> ORGANISM: Artificial
<220> FEATURE:
<223> OTHER INFORMATION: cla3

<400> SEQUENCE: 42
cgtcaccaat gaaaccatc                                             19

<210> SEQ ID NO 43
<211> LENGTH: 20
<212> TYPE: DNA

<213> ORGANISM: Artificial
<220> FEATURE:
<223> OTHER INFORMATION: 10D_VH_F

<400> SEQUENCE: 43
caggtgcagc tggtgcagtc                                              20

<210> SEQ ID NO 44
<211> LENGTH: 14
<212> TYPE: DNA
<213> ORGANISM: Artificial
<220> FEATURE:
<223> OTHER INFORMATION: 10D_VH_R

<400> SEQUENCE: 44
tgaggagacg gtga                                                    14

<210> SEQ ID NO 45
<211> LENGTH: 20
<212> TYPE: DNA
<213> ORGANISM: Artificial
<220> FEATURE:
<223> OTHER INFORMATION: 10D_VL_F

<400> SEQUENCE: 45
tcctatgagc tgacacaggc                                              20

<210> SEQ ID NO 46
<211> LENGTH: 21
<212> TYPE: DNA
<213> ORGANISM: Artificial
<220> FEATURE:
<223> OTHER INFORMATION: 10D_VL_R

<400> SEQUENCE: 46
taggacggtc agcttggtcc c                                            21

<210> SEQ ID NO 47
<211> LENGTH: 20
<212> TYPE: DNA
<213> ORGANISM: Artificial
<220> FEATURE:
<223> OTHER INFORMATION: 12D_VH_F

<400> SEQUENCE: 47
caggtgcagc tggtgcagtc                                              20

<210> SEQ ID NO 48
<211> LENGTH: 14
<212> TYPE: DNA
<213> ORGANISM: Artificial
<220> FEATURE:
<223> OTHER INFORMATION: 12D_VH_R

<400> SEQUENCE: 48
tgaggagacg gtga                                                    14

<210> SEQ ID NO 49
<211> LENGTH: 20
<212> TYPE: DNA
<213> ORGANISM: Artificial
<220> FEATURE:
<223> OTHER INFORMATION: 12D_VL_F

<400> SEQUENCE: 49
tcctatgagc tgacacaggc                                              20

<210> SEQ ID NO 50
<211> LENGTH: 21
<212> TYPE: DNA
<213> ORGANISM: Artificial
<220> FEATURE:
<223> OTHER INFORMATION: 12D_VL_R

<400> SEQUENCE: 50
taggacggtc agcttggtcc c                                              21

<210> SEQ ID NO 51
<211> LENGTH: 20
<212> TYPE: DNA
<213> ORGANISM: Artificial
<220> FEATURE:
<223> OTHER INFORMATION: 10E_VH_F

<400> SEQUENCE: 51
caggtgcagc tggtgcagtc                                                20

<210> SEQ ID NO 52
<211> LENGTH: 14
<212> TYPE: DNA
<213> ORGANISM: Artificial
<220> FEATURE:
<223> OTHER INFORMATION: 10E_VH_R

<400> SEQUENCE: 52
tgaggagacg gtga                                                      14

<210> SEQ ID NO 53
<211> LENGTH: 20
<212> TYPE: DNA
<213> ORGANISM: Artificial
<220> FEATURE:
<223> OTHER INFORMATION: 10E_VL_F

<400> SEQUENCE: 53
cagttcgtgc tgactcagcc                                                20

<210> SEQ ID NO 54
<211> LENGTH: 21
<212> TYPE: DNA
<213> ORGANISM: Artificial
<220> FEATURE:
<223> OTHER INFORMATION: 10E_VL_R

<400> SEQUENCE: 54
taggacggtc agcttggtcc c                                              21

<210> SEQ ID NO 55
<211> LENGTH: 20
<212> TYPE: DNA
<213> ORGANISM: Artificial
<220> FEATURE:
<223> OTHER INFORMATION: 9E_VH_F

<400> SEQUENCE: 55
caggtgcagc tggtggagtc                                                20

<210> SEQ ID NO 56
<211> LENGTH: 14
<212> TYPE: DNA
<213> ORGANISM: Artificial
<220> FEATURE:

<223> OTHER INFORMATION: 9E_VH_R

<400> SEQUENCE: 56
tgaggagacg gtga                                                         14

<210> SEQ ID NO 57
<211> LENGTH: 20
<212> TYPE: DNA
<213> ORGANISM: Artificial
<220> FEATURE:
<223> OTHER INFORMATION: 9E_VL_F

<400> SEQUENCE: 57
aattttatgc tgactcagcc                                                   20

<210> SEQ ID NO 58
<211> LENGTH: 21
<212> TYPE: DNA
<213> ORGANISM: Artificial
<220> FEATURE:
<223> OTHER INFORMATION: 9E_VL_R

<400> SEQUENCE: 58
taggacggtc agcttggtcc c                                                 21

<210> SEQ ID NO 59
<211> LENGTH: 705
<212> TYPE: PRT
<213> ORGANISM: Artificial
<220> FEATURE:
<223> OTHER INFORMATION: HuE10-101 Heavy Chain

<400> SEQUENCE: 59

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

-continued

```
Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gln Val Gln Leu Val Gln Ser Gly Gly Val Val Gln
    450                 455                 460

Pro Gly Arg Ser Leu Arg Leu Ser Cys Ala Ala Ser Gly Phe Thr Phe
465                 470                 475                 480

Asn Ser Tyr Gly Met His Trp Val Arg Gln Ala Pro Gly Lys Gly Pro
                485                 490                 495

Glu Trp Val Ala Val Ile Ser Tyr Asp Gly Asn Ser Lys Tyr Tyr Ala
            500                 505                 510

Asp Ser Val Lys Gly Arg Phe Thr Ile Ser Arg Asp Asn Ser Lys Thr
        515                 520                 525

Thr Leu Tyr Leu Gln Met Asn Ser Leu Arg Ser Glu Asp Thr Ala Val
    530                 535                 540

Tyr Tyr Cys Ala Arg Asp Ser Gly Ser Tyr Leu Asp Trp Tyr Phe Asp
545                 550                 555                 560

Leu Trp Gly Arg Gly Thr Leu Val Thr Val Ser Ser Gly Leu Gly Gly
                565                 570                 575

Leu Gly Gly Gly Gly Ser Gly Gly Gly Gly Ser Gly Gly Ser Ser Gly
            580                 585                 590

Val Gly Ser Gln Phe Val Leu Thr Gln Pro Pro Ser Val Ser Gly Ala
        595                 600                 605

Pro Gly Gln Arg Val Thr Ile Ser Cys Thr Gly Ser Arg Ser Asn Phe
    610                 615                 620

Gly Ala Gly His Asp Val His Trp Tyr Gln Gln Leu Pro Gly Thr Ala
```

```
                625                 630                 635                 640
Pro Lys Leu Leu Ile Tyr Gly Asn Asn Arg Pro Ser Gly Val Pro
                    645                 650                 655

Asp Arg Phe Ser Gly Ser Lys Ser Gly Thr Ser Ala Ser Leu Ala Ile
                660                 665                 670

Thr Gly Leu Gln Ala Glu Asp Glu Ala Asp Tyr Tyr Cys Gln Ser Tyr
                675                 680                 685

Asp Ser Arg Leu Gly Val Val Phe Gly Gly Thr Lys Leu Thr Val
        690                 695                 700

Leu
705

<210> SEQ ID NO 60
<211> LENGTH: 214
<212> TYPE: PRT
<213> ORGANISM: Artificial
<220> FEATURE:
<223> OTHER INFORMATION: HuE10-101 Light Chain

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-TNF-α/CXCL10 DOUBLE-TARGETING ANTIBODY AND USE THEREOF

TECHNICAL FIELD

The present invention relates to a TNF-α/CXCL-10 double-targeting antibody specifically binding to tumor necrosis factor-alpha (TNF-α) and C-X-C motif chemokine 10 (CXCL10) and a use thereof.

RELATED PATENT APPLICATIONS

This application claims priority to and the benefit of Korean Patent Application Nos. 10-2013-0057475 and 10-2013-0057762, filed on May 22, 2013, the disclosure of which is incorporated herein by reference in its entirety.

BACKGROUND ART

Generally, an antibody is formed by forming a heterodimer by linking a heavy chain polypeptide having a high molecular weight with a light chain polypeptide having a low molecular weight by a disulfide bond, and forming a tetramer by linking two heterodimers again by a disulfide bond. The heavy chain-forming polypeptide consists of four domains, which include a variable domain, a constant domain 1, a constant domain 2 and a constant domain 3 from an N-terminus, and the light chain-forming polypeptide consists of two domains, which include a variable domain and a constant domain from an N-terminus. Among these, a conjugate of a variable domain of the heavy chain and a variable domain of the light chain binds to one antigen.

A reaction between an antigen, which is a chemical marker for labeling cells, and an antibody against the antigen indicates high specificity. An antigen site interacting with the antibody is called an antigen determinant or epitope, and the antigen determinant specifically binds to an antigen-binding site, which is a variable domain, of the antibody. Therefore, since the antigen-binding site may bind to only one antigen determinant, each of numerous antibodies may provide a unique immunity with respect to the antigen having a specific determinant.

Antibodies have a high stability in blood and a low antigenicity, and thus have attracted attention as a medicine. Among these antibodies, there is a bispecific antibody capable of recognizing two types of antigens. The bispecific antibody may be divided into two main types. The first-type bispecific antibody is modified by a recombinant DNA technique to have antigen-binding sites capable of binding to two different antigens, and in this case, one of the binding sites may be specific to any antigen, and the other one may be an antibody specific to another antigen and simultaneously binding to two antigens (Beck A et. al., Nat Rev immunology 10; 345-352, 2010). The second-type bispecific antibody is a very recently developed normal antibody, which has one antigen-binding site and a binding capability to two different antigens, and called a two-in-one antibody (Bostrom, J et. al., Science 323, 1610-1614, 2009). Since such a two-in-one antibody has one antigen-binding site, it can bind to one antigen at a time, rather than binding to two antigens, but has a capability of binding to two different antigens. The two-in-one antibody has a form of typical antibody that has been successfully developed, and thus is very favorable for development.

Since such a bispecific antibody may act by binding to a specific toxic cell and a target cell, it has a high target specificity.

As there is the growing understanding of the pathological physiology of rheumatoid arthritis, the concept of targeted therapy for regulating a disease by blocking the highly targeted material by anti-rheumatic drugs newly developed from the late 1990's came to the fore. As a result, as biological drugs formed by designing a material found as a target for a specific disease and capable of blocking the target are developed and used, they bring a great change in the treatment of rheumatoid arthritis. These drugs representatively include interleukin-6 antagonists (tocilizumab), CTLA4Ig (abatacept), and a B cell depleting agent (rituximab), as well as TNF-α inhibitors (etanercept, infliximab, adalimumab, etc.) and a recombinant interleukin-1 receptor antagonist such as anakinra, and are actually used clinically or in tests.

Studies on TNF-α (tumor necrosis factor-alpha) which targets tumors and sepsis in patients have already begun about 100 years ago. TNF-α is produced by macrophages, immune cells including B and T lymphocytes, non-immune cells, and various tumor cells, and plays important roles in a normal physiological inflammatory response and acquired and innate immunities. However, in an inflammatory disease such as rheumatoid arthritis, when TNF-α is inappropriately overproduced, various cells of an immune system are activated to induce a cytotoxic effect, and reactions such as inflammation, the destruction of tissues and organ damage appear. The main biological actions of the TNF-α are regulation of growth, differentiation, and metabolism in various types of cells; stimulation of lipolysis, inhibition of an activity of a lipoprotein lipase present in adipocytes, and induction of cachexia by stimulating hepatic lipogenesis; and induction of apoptosis. TNF-α is present in either a free form or a cell membrane-bound form. These two forms of TNF-α very strongly induce the inflammatory response of cells, and stimulate a disease state in a tissue. The cell membrane-bound TNF-α exhibits cytotoxic and inflammatory effects through cell-to-cell contact, and is detached from a cell membrane by a TNF-α convertase (TACE) and exists out of the cell. This TNF-α binds to one of the two receptors in blood, such as a TNF type I receptor (p55) or TNF type II receptor (p75), thereby exhibiting a biological activity. Clinically, overproduced TNF-α produces an inflammatory mediator stimulating macrophages in a rheumatoid arthritis patient and amplifying an inflammatory response, and expresses an attached molecule on a vascular endothelial cell to allow more inflammatory cells to be collected at an inflammatory site, and allows a fibroblast to produce a protease, resulting in damage to cartilages, bones and ligaments and thus exacerbating a disease.

Since, a TNF-α inhibitor was first approved by Food and Drug Administration (FDA) under the name of etanercept as a therapeutic agent for rheumatoid arthritis in November, 1998 and has been commercially available, infliximab and adalimumab have become commercially available, and new drugs improved in effects and side effects of the conventional drugs are being developed. Therapeutic reactions of the TNF-α inhibitor, the activity of a disease, structural damage corresponding thereto, the influence on the quality of life by a disease, and symptoms and signs generated by a disease vary depending on a patient. Also, sensitivity to a drug, a developing pattern of the effect or a side effect may also vary. Components, specific action mechanisms, pharmacological mechanisms and biopharmaceutical properties vary between various types of TNF-α inhibitors. For an animal test for demonstrating the efficacy of the TNF-α inhibitor, human TNF-α transgenic (Tg) mice were used, and in Tg197 mice, arthritis similar to rheumatoid arthritis occurs at the age of 4 to 5 weeks old, and from 9 to 10 weeks old, a remarkable limitation in the range of motion of the lower leg joint was observed.

CXCL10 (C-X-C motif chemokine 10), also known as interferon-gamma-inducible protein 10 (IP-10), is a 10 kDa chemokine induced by interferon gamma (IFN-γ). It is known that the CXCL10 has a chemotactic activity, and is involved in mitogenic activity. It is noted that the CXCL10 is secreted by various cells including endothelial cells, monocytes, fibroblasts and keratinocytes in response to IFN-γ, and present in epidermal macrophages and endothelial cells when delayed-type hypersensitivity (DTH) occurs on human skin. Also, the above-described reaction may be originally induced by IFN-γ, but also by IFN-α in dendritic cells and in central nervous system neurons due to stimuli such as IFN-γ, a virus and a lipopolysaccharide.

Receptors of CXCL10 are identified as seven transmembrane receptors, that is, CXCR3s. CXCR3s are expressed in activated T lymphocytes and monocytes, synoviocytes, endothelial cells, NK cells and eosinophils. It is known that two different ligands of CXCR3, that is, a monocyte/macrophage activating, IFN-γ-inducible protein (MIG) and an IFN-γ-inducible T cell alpha chemoattractant 1 (I-TAC), also bind to CXCR3. The binding of CXCL10 to CXCR3 mediates calcium mobilization and chemostasis in activated T cells and activated NK cells. In the thymus, CXCL10 is identified as a chemoattractant with respect to TCRαβ+ CD8+ T cells, TCRγδ+ T cells and NK-type cells.

CXCL10 or its receptor CXCR3 is identified in a variety of different inflammatory and autoimmune diseases including multiple sclerosis, rheumatoid arthritis, ulcerative colitis, hepatitis, inflammatory myositis, spinal cord injury, systemic lupus erythematosus, graft rejection and Sjogren's syndrome. However, it has not been specifically known how such CXCL10 acts in an inflammatory response or immune response, except chemotaxis, in those diseases, and how important the CXCL10 is as a target for treatment.

In treatment of an autoimmune disease in which various inflammation mediators contribute to the causes of the disease, when several targets are neutralized with one type of antibody, other than a monoclonal antibody targeting a single antigen, the antibody may act as a more effective therapeutic agent. Attempts to recognize two targets with an antibody formed by combining two different antibodies have been already reported by several researchers. According to the recent study (Bostrom et al. Science 2009), an antibody simultaneously neutralizing vascular endothelial cell growth factors (VEGF) in an antibody library in which light chain CDRs of an antibody recognizing a human epidermal growth factor receptor 2 (HER2) are mutated was successfully screened. The antibody is a bispecific antibody recognizing both of mediators contributing to the causes of a disease, and particularly, has the same structure as normal IgG and a pharmacodynamic characteristic that can be expected, and is formed in both types of a bi- or monovalent antibody.

Throughout the specification, various publications and patents are referenced and citations are provided in parentheses. The disclosures of the cited publications and patents in their entities are hereby incorporated by references into the specification to fully describe the present invention and the state of the art to which the invention pertains.

DISCLOSURE

Technical Problem

In the attempt to develop a bispecific antibody specifically binding to TNF-α and CXCL10, the inventors constructed an antibody in which a single-chain variable fragment (scFv) having a heavy chain variable domain and a light chain variable domain of a CXCL10-specific antibody binds to a C-terminus of a heavy chain constant domain of a TNF-α-specific antibody, confirmed that the antibody bispecifically binds to both of TNF-α and CXCL10, and experimentally determined that the TNF-α/CXCL-10 double-targeting antibody specifically binding to TNF-α and CXCL10 has TNF-α inhibitory activity and osteoclast differentiation inhibitory activity, resulting in completion of the present invention.

Therefore, the present invention is directed to providing a TNF-α/CXCL-10 double-targeting antibody specifically binding to TNF-α (tumor necrosis factor-alpha) and CXCL10(C-X-C motif chemokine 10).

The present invention is also directed to providing a pharmaceutical composition for preventing or treating an immune disease, which includes the TNF-α/CXCL-10 double-targeting antibody.

Other objectives and advantages of the present invention will be more clearly understood by the following detailed description and claims of the present invention.

Technical Solution

According to an aspect of the present invention, the present invention provides a TNF-α/CXCL-10 double-targeting antibody, which includes a first antigen-binding site specifically binding to TNF-α (tumor necrosis factor-alpha), and a second antigen-binding site specifically binding to CXCL10 (C-X-C motif chemokine 10), where the first antigen-binding site includes a heavy chain variable domain (VH) including a heavy chain complementarity determining region (HCDR) 1 having the amino acids of SEQ ID NO: 1, HCDR2 having the amino acids of SEQ ID NO: 2, and HCDR3 having the amino acids of SEQ ID NO: 3, and a light chain variable domain (VL) including a light chain complementarity-determining region (LCDR) 1 having the amino acids of SEQ ID NO: 5, LCDR2 having the amino acids of SEQ ID NO: 6, and LCDR3 having the amino acids of SEQ ID NO: 7; and the second antigen-binding site includes a heavy chain variable domain (VH) including the HCDR1 having an amino acids selected from the group consisting of SEQ ID NOs: 9, 17, 21 and 25, HCDR2 having an amino acids selected from the group consisting of SEQ ID NOs: 10, 18, 22 and 26 and HCDR3 having an amino acids selected from the group consisting of SEQ ID NOs: 11, 9, 23 and 27, and a light chain variable domain (VL) including the LCDR1 having an amino acids selected from the group consisting of SEQ ID NOs: 13, 29, 33 and 37, LCDR2 having an amino acids selected from the group consisting of SEQ ID NOs: 14, 30, 34 and 38, and LCDR3 having an amino acids selected from the group consisting of SEQ ID NOs: 15, 31, 35 and 39.

In the attempt to develop a bispecific antibody specifically binding to TNF-α and CXCL10, the inventors constructed an antibody in which a scFv having a heavy chain variable domain and a light chain variable domain of a CXCL10-specific antibody binds to a C-terminus of a heavy chain constant domain of a TNF-α-specific antibody, confirmed that the antibody bispecifically binds to both of TNF-α and CXCL10, and experimentally determined that the TNF-α/CXCL-10 double-targeting antibody specifically binding to TNF-α and CXCL10 has TNF-α inhibitory activity and osteoclast differentiation inhibitory activity.

The antibody used herein is a TNF-α/CXCL-10 double-targeting antibody specifically binding to TNF-α and CXCL10.

According to an exemplary embodiment of the present invention, the antibody of the present invention is a human antibody.

The term "human antibody" used herein is an antibody in which sequences of variable and constant domains of a heavy chain and a light chain are derived from a human, and as described in the following examples, the inventors constructed a TNF-α/CXCL-10-double targeting human antibody using genetic recombination and cell engineering techniques. The human antibody has more advantages than non-human and chimeric antibodies: an effector of the human antibody more favorably interacts with another region of a human immune system (for example, target cells are more effectively destroyed due to complement-dependent cytotoxicity (CDC) or antibody-dependent cell cytotoxicity (ADCC), and since the human immune system does not recognize the human antibody as a foreign substance, an immune response to such an antibody entering a living body occurs less than that to entire foreign non-human antibodies or partially foreign chimeric antibodies. Also, it was reported that an injected non-human antibody has a significantly shorter half-life than the human antibody in a human circulatory system. Contrarily, since the human antibody entering the living body has substantially the same half-life as a naturally-occurring human antibody, it is more advantageous because the dose and the frequency of dosing may be reduced.

The term "variable domain" used herein refers to a region of an antibody molecule that functions to specifically bind to an antigen and shows many variations in a sequence, and in the variable domain, CDR1, CDR2 and CDR3 are present. Between the CDRs, a framework region (FR) is present to support a CDR ring.

The term "complementarity-determining region (CDR)" used herein is a ring-shape region involved in recognition of an antigen, and depending on the sequence of the region, the specificity of the antibody with respect to the antigen is determined.

The term "panning" used herein refers to a process for selecting only a phage which displays a scFv having a property of binding with target molecules (an antigen, an enzyme, a cell-surface receptor, etc.) on a surface from a phage library displaying a scFv on a coat of the phage.

Specifically, the double-targeting antibody may include, but is not limited to, a first antigen-binding site specifically binding to TNF-α, and a second antigen-binding site specifically binding to CXCL10, where the first antigen-binding site includes a heavy chain variable domain (VH) including HCDR (Heavy chain complementarity determining region) 1 consisting of the amino acid sequence of SEQ ID NO: 1, HCDR2 consisting of the amino acid sequence of SEQ ID NO: 2, and HCDR3 consisting of the amino acid sequence of SEQ ID NO: 3, and a light chain variable domain (VL) including LCDR (Light chain complementarity determining region) 1 consisting of the amino acid sequence of SEQ ID NO: 5, LCDR2 consisting of the amino acid sequence of SEQ ID NO: 6, and LCDR3 consisting of the amino acid sequence of SEQ ID NO: 7, and the second antigen-binding site includes a heavy chain variable domain (VH) including the HCDR1 having amino acids selected from the group consisting of SEQ ID NOs: 9, 17, 21 and 25, the HCDR2 having amino acids selected from the group consisting of SEQ ID NOs: 10, 18, 22 and 26, and the HCDR3 having amino acids selected from the group consisting of SEQ ID NO: 11, 19, 23 and 27, and a light chain or its fragment, which includes a light chain variable domain (VL) including the LCDR1 having amino acids selected from the group consisting of SEQ ID NOs: 13, 29, 33 and 37, LCDR2 having amino acids selected from the group consisting of SEQ ID NOs: 14, 30, 34 and 38, and LCDR3 having amino acids selected from the group consisting of SEQ ID NOs: 15, 31, 35 and 39.

For example, the second antigen-binding site may include a heavy chain variable domain (VH) including the HCDR1 having the amino acids of SEQ ID NO: 9, HCDR2 having the amino acids of SEQ ID NO: 10, and HCDR3 having the amino acids of SEQ ID NO: 11, and a light chain variable domain (VL) including the LCDR1 having the amino acids of SEQ ID NO: 13, CDR2 having the amino acids of SEQ ID NO: 14, and LCDR3 having the amino acids of SEQ ID NO: 15.

The second antigen-binding site may include a heavy chain variable domain (VH) including the HCDR1 having the amino acids of SEQ ID NO: 17, HCDR2 having the amino acids of SEQ ID NO: 18, and HCDR3 having the amino acids of SEQ ID NO: 19, and a light chain variable domain (VL) including the LCDR1 having the amino acids of SEQ ID NO: 29, LCDR2 having the amino acids of SEQ ID NO: 30, and LCDR3 having the amino acids of SEQ ID NO: 31.

The second antigen-binding site may include a heavy chain variable domain (VH) including the HCDR1 having the amino acids of SEQ ID NO: 21, HCDR2 having the amino acids of SEQ ID NO: 22, and HCDR3 having the amino acids of SEQ ID NO: 23, and a light chain variable domain (VL) including the LCDR1 having the amino acids of SEQ ID NO: 33, LCDR2 having the amino acids of SEQ ID NO: 34, and LCDR3 having the amino acids of SEQ ID NO: 35.

The second antigen-binding site may include a heavy chain variable domain (VH) including the HCDR1 having the amino acids of SEQ ID NO: 25, HCDR2 having the amino acids of SEQ ID NO: 26, and HCDR3 having the amino acids of SEQ ID NO: 27, and a light chain variable domain (VL) including the LCDR1 having the amino acids of SEQ ID NO: 37, LCDR2 having the amino acids of SEQ ID NO: 38, and LCDR3 having the amino acids of SEQ ID NO: 39.

The first antigen-binding site of the TNF-α/CXCL-10 double-targeting antibody may include, but is not limited to, the heavy chain variable domain (VH) having the amino acids of SEQ ID NO: 4 and the light chain variable domain (VL) having the amino acids of SEQ ID NO: 8.

The second antigen-binding site of the TNF-α/CXCL-10 double-targeting antibody may include, but is not limited to, a heavy chain variable domain (VH) having the amino acids set forth in SEQ ID NOs: 12, 20, 24 and 28, and a light chain variable domain (VL) having the amino acids set forth in SEQ ID NO: 16, 32, 36 and 40.

The TNF-α/CXCL-10 double-targeting antibody includes a heavy chain and a light chain of a first full-length antibody specifically binding to TNF-α; and a variable fragment of a second antibody specifically binding to CXCL10, and C-termini of the heavy chain constant domains of the first full-length antibody is linked to the variable fragment of the second antibody. Specifically, the TNF-α/CXCL-10 double-targeting antibody includes heavy and light chains of a first full-length antibody specifically binding to TNF-α; and a fragment including a heavy chain domain and a light chain domain of the second antibody specifically binding to CXCL10, and the fragment of the second antibody is linked to a C-terminus of a heavy chain constant domain of the first full-length antibody (refer to FIG. 1).

A fragment of the TNF-α/CXCL-10 double-targeting antibody may be a scFv, but the present invention is not limited thereto.

In the TNF-α/CXCL-10 double-targeting antibody, the antibody-antibody or antibody-fragment linkage may be formed by a linker, but the present invention is not limited thereto.

In an exemplary embodiment of the present invention, the inventors prepared a CXCL10 antigen protein by cloning a gene of human CXCL10 (refer to FIG. 2), and the antigen protein was reacted with a library phage, thereby yielding a scFv-phage specifically binding to CXCL10, and then a panning process in which the scFv-phage was amplified in *E. coli* was performed. It was confirmed that a titer of colonies of phages undergoing third panning with respect to CXCL10 was amplified to $5.67 \times 10^8$ (refer to Table 1).

Also, the inventors selected a monoclonal phage antibody from the polyclonal phage antibody group having a high binding capacity, which underwent the third panning (refer to FIG. 3), and the monoclonal phage antibody was further selected through ELISA performed thereon (refer to Table 2). To classify and investigate the monoclonal phage selected as described above, fingerprinting and sequencing were performed (refer to FIG. 4), and thereby patterns and polypeptide sequences of CDR domains of VHs and VLs of the four types of the selected monoclonal antibodies were identified (refer to Tables 5 and 6).

Also, the inventors produced an antibody 10E by converting a phage clone 10E out of the four types of selected monoclonal phages into whole-form IgG and inserting heavy and light chains into vectors, respectively, and co-transfecting host cells with the vectors, thereby constructing a whole-form antibody, and then the binding affinity of the antibody to the CXCL10 antigen was measured at $7 \times 10^{-12}$M (refer to Table 8).

Also, the inventors produced an antibody HuE10-101, which is bispecific to TNF-α and CXCL10 by cloning the selected 10E gene in a plasmid of an anti-TNF-α monoclonal antibody, Humira (refer to FIG. 2). It was confirmed that the molecular weight of the antibody produced as described above was about 187 kDa (refer to FIG. 6), and it was shown by ELISA that the binding strength to TNF-α and CXCL10 were similar to that of HuE10-100 produced by the previous study (refer to FIG. 7). Additionally, it was confirmed by an LAL test that the cytotoxicity of the produced HuE10-101 antibody was 0.1 EU/ml or less (refer to FIG. 8).

Also, the inventors assessed in vitro inhibition activity of TNF-α or CXCL10 of the produced HuE10-101. Specifically, it was confirmed that the HuE10-101 antibody has a higher inhibitory activity than the Humira using WEHI164 cells having a TNF-α receptor (refer to FIGS. 41 and 42), and a decrease in chemotaxis of a cell and differentiation of osteoclasts showed that the HuE10-101 antibody has a CXCL10 inhibitory activity (refer to FIG. 43).

Therefore, it was confirmed that the TNF-α/CXCL10 bispecific antibody of the present invention has a high antigen binding capacity to both of TNF-α and CXCL10.

According to another aspect of the present invention, the present invention provides a transformant produced by co-transfection of host cells with an expression vector including a polynucleotide encoding a first antigen-binding site and an expression vector including a polynucleotide encoding a second antigen-binding site.

Due to the degeneracy of a codon or in consideration of a codon preferred by an organism in which the antibody is to be expressed, the polynucleotide encoding the antibody of the present invention may be changed to various forms at a coding domain without changing the amino acid sequence of an antibody expressed from the encoding domain, or changed or modified to various forms at other sites, excluding the coding domain, without affecting gene expression, and it will be clearly understood by those of ordinary skill in the art that such a modified gene is also included in the scope of the present invention. That is, the polynucleotide of the present invention may be mutated by substitution, deletion or insertion of one or more nucleic acid bases or a combination thereof, as long as the mutated polynucleotides encode proteins having the same activity, and those mutants are also included in the scope of the present invention. This polynucleotide sequence may be a single or double strand, and may represent a DNA or RNA (mRNA) molecule.

In construction of the expression vector, depending on a type of host cells for producing the antibody, expression regulatory sequences encoding a promoter, a terminator and an enhancer, and sequences involved in membrane targeting or secretion may be suitably selected and combined in various forms according to a purpose.

The expression vector of the present invention includes a plasmid vector, a cosmid vector, a bacteriophage vector and a virus vector, but the present invention is not limited thereto. A suitable expression vector may include a signal sequence for membrane targeting or secretion, or a leader sequence, in addition to expression regulatory elements such as a promoter, an operator, an initiation codon, a termination codon, a polyadenylation signal and an enhancer, and may be constructed in various forms according to a purpose. The promoter of the expression vector may be constitutive or inducible. When the hosts are *Escherichia* sp. bacteria, the signal sequence may be a PhoA signal sequence or OmpA signal sequence, when the hosts are *Bacillus* sp. bacteria, an α-amylase signal sequence or subtilisin signal sequence, when the hosts are yeasts, an MFα signal sequence or SUC2 signal sequence, and when the hosts are animal cells, an insulin signal sequence, α-interferon signal sequence or antibody molecule signal sequence, but the present invention is not limited thereto. Also, the expression vector may include a selection marker to select host cells containing a vector, and if it is a replicable expression vector, a replication origin is included.

According to another aspect of the present invention, the present invention provides a method of producing a TNF-α/CXCL10 double-targeting antibody, including (a) culturing the transformant; and 2) isolating the TNF-α/CXCL-10 double-targeting antibody from a cell culture obtained in the previous step.

The expression vector according to the present invention is introduced to transform suitable host cells, for example, *E. coli* or yeast cells, and the transformed host cells are cultured, thereby producing the antibodies according to the present invention at a large scale. Suitable culturing methods and medium conditions may be easily selected by known techniques by those of ordinary skill in the art depending on a type of host cells. The host cells may originate from a prokaryote such as *E. coli* or *Bacillus subtilis*. Alternatively, the host cells may be eukaryotic cells such as yeast cells originating from, for example, *Saccharomyces cerevisiae*, insect cells, plant cells, or animal cells. More preferably, the animal cells may be autologous or allogeneic animal cells. The transformant produced in the autologous or allogeneic animal cells may be administered into a subject in cell therapy for treating cancer. A method of introducing an expression vector into the host cells may be any method known to those of ordinary skill in the art.

According to another aspect of the present invention, the present invention provides a pharmaceutical composition for preventing or treating an immune disease including: (a) a pharmaceutically effective amount of the TNF-α/CXCL-10 double-targeting antibody; and (b) a pharmaceutically acceptable carrier.

The TNF-α/CXCL-10 double-targeting antibody of the present invention has a TNF-α inhibitory activity and an osteoclast differentiation inhibitory activity, and thus can be used as a pharmaceutical composition for preventing and treating an immune disease individually or in combination with a conventional pharmaceutically acceptable carrier.

The composition of the present invention may be useful as an immuno-suppressant to prevent graft rejection in a tissue or organ, which is mediated by an immune response. The graft rejection includes (1) a disease (that is, a graft-versus-host disease) triggered when graft-derived immune cells of a donor recognize a recipient as a foreign substance and attack the recipient and (2) a disease triggered when a recipient recognizes a graft of a donor as a foreign substance (that is, a graft rejection) due to a different genetic background between the donor of the graft (which is a part of the donor organism, for example, a cell, tissue or organ) and the recipient. As an example of the grafted tissue and organ in which rejection occurs, a heart, kidney, liver, medulla ossium, skin, cornea, lung, pancreas, intestinum tenue, limb, muscle, nerve, duodenum, small bowel, or pancreatic-insulin-islet-cell may be used, and the disease may be a graft-versus-host disease triggered by medulla ossium transplantation/graft.

Also, the composition of the present invention may also be applied in treatment and prevention of an autoimmune disease.

The autoimmune disease is a common name for a disease triggered by immune cells attacking themselves without discriminating themselves from a foreign substance. The autoimmune disease may be rheumatoid arthritis, systemic lupus erythematosus, hyperimmunoglobulin E, Hashimoto's thyroiditis, Grave's disease, multiple sclerosis, scleroderma, progressive systemic sclerosis, myasthenia gravis, type I diabetes, uveitis, allergic encephalomyelitis, glomerulonephritis, vitilligo, Goodpasture syndrome, Becet's disease, Crohn's disease, Ankylosing spondylitis, uveitis, thrombocytopenic purpura, pemphigus vulgaris, diabetes, autoimmune anemia, cryoglobulinemia, ALD, or systemic lupus erythematosus (SLE).

Also, the composition of the present invention may also be used to treat and prevent cutaneous manifestation of inflammatory and hyperproliferative skin diseases and an immune-mediated disease. Such diseases may include, for example, psoriasis, atopic dermatitis, contact dermatitis, eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, SLE, acne and alopecia areata.

Also, the composition of the present invention may be used to treat or prevent eye diseases or various autoimmune diseases. The diseases may include keratoconjunctivitis, vernal conjunctivitis, keratitis, herpetic keratitis, dystrophia epithelialis corneae, corneal leukoma, ocular pemphigus, Mooren's ulcer, scleritis, Graves' opthalmopathy, Vogt-Koyanagi-Harada syndrome, sarcoidosis, and multiple myeloma.

Also, the composition of the present invention may also be used to treat or prevent a chronic obstructive pulmonary disease (COPD), asthma (for example, bronchial asthma, allergic asthma, intrinsic asthma, extrinsic asthma and dust asthma), particularly, an obstructive airway disease such as chronic or endemic asthma (for example, terminal asthma and intolerant bronchial asthma), bronchitis, or allergic rhinitis.

The pharmaceutically acceptable carrier included in the pharmaceutical composition of the present invention is conventionally used in drug formulation, and may include, but is not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil. The pharmaceutical composition of the present invention may further include a lubricant, a wetting agent, a sweetener, a flavoring agent, an emulsifier, a suspending agent, and a preservative in addition to the above-described components. Suitable pharmaceutically acceptable carriers and preparations are described in detail in Remington's Pharmaceutical Sciences (19th ed., 1995).

The pharmaceutical composition of the present invention may be administered orally or parenterally, and for parenteral administration, the pharmaceutical composition may be administered by intravenous injection, subcutaneous injection, muscular injection, intraperitoneal injection, endothelial administration, local administration, nasal administration, intrapulmonary administration and rectal administration. For oral administration, an oral composition has to be formed in dosage forms in which an active drug is coated or protected from decomposition since a protein or peptide is digested. Also, the pharmaceutical composition may be administered by an optional tool that can transfer an active material into target cells.

A suitable dosage of the pharmaceutical composition of the present invention varies depending on factors such as a formulating method, an administration method, a patient's age, weight, sex, a pathological condition, a diet, an administration time, an administration route, an excretion rate and a reaction sensitivity, and a suitable dosage for desired treatment or prevention may be easily determined and prescribed by a normally skilled doctor. According to an exemplary embodiment of the present invention, a dose of the pharmaceutical composition ranges from 0.001 to 100 mg/kg/day. The term "pharmaceutically effective amount" used herein refers to an amount enough to prevent or treat an immune disease.

The pharmaceutical composition of the present invention may be prepared in unit contents or in a large-capacity container using a pharmaceutically acceptable carrier and/or excipient by a method that can be easily performed by those of ordinary skill in the art. Here, a dosage form of the composition may be a solution in an oil or aqueous medium, a suspension, an emulsion, an extract, a powder, a suppository, a granule, a tablet, or a capsule, and additionally include a dispersant or a stabilizer.

The antibody composition of the present invention may be administered individually or in combination with another therapeutic agent, and may be sequentially or simultaneously administered with a conventional therapeutic agent.

Antibodies may be administered in the form of an antibody-drug conjugate to treat an immune disease. The therapeutic agent includes a chemical therapeutic agent, a radioactive nuclide, an immuno-therapeutic agent, a cytokine, a chemokine, a toxin, a biological agent and an enzyme inhibitor. For example, in the literature (G. Gregoriadies, ed., Academic Press London, (1979); Amon et al., Recent Results in Cancer Res., 75: 236(1980); and Moolton et al., Immunolog. Res., 62:47(1982)), a method of binding antibiotics to the antibodies is disclosed.

Drugs suitable for coupling with the antibody or a fragment thereof are antibacterial, anthelmintic, antifungal and related drugs, for example, sulfonamide, penicillin, cephalosporin, aminoglycoside, tetracycline, chloramphenicol, piperazine, chloroquine, diaminopyridine, metroniazid, isoniazid, rifampin, streptomycin, sulfone, erythromycin, polymyxin, nystatin, amphotericin, 5-fluorocytosine, 5-iodo-2'-deoxyuradine, 1-adamantanamine, adenine arabinoside, amanitin, ribavirin and azidothymidine (AZT), and preferably, ribavirin. Several conditions appropriate and suitable for targeting a drug to a specific target site are disclosed, for example, in the literature (Trouet et al., Plenum Press, New York and London, 19-30 (1982)). Many problems occurring during treatment of a drug-tolerant infection may be solved by selectively killing infections by direct targeting of an infected lesion using an antibody constructed to have a high specificity to a microbial antigen as a therapeutic agent. Also, a medicinal effect of the drug targeting the lesion at the infected site may be increased with a high concentration.

An immunomodulator which can be used as a therapeutic agent in the antibody-drug conjugate includes a lymphokine and a cytokine, but the present invention is not limited thereto.

Advantageous Effects

Characteristics and advantages of the present invention are summarized below:

(a) A double-targeting antibody of the present invention is a bispecific antibody effectively binding to both of TNF-α and CXCL10, and thus can be useful as a double-targeting antibody capable of recognizing TNF-α/CXCL10.

(b) A composition of the present invention includes a TNF-α/CXCL-10 double-targeting antibody effectively binding to both of TNF-α and CXCL10.

(c) The double-targeting antibody of the present invention has superior TNF-α inhibitory activity and osteoclast differentiation inhibitory activity with respect to a TNF-α or CXCL10 single-targeting antibody.

(d) The composition of the present invention can be used to prevent or treat an immune disease.

DESCRIPTION OF DRAWINGS

FIG. 6 shows a purity of the purified HuE10-101 bispecific antibody.

FIG. 9 is a map of a HuE10-101 expression vector for constructing a production cell line.

FIG. 13 shows the result of comparing relative expression levels of single clones selected using DHFR by ELISA.

FIG. 16 is a microscopic image of a reserve cell line grown in a 100 nM MTX-containing medium.

FIG. 21 shows the homology of a theoretical amino acid sequence confirmed by LC-MS peptide mapping analysis after trypsin treatment to establish a morphological characteristic of HuE10-101.

MODES OF THE INVENTION

Hereinafter, exemplary examples will be provided to help in understanding of the present invention. It would be understood by those of ordinary skill in the art that the following examples are merely provided to facilitate understanding of the present invention, and the scope of the present invention is not limited to the following examples.

EXAMPLES

Example 1: Production of Human CXCL10 Antigen Protein

To construct a monoclonal antibody against human CXCL10, a human CXCL10 protein was expressed and purified. Specifically, to amplify the human CXCL10, a mixture of spleen, placenta, liver and kidney cDNA libraries was used as a template and inserted into a pET22b vector. A pET22b-human CXCL10 plasmid was transformed with BL21 (DE3), and an obtained transformant was inoculated into an ampicillin-containing LB plate and cultured overnight, followed by performing shaking culture at 37° C.

Figure 1:
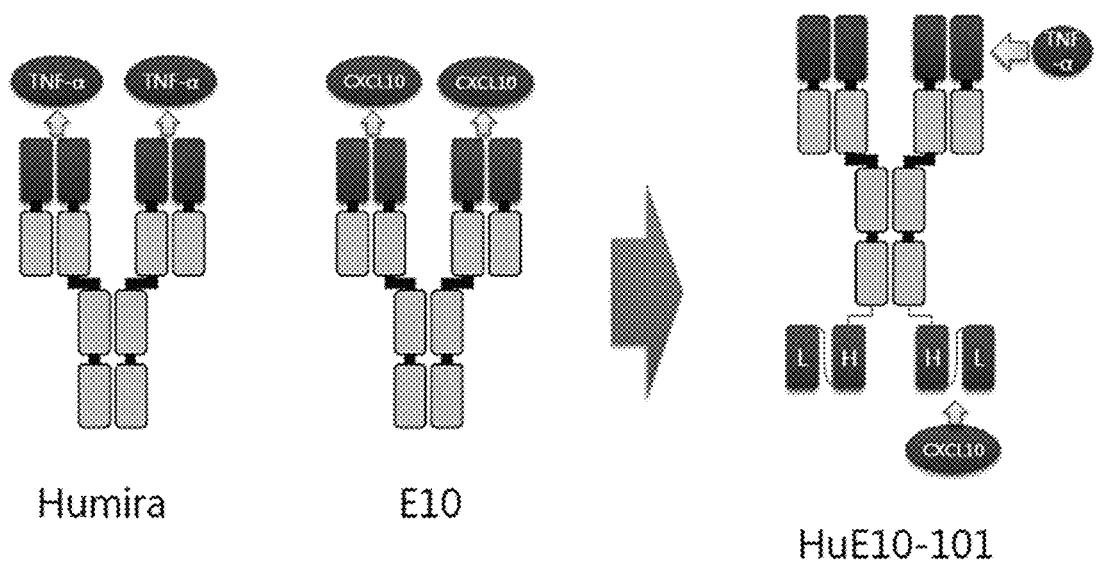
FIG. 1 is a schematic diagram illustrating production of a TNF-α/CXCL10 bispecific antibody.
Figure 2:
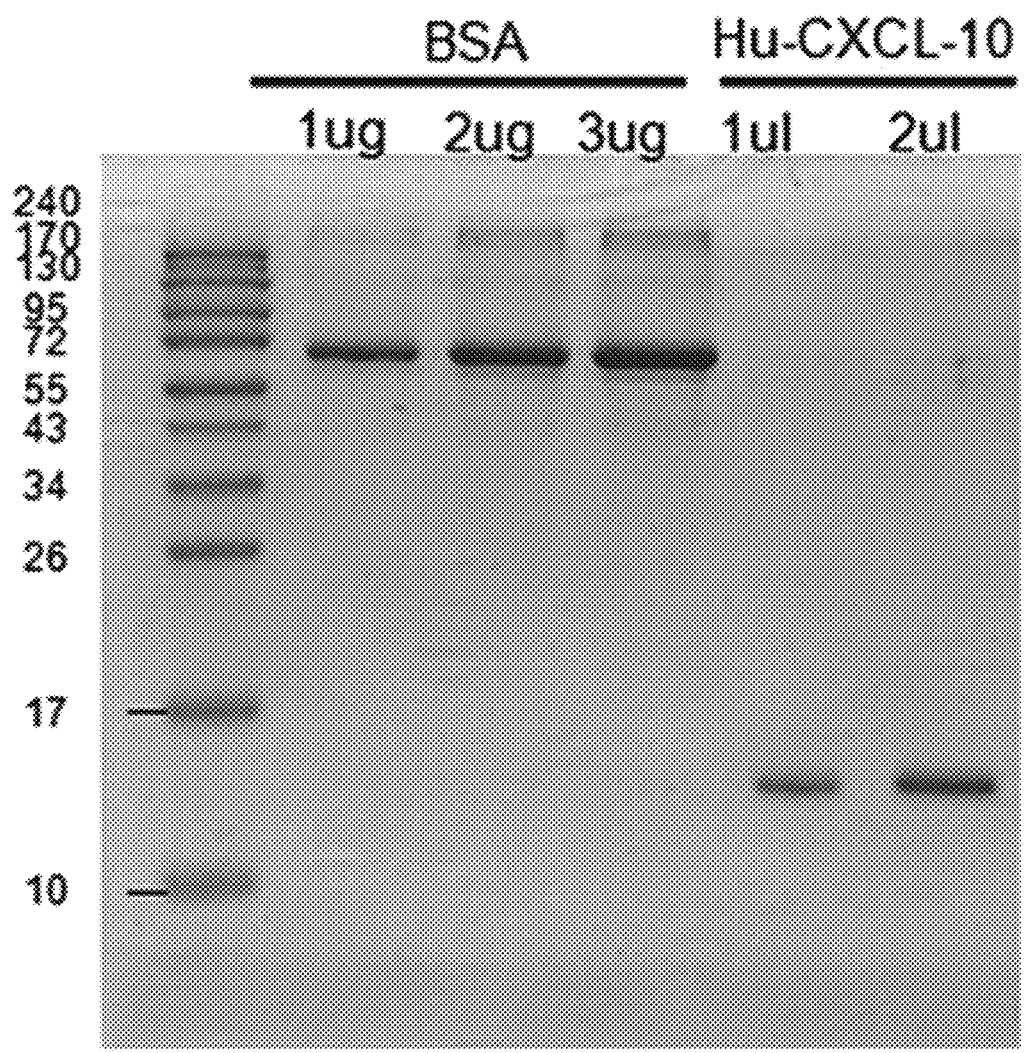
FIG. 2 shows a human CXCL10 protein purified by Ni-NTA column chromatography.

Afterward, when OD600 was 0.55, IPTG was added to the cells at 0.5 mM, cultured overnight, and centrifuged at 6,500 rpm and 4° C. for 15 minutes, thereby obtaining a supernatant. The obtained supernatant was concentrated and reacted with a Ni-NTA agarose, and then eluted by filling a column with agarose beads. After concentration, the resultant product was loaded on 15% SDS-PAGE gel, and stained with coomassie. To compare the degree of expression of the protein, bovine serum albumin (BSA) was also used as a protein concentration standard. Consequently, as shown in FIG. 2, the expression of a human CXCL10 protein having a size of about 15 kDa was identified.

Example 2: Construction of Monoclonal Antibody 2-1. Panning Process

Panning is a process of only selecting phages displaying peptides on their surface from phage libraries displaying peptides on a coat of the phage, the peptides having a property of binding with a target molecule (an antibody, an enzyme, a cell-surface receptor, etc.). To construct a phage antibody group for constructing a monoclonal antibody against CXCL10, phage panning was carried out. 100 μg of the purified human CXCL10 antigens obtained in Example 1 was coated with 2 ml of a coating buffer ($Na_2CO_3$(Sigma, 57795) 1.59 g $NaHCO_3$(Sigma, 58875) 2.93 g $NaN_3$(Sigma, S2002), 0.2 g) in an immunosorb tube (Nunc 470319) at 4° C. for about 16 hours in a rotator and diluted in PBS at room temperature for 2 hours, and then the reaction in the immunosorb tube was blocked with 4% skim milk ((BD, 232100)-4% in 1×PBS). 2 ml of library phages were added to the immunosorb tube and allowed to be reacted at room temperature for 2 hours, and then washed with PBST (0.05%) five times and PBS twice. After washing, only specifically binding scFv-phages were eluted with 100 mM TEA (Sigma T-0886), and the eluted phages were injected into E. coli (XL1-Blue, Stratagene, 200249) and amplified. Second and third pannings were performed on the phages amplified by the first panning in the washing step with PBST (140 mM NaCl(Sigma, S7953-5 kg) 8 g of 10 mM $Na_2HPO_4$(Sigma, S7907-dibasic) 1.15 g of 1.8 mM $KH_2PO_4$(Sigma, S-5655-500 g: monobasic) 0.2 g of 2.7 mM KCl (Sigma p9541) 0.2 g of Tween20 (Sigma, p1379) 0.55%) with the increasing number of cycles (second panning: 13 times, third panning: 23 times) by the same method as used in the first panning. As a result, it was confirmed in Table 1 that a colony titer of the phage against an antigen in the third panning was increased at least 100 times (Table 1).

TABLE 1

Colony titer of anti-human CXCL10 phage depending on number of panning cycles

| Target antigen | Panning cycles | Number of input phages | Number of phage bindings |
|---|---|---|---|
| Human CXCL10-His | First | $2.6 \times 10^{13}$ | $4.8 \times 10^{6}$ |
| | Second | $3 \times 10^{13}$ | $6 \times 10^{5}$ |
| | Third | $1 \times 10^{13}$ | $5.67 \times 10^{8}$ |

2-2. Screening of Phage Antibody

A cell stock stored in a refrigerator after the first to third pannings was added to a 5 ml of 2×YTCM, 2% glucose, 5 mM $MgCl_2$ medium to have an OD600 of 0.1, and cultured at 37° C. for 2 to 3 hours (OD600=0.5 to 0.7). The cultured cell stock was inoculated with M1 helper phages and cultured in a 2×YTCMK, 5 mM $MgCl_2$, 1 mM IPTG medium at 30° C. for 16 hours. The cultured cells were centrifuged at 4500 rpm for 15 minutes at 4° C., and a supernatant (first to third-panned poly scFv-phages) was transferred to a new tube. Two types of antigens (CXCL10, α-myc) were treated with a coating buffer at 100 ng per well at 4° C. for about 16 hours and applied to a 96-well immunoplate (NUNC 439454), and a reaction in each well was blocked with skim milk (4%) dissolved in PBS. Each well was washed with 0.2 ml of PBS-Tween20 (0.05%), first, second and third-panned poly scFV-phages were added to each well by 100 µl and allowed to be reacted at room temperature for 2 hours. After the reaction, each well was washed with 0.2 ml of PBS-Tween20 (0.05%) four times, and a secondary antibody, anti-M13-HRP (Amersham 27-9421-01), was diluted at 1:2000 and allowed to be reacted with the phages at room temperature for 1 hour. After the reaction, the wells were washed with 0.2 ml of PBS-Tween20 (0.05%), and a substrate solution prepared by dissolving an OPD tablet (Sigma, 8787-TAB) in a PC buffer (5.1 g $C_6H_8O_7H_2O$ (Sigma, C0706), 7.3 g $Na_2HPO_4$ (Sigma, S7907)) was added at 100 µl per well and allowed to develop a color for 10 minutes, and then an absorbance was measured at 490 nm using a spectrophotometer (MolecularDevice, U.S.A.).

Figure 3:
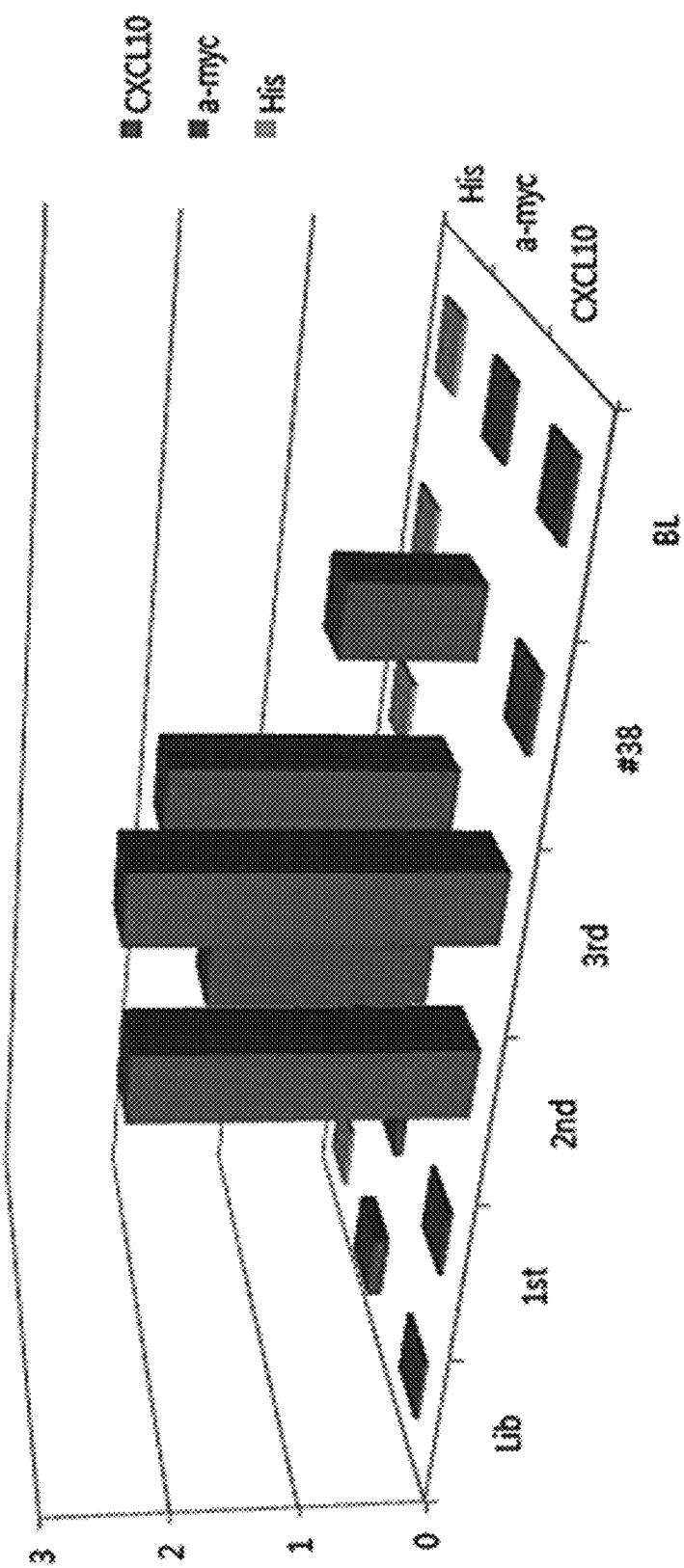
FIG. 3 shows a poly-phage ELISA result for human CXCL10-His using a phage pool after panning.

As a result, in FIG. 3, enrichment of a binding capability with respect to two types of antigens in third poly scFV-phages was assessed by ELISA (FIG. 3).

2-3. Selection of Monoclonal Phages

A colony obtained from the polyclonal phage antibody group (third panning) having a large binding capability constructed in Example 2-2 was dispensed into a 96-deep well plate (Bionia, 90030) having 1 ml of a medium containing 2×YTCM, 2% glucose and 5 mM $MgCl_2$ and cultured at 37° C. for 16 hours. In order to have an OD600 of the cultured cells of 0.1, 100 to 200 µl of the cultured cells were taken and diluted with 1 ml of a 2×YTCM, 2% glucose, 5 mM $MgCl_2$ medium, dispensed into a 96-deep well plate, and cultured at 37° C. for 2 to 3 hours to have an OD600 of 0.5 to 0.7. After M1 helper phages were injected to have an MOI ratio of 1:20, and cultured in a 2×YTCMK, 5 mM $MgCl_2$, 1 mM IPTG medium at 30° C. for 16 hours. The cultured cells were centrifuged at 4,500 rpm and 4° C. for 15 minutes, and a supernatant was obtained, 4% PEG 6,000 and 3% NaCl were added thereto and well dissolved, and allowed to be reacted on ice for 1 hour. After the reaction, the resultant product was centrifuged at 8,000 rpm and 4° C. for 20 minutes, and a pellet was dissolved in PBS and centrifuged again at 12,000 rpm and 4° C. for 10 minutes, thereby obtaining a supernatant, and the supernatant was transferred to a new tube and subjected to third panning Monoclonal scFv-phages obtained thereby were stored at 4° C.

2-4. ELISA Analysis for Monoclonal Phage Antibody Group

Two types of antigens such as CXCL10 and α-myc were put into a 96-well immunoplate at 100 ng per well and coated with a coating buffer at 4° C. for 16 hours, and wells were blocked with skim milk (4%) dissolved in PBS. Each well was washed with 0.2 ml of PBS-Tween20 (0.05%), and the monoclonal scFv-phages obtained by the third panning (each 100 scFv-phage) were added at 100 µl per well, and allowed to be reacted at room temperature for 2 hours. Each well was washed again with 0.2 ml of PBS-Tween20 (0.05%) four times, and a secondary antibody, anti-M13-HRP, was diluted at 1/2000 and allowed to be reacted at room temperature for 1 hour. Each well was washed with 0.2 ml of PBS-Tween20 (0.05%) and allowed to develop a color to measure an absorbance at 490 nm.

Consequently, as shown in Table 2, a total of 59 monoclonal phages against human CXCL10-His were obtained as monoclonal phages having a high binding capacity to each antigen were obtained (Table 2).

TABLE 2

ELISA results for single phages against antigen, human CXCL10-His

| Clone name | CXCL10 | a-myc | His | Ratio | Clone name | CXCL10 | a-myc | His | Ratio | Clone name | CXCL10 | a-myc | His | Ratio |
|---|---|---|---|---|---|---|---|---|---|---|---|---|---|---|
| 1A | 0.042 | 0.042 | 0.056 | 1.014 | 2A | 1.714 | 1.205 | 0.040 | 1.422 | 3A | 0.050 | 0.040 | 0.039 | 1.243 |
| 1B | 2.754 | 0.402 | 0.039 | 6.846 | 2B | 0.040 | 0.039 | 0.039 | 1.026 | 3B | 2.643 | 0.426 | 0.039 | 6.206 |
| 1C | 0.098 | 0.039 | 0.039 | 2.519 | 2C | 2.913 | 1.117 | 0.040 | 2.608 | 3C | 2.702 | 0.468 | 0.039 | 5.773 |
| 1D | 0.652 | 0.778 | 0.044 | 0.838 | 2D | 0.040 | 0.039 | 0.040 | 1.003 | 3D | 0.067 | 0.041 | 0.039 | 1.639 |
| 1E | 0.039 | 0.051 | 0.038 | 0.757 | 2E | 1.537 | 0.846 | 0.043 | 1.817 | 3E | 0.040 | 0.038 | 0.039 | 1.045 |
| 1F | 0.038 | 0.051 | 0.038 | 0.735 | 2F | 2.895 | 0.706 | 0.038 | 4.102 | 3F | 0.585 | 0.050 | 0.039 | 11.622 |
| 1G | 0.039 | 0.069 | 0.028 | 0.564 | 2G | 0.039 | 0.044 | 0.040 | 0.890 | 3G | 1.332 | 0.093 | 0.038 | 14.358 |
| 1H | 0.208 | 0.052 | 0.035 | 4.031 | 2H | 2.842 | 2.863 | 0.133 | 0.993 | 3H | 0.051 | 0.040 | 0.027 | 1.298 |
| 4A | 0.041 | 0.050 | 0.041 | 0.817 | 5A | 2.870 | 0.407 | 0.091 | 7.050 | 6A | 2.950 | 2.950 | 0.558 | 1.000 |
| 4B | 0.040 | 0.045 | 0.048 | 0.893 | 5B | 2.341 | 2.628 | 0.408 | 0.891 | 6B | 2.935 | 2.909 | 0.551 | 1.009 |

TABLE 2-continued

ELISA results for single phages against antigen, human CXCL10-His

| Clone name | CXCL10 | a-myc | His | Ratio | Clone name | CXCL10 | a-myc | His | Ratio | Clone name | CXCL10 | a-myc | His | Ratio |
|---|---|---|---|---|---|---|---|---|---|---|---|---|---|---|
| 4C | 0.059 | 0.074 | 0.038 | 0.799 | 5C | 3.067 | 0.261 | 0.046 | 11.754 | 6C | 2.540 | 0.303 | 0.125 | 8.390 |
| 4D | 0.535 | 0.483 | 0.040 | 1.109 | 5D | 2.347 | 2.563 | 0.162 | 0.916 | 6D | 0.058 | 0.041 | 0.063 | 1.426 |
| 4E | 0.038 | 0.040 | 0.039 | 0.946 | 5E | 0.038 | 0.040 | 0.091 | 0.948 | 6E | 2.143 | 0.186 | 0.119 | 11.494 |
| 4F | 0.972 | 0.068 | 0.044 | 14.335 | 5F | 0.533 | 0.047 | 0.137 | 11.415 | 6F | 2.931 | 0.325 | 0.061 | 9.016 |
| 4G | 0.053 | 0.040 | 0.038 | 1.320 | 5G | 0.450 | 0.047 | 0.060 | 9.624 | 6G | 2.844 | 0.420 | 0.080 | 6.766 |
| 4H | 0.175 | 0.045 | 0.030 | 3.937 | 5H | 0.318 | 0.043 | 0.043 | 7.474 | 6H | 2.474 | 2.748 | 0.136 | 0.900 |
| 7A | 3.145 | 1.446 | 0.153 | 2.175 | 8A | 2.991 | 2.765 | 0.110 | 1.082 | 9A | 2.703 | 0.095 | 0.048 | 28.366 |
| 7B | 3.024 | 2.409 | 0.061 | 1.255 | 8B | 2.991 | 0.197 | 0.039 | 15.166 | 9B | 2.944 | 0.173 | 0.043 | 17.027 |
| 7C | 2.969 | 0.121 | 0.083 | 24.453 | 8C | 2.996 | 0.144 | 0.062 | 20.832 | 9C | 2.641 | 0.076 | 0.039 | 34.893 |
| 7D | 3.083 | 0.367 | 0.049 | 8.399 | 8D | 3.079 | 2.920 | 0.236 | 1.054 | 9D | 2.422 | 1.504 | 0.040 | 1.610 |
| 7E | 2.302 | 0.052 | 0.047 | 44.277 | 8E | 3.012 | 0.103 | 0.039 | 29.385 | 9E | 2.958 | 2.006 | 0.043 | 1.475 |
| 7F | 3.084 | 0.374 | 0.043 | 8.255 | 8F | 2.813 | 0.061 | 0.057 | 46.343 | 9F | 1.047 | 2.140 | 0.051 | 0.489 |
| 7G | 2.250 | 0.183 | 0.057 | 12.294 | 8G | 2.636 | 2.730 | 0.072 | 0.966 | 9G | 0.633 | 0.042 | 0.042 | 15.224 |
| 7H | 1.447 | 0.870 | 0.035 | 1.663 | 8H | 2.470 | 2.755 | 0.112 | 0.897 | 9H | 0.339 | 0.191 | 0.073 | 1.773 |
| 10A | 2.970 | 0.410 | 0.042 | 7.245 | 11A | 2.539 | 0.059 | 0.047 | 43.034 | 12A | 3.018 | 0.310 | 0.054 | 9.722 |
| 10B | 2.844 | 0.098 | 0.045 | 28.991 | 11B | 2.917 | 0.186 | 0.042 | 15.651 | 12B | 2.782 | 0.207 | 0.043 | 13.450 |
| 10C | 0.044 | 0.048 | 0.045 | 0.925 | 11C | 2.669 | 0.071 | 0.049 | 37.862 | 12C | 0.061 | 0.043 | 0.045 | 1.418 |
| 10D | 2.853 | 3.021 | 0.178 | 0.945 | 11D | 3.116 | 0.425 | 0.049 | 7.324 | 12D | 3.015 | 0.888 | 0.049 | 3.396 |
| 10E | 3.051 | 0.307 | 0.051 | 9.946 | 11E | 3.044 | 2.966 | 0.459 | 1.026 | 12E | 0.201 | 0.052 | 0.046 | 3.875 |
| 10F | 2.989 | 0.347 | 0.043 | 8.613 | 11F | 2.994 | 3.067 | 0.421 | 0.976 | 12F | 2.927 | 0.421 | 0.039 | 6.953 |
| 10G | 3.038 | 0.756 | 0.045 | 4.018 | 11G | 3.041 | 3.090 | 0.491 | 0.984 | 12G | 2.840 | 0.350 | 0.045 | 8.115 |
| 10H | 2.960 | 3.014 | 0.213 | 0.982 | 11H | 3.081 | 2.187 | 0.054 | 1.409 | 12H | 3.009 | 0.529 | 0.037 | 5.690 |

Example 3: Classification and Investigation of Selected Monoclonal Phages 3-1. Verification by Fingerprinting To verify the 10 monoclonal cells selected in Example 2 by fingerprinting, 1 μl of the selected monoclonal cells were mixed with 0.2 μl of a Taq DNA polymerase (Gendocs, 5 U/μl), 0.2 μl each of 50 p/μl of a forward primer (pelB5) (SEQ ID NO: 41: 5'-CTAGATAACGAGGGCAAATCATG-3') and reverse primer (cla3)(SEQ ID NO: 42: 5'-CGTCAC-CAATGAAACCATC-3'), 3 μl of 10× buffer, 0.6 μl of 10 mM dNTP mix and 24.8 μl of distilled water, and colony PCR (iCycler iQ, BIO-RAD) was carried out under the following conditions for the PCR program shown in Table 3.

TABLE 3

| Temperature | Time | Cycle |
|---|---|---|
| 95° C. | 5 min | 1 |
| 95° C. | 30 sec | 30 cycles |
| 56° C. | 30 sec | |
| 72° C. | 1 min | |
| 72° C. | 10 min | 1 |
| 4° C. | — | — |

A colony PCR product obtained thereby was identified on a 1% agarose gel (Seakem LE, CAMERES 50004), 0.2 μl of BstNI (Roche11288075001, 10 U/μl) was added to the PCR product, and allowed to be reacted under the following reaction conditions shown in Table 4 at 37° C. for 2 to 3 hours.

TABLE 4

| 10× Buffer | 3 μl |
|---|---|
| Colony PCR product | 10 μl |
| BstNI (10 U/μl) | 0.2 μl |
| Distilled water | 16.8 μl |

Figure 4:
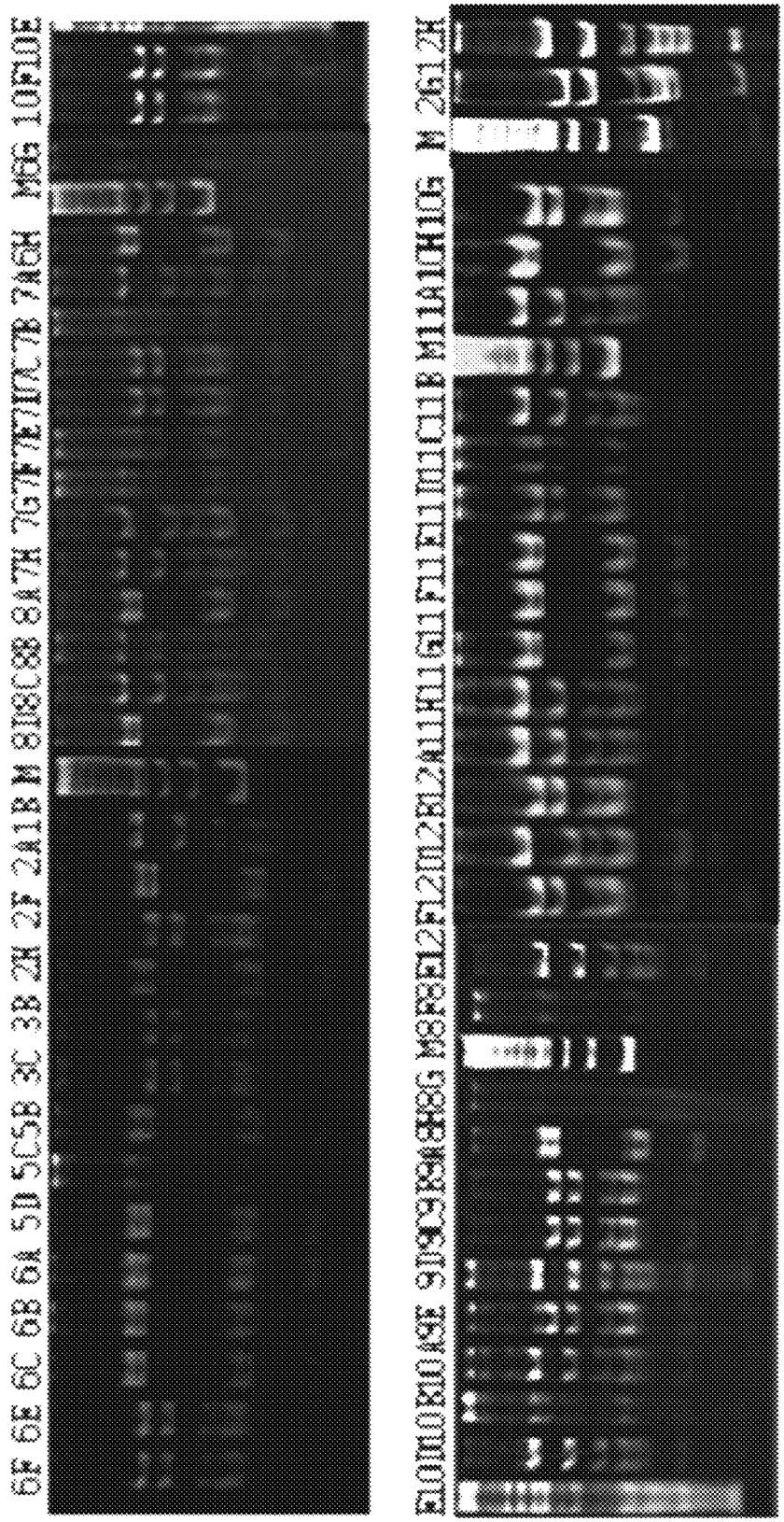
FIG. 4 shows a BstNI fingerprinting result for scFv mono-phage clones of human CXCL10. A scFv insert was amplified from an individual colony, and the amplified product was restricted with BstNI and analyzed using an 8% polyacrylamide gel. Clones marked with a blue letter is represented a different group.

As a result, fragments of the monoclonal phage antibodies digested with BstNI were identified on a 8% DNA polyacryl amide gel (30% acrylamide(Bio-RAD, 161-0156) 2.66 ml, 10×TBE 1 ml, distilled water 6.27 ml, 10% APS(sigma, A3678) 70 μl, TEMED(Bio-RAD, 161-0801) 7 μl), and as shown in FIG. 3, the diversity of monoclonal phage antibodies was confirmed (FIG. 4).

3-2. Verification by Sequencing

To analyze each sequence of the monoclonal phages identified by fingerprinting in Example 3-1, monoclonal cells were cultured in a 2×YTCM, 2% glucose, 5 mM MgCl$_2$ medium (5 ml) at 37° C. for 16 hours. DNA was obtained from the cultured single cells using a DNA purification kit (Nuclogen, 5112), and sequencing with a pelB5 primer (SEQ ID NO: 43: 5'-CTAGATAACGAGGGCAAATCATG-3') (Solgent, Korea) was requested to identify the VH and VL in a CDR domain of the selected antibody. From the analyzed sequence, similarity between those antibodies and a germ line antibody group was analyzed with polypeptides used in the heavy and light chains of CDR3s of each human antibody using the Ig BLAST program (//www.ncbi.nlm.ni-h.gov/igblast/) of NCBI.

Consequently, as shown in Table 5, phage antibodies specific to four types of human CXCL10s were obtained, and their amino acid sequences are shown in Table 6.

TABLE 5

List of monoclonal antibodies obtained against human CXCL10-His antigens

| Clone name | VH | Similarity | VL | Similarity | VH (CDR3-A/a sequence) | Vk (CDR3-A/a sequence) | Hu CXCL10 | a-myc | His | Ratio |
|---|---|---|---|---|---|---|---|---|---|---|
| 10D | VH 3-30 | 292/296 (98.65%) | V2-1 | 243/282 (86.17%) | DKRAAFDI (SEQ ID NO: 19) | MTWDVDT TSMI (SEQ ID NO: 31) | 2.853 | 3.021 | 0.178 | 0.945 |
| 10E | VH 3-30 | 281/296 (94.93%) | V1-13 | 283/295 (95.93%) | DSGSYLDW YFDL (SEQ ID NO: 27) | QSYDSRLG VV (SEQ ID NO: 15) | 3.051 | 0.307 | 0.051 | 9.946 |
| 9E | VH 3-30 | 289/296 (97.64) | V2-14 | 265/283 (93.64%) | DSGSYLDW YFDL (SEQ ID NO: 27) | QVWDSSSD RPV (SEQ ID NO: 39) | 2.958 | 2.006 | 0.043 | 1.475 |
| 12D | VH 3-30 | 275/296 (92.91%) | V2-1 | 243/282 (86.17%) | DGLAAKLG H (SEQ ID NO: 23) | MTWDVDT TSMI (SEQ ID NO: 31) | 3.015 | 0.888 | 0.049 | 3.396 |

TABLE 6

Amino acid sequences of monoclones against human CXCL10

| Clone name | Heavy chain | | | Light chain | | |
|---|---|---|---|---|---|---|
| | CDR1 | CDR2 | CDR3 | CDR1 | CDR2 | CDR3 |
| 10D | SYGMH (SEQ ID NO: 17) | WVAVISYDGSNKYYADS VKG (SEQ ID NO: 18) | DKRAAFDI (SEQ ID NO: 19) | CSGDNLRTKYVS (SEQ ID NO: 29) | QDTRRPS (SEQ ID NO: 30) | MTWDVDTTS MI (SEQ ID NO: 31) |
| 12D | RYGMH (SEQ ID NO: 21) | WVALISYDGSNKYYADS VKG (SEQ ID NO: 22) | DGLAAKLGH (SEQ ID NO: 23) | CSGDNLRTKYVS (SEQ ID NO: 33) | QDTRRPS (SEQ ID NO: 34) | MTWDVDTTS MI (SEQ ID NO: 35) |
| 10E | SYGMH (SEQ ID NO: 9) | WVAVISYDGNSKYYADS VKG (SEQ ID NO: 10) | DSGSYLDWYF DL (SEQ ID NO: 11) | CTGSRSNFGAGH DVH (SEQ ID NO: 13) | GNNNR PS (SEQ ID NO: 14) | QSYDSRLGV V (SEQ ID NO: 15) |
| 9E | SYGMH (SEQ ID NO: 25) | WVAVISYDGNNKYYVDS VKG (SEQ ID NO: 26) | DSGSYLDWYF DL (SEQ ID NO: 27) | CGGGNIRDKSVH (SEQ ID NO: 37) | YDSDRP S (SEQ ID NO: 38) | QVWDSSSDR PV (SEQ ID NO: 39) |

Example 4: Conversion and Analysis of Whole IgG

4-1. Conversion of Whole-Form IgG

To convert antibodies of the four types of monoclonal phages from scFv to IgG in Example 3-2, for the heavy chain, 1 µl of monoclonal DNA, 10 pmole/µl each of a heavy chain forward primer and a heavy chain reverse primer, 5 µl of 10× buffer, 1 µl of 10 mM dNTP mix, pfu DNA polymerase (Solgent, 2.5 U/µl) and 0.5 µl distilled water were mixed, and colony PCR (iCycler iQ, BIO-RAD) was carried out. Also, for the light chain, colony PCR was carried out by the same method using the light chain forward and reverse primers. The primers used to confirm the four types of monoclonal phages from scFv to IgG are shown in Table 7.

TABLE 7

Sequences of primers used in IgG conversion

| Clone Name | | Forward primer | Reverse primer |
|---|---|---|---|
| 10D | heavy chain | 5'-CAGGTGCAGCTGGTGCAGTC-3' (SEQ ID NO: 43) | 5'-TGAGGAGACGGTGA-3' (SEQ ID NO: 44) |

TABLE 7-continued

Sequences of primers used in IgG conversion

| Clone Name | | Forward primer | Reverse primer |
|---|---|---|---|
| | light chain | 5'-TCCTATGAGCTGACACAGGC-3' (SEQ ID NO: 45) | 5'-TAGGACGGTCAGCTTGGTCCC-3' (SEQ ID NO: 46) |
| 12D | heavy chain | 5'-CAGGTGCAGCTGGTGCAGTC-3' (SEQ ID NO: 47) | 5'-TGAGGAGACGGTGA-3' (SEQ ID NO: 48) |
| | light chain | 5'-TCCTATGAGCTGACACAGGC-3' (SEQ ID NO: 49) | 5'-TAGGACGGTCAGCTTGGTCCC-3' (SEQ ID NO: 50) |
| 10E | heavy chain | 5'-CAGGTGCAGCTGGTGCAGTC-3' (SEQ ID NO: 51) | 5'-TGAGGAGACGGTGA-3' (SEQ ID NO: 52) |
| | light chain | 5'-CAGTTCGTGCTGACTCAGCC-3' (SEQ ID NO: 53) | 5'-TAGGACGGTCAGCTTGGTCCC-3' (SEQ ID NO: 54) |
| 9E | heavy chain | 5'-CAGGTGCAGCTGGTGGAGTC-3' (SEQ ID NO: 55) | 5'-TGAGGAGACGGTGA-3' (SEQ ID NO: 56) |
| | light chain | 5'-AATTTTATGCTGACTCAGCC-3' (SEQ ID NO: 57) | 5'-TAGGACGGTCAGCTTGGTCCC-3' (SEQ ID NO: 58) |

Afterward, the heavy chain gene obtained by PCR was purified with a DNA-gel extraction kit (Qiagen), 1 μl of a pNATAB H vector (10 ng), 15 μl of a heavy chain (100 to 200 ng), 2 μl of 10× buffer, 1 μl of a ligase (1 U/μl), and distilled water were mixed and stored at room temperature for 1 to 2 hours to be linked with a vector. The heavy chain gene-linked pNATAB H vector was maintained on ice with transforming cells (*E. coli* XL1-blue) for 30 minutes, transfected by heat shock at 42° C. for 90 seconds, maintained again on ice for 5 minutes. 1 ml of an LB medium was injected into the cells and cultured at 37° C. for 1 hour. Afterward, the cells were seeded on an ampicillin-containing LB solid medium and cultured at 37° C. for 16 hours. A single colony produced after the culture was injected into 5 ml of an ampicillin-containing LB liquid medium and cultured at 37° C. for 16 hours. DNA was extracted from the cell culture using a DNA-prep kit (Nuclogen). Also, DNA of the light chain was extracted using a pNATAB L vector by the same method as described above.

4-2. Purification of Anti-CXCL10 Antibody and Measurement of Antigen Binding Affinity The extracted whole-form antibody DNA was co-transfected by adding 40 μg of PEI, 10 μg of DNA and 10 μg of light chain DNA to 293E cells (Invitrogen). Supernatants obtained by transfection from day 2 to day 8 were obtained and purified with protein A beads, and ELISA was carried out to measure a binding strength of the purified human CXCL10 antibody to an antigen.

Specifically, ELISA was carried out by coating a recombinant human CXCL10 protein with a coating buffer at 100 ng per well in a 96-well immunoplate at 4° C. for 16 hours, and a reaction in each well was blocked with skim milk (4%) dissolved in PBS. 0.2 ml of PBS-Tween20 (0.05%) was added to wash each well, monoclonal antibodies were sequentially diluted from 50 nM by ½, added at 100 μl each to an antigen-coated plate, and allowed to be reacted at room temperature for 2 hours. 0.2 ml of PBS-Tween20 (0.05%) was added again to wash each well three times, and a secondary antibody, anti-human Fc-HRP, was diluted at 1:4000 and allowed to be reacted at room temperature for 50 minutes. The plate was washed with 0.2 ml of PBS-Tween20 (0.05%), and a substrate solution prepared by adding an OPD table to a PC buffer was added to the plate at 100 μl per well to allow color development for 5 minutes, followed by measuring an absorbance at 490 nm using a spectrophotometer. The ELISA result was analyzed using a Graphpad prism ver. 4 software (CA 92037: Graphpad Software Inc., USA).

Consequently, as shown in Table 8, it was confirmed that a binding strength (1(D)) of the purified anti-CXCL10 antibody against an antigen is excellent (Table 8).

TABLE 8

KD value of purified whole IgG antibodies against human CXCL10

| Antibody name | KD value | $R^2$ |
|---|---|---|
| 9E | $6.1 \times 10^{-12}$ | 0.98 |
| 10E | $7 \times 10^{-12}$ | 0.98 |
| 12D | $4.7 \times 10^{-12}$ | 0.98 |
| 10D | $2.5 \times 10^{-12}$ | 0.99 |

Example 5: Construction of Bispecific Antibody Against CXCL10 and TNF-α

5-1. Construction and Purification of Bispecific Antibody, HuE10-101

To construct a bispecific antibody prepared by fusion of an anti-human CXCL10 monoclonal antibody and a blockbuster anti-TNF-α monoclonal antibody, Humira, E10 scFv among the anti-human CXCL10 monoclonal antibodies constructed in Example 3 was cloned at the 3'-end of pNATAB-H:Humira, and named HuE10-101.

The anti-TNF-α antibody, Humira, was constructed by gene synthesis based on the amino acid sequence (SEQ ID NO: 4) of a heavy chain variable domain and the amino acid sequence (SEQ ID NO: 8) of a light chain variable domain. After then, to link the E10 scFv to 3'-ends of the heavy chain and variable domains of Humira in a vector including the heavy chain domain of the Humira, PCR was carried out to form one DNA fragment by linking two fragments, and a pNATABH:Humira/E10 scFv vector for expressing HuE10-101 was constructed by inserting the DNA fragment into a pNATABH vector. Subsequently, HEK 293E cells (Invitrogen) were co-transfected with pNATABH:Humira/E10 scFv and pNATABH:Humira in 3:7. Supernatants obtained four times after transfection every third day from day 2 to day 8, and an expression level of the antibody was confirmed by western blotting (FIG. 5) and purified with protein A beads. The western blotting was carried out by collecting a cell culture every third day, inputting the collected cells into a 1 ml tube, centrifuging the cells at 5000 rpm for 5 minutes to remove the cells, thereby obtaining a supernatant. 25 µl of a protein sample buffer and 125 µl of the supernatant were put into a 1 ml tube and boiled for 5 minutes. The resultant product was loaded on a 10% SDS-PAGE gel at 40 µl, subjected to electrophoresis, and transferred to a membrane. After the membrane was blocked with 4% skim milk for about 1 hour, a secondary antibody, anti-Fc-HRP, was added in 1/4000 and shaken at room temperature about 4 hours. The resultant membrane was washed with 1×PBST three times, 1 ml of an ECL solution was sprayed on the membrane, and then the membrane was exposed to an X-ray film in a dark room.

Figure 5:
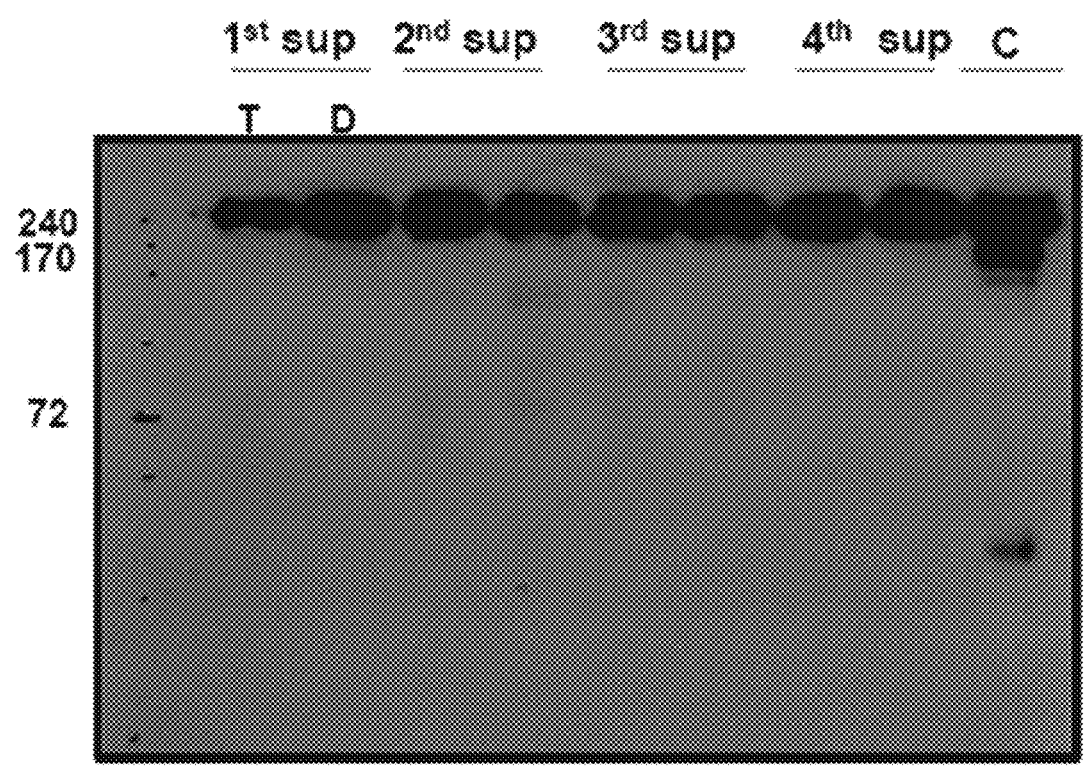
FIG. 5 shows expression rates of a HuE10-101 bispecific antibody assessed by culture period.

Consequently, as shown in FIG. 5, expression of the HuE10-101 antibody was detected, and a recovery rate of the finally purified antibody was 7 mg/L, which shows that a large amount of the antibodies were expressed even by a method using transient expression (FIG. 6).

Also, for QC analysis for purified antigens, a gel-like image and absolute quantification were confirmed using chips of an Agilent Protein 230 kit (5067-1517) in an Agilent 2100 Bioanalyzer (manufactured by Agilent Technologies Inc., Germany). The analysis was carried out under each of a reducing condition and a non-reducing condition, and as a control group, Humira was analyzed, too.

Consequently, as shown in FIG. 6, under the reducing condition, the molecular weights of the heavy and light chains of Humira are 50 and 25 kDa, respectively, and the molecular weights of the heavy and light changes of HuE10-101 are 83 and 25 kDa, respectively, and therefore it was seen that the heavy chain domain of Humira is fused with E10 scFv, thereby increasing the molecular weight. Under the non-reducing condition, it was seen that the molecular weight of HuE10-101 is about 187 kDa (FIG. 6).

5-2. Investigation of Binding Strength of Bispecific Antibody, HuE10-101, Against CXCL10 and TNF-α

To confirm a specific binding strength of the bispecific antibody, HuE10-101, against CXCL10 or TNF-α, ELISA was carried out by the same method as described in Example 4-2. To compare a level of the binding strength of HuE10-101, analysis for a HuE10-100 antibody was carried out by the same method. Meanwhile, the HuE10-100 antibody was constructed by linking E10 scFv to an N-terminus of a heavy chain variable domain of Humira. While the HuE10-100 antibody is a bispecific antibody against TNF-α and CXCL10, like HuE10-101, it has a disadvantage of an ultimately low expression level, compared to the HuE10-101.

Figure 7:
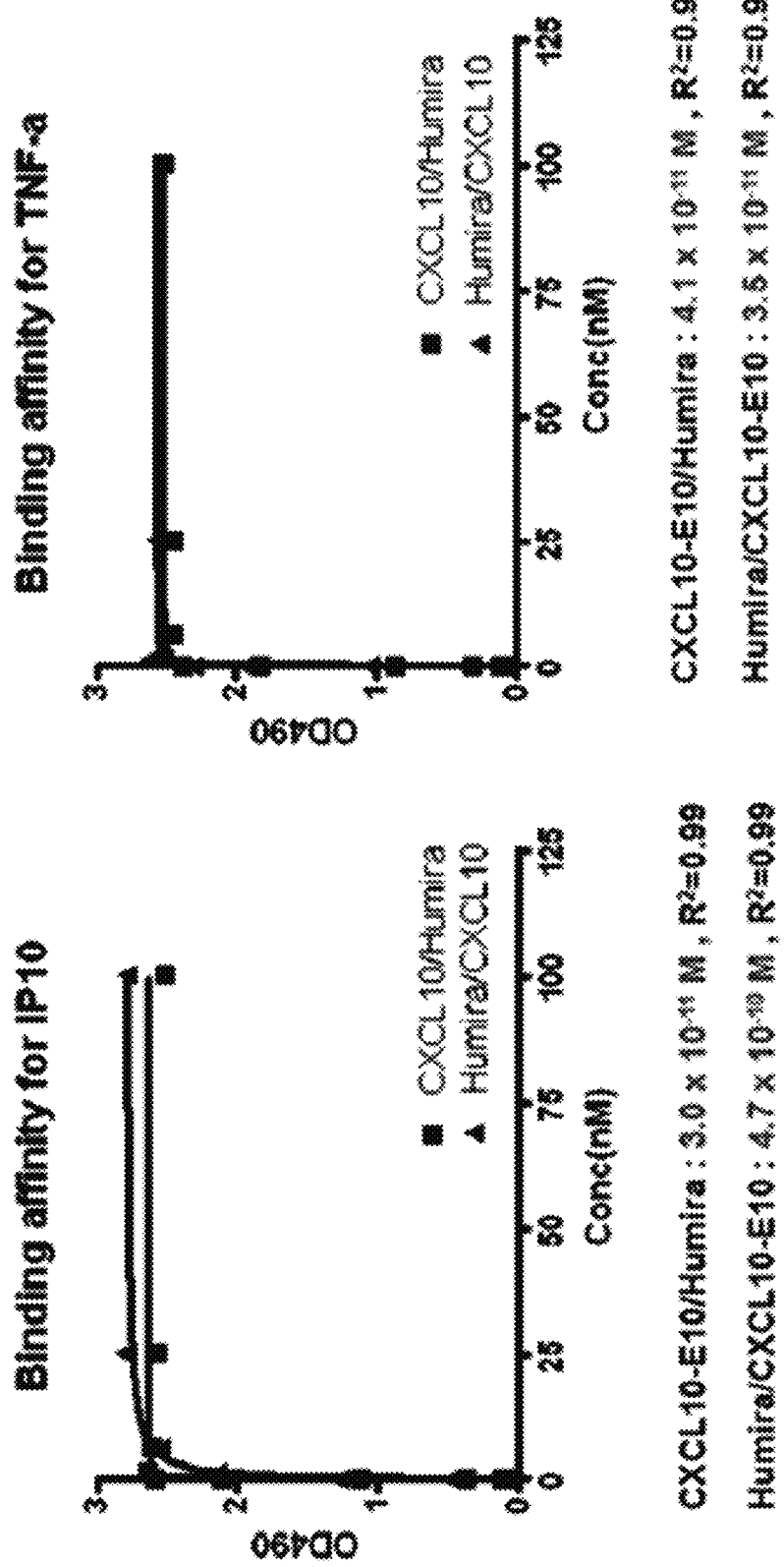
FIG. 7 shows a graph of a binding strength of the HuE10-101 bispecific antibody to an antigen.

Consequently, as shown in FIG. 7, it was seen that the HuE10-100 and HuE10-101 antibodies have the binding strengths to CXCL10 of $3.0 \times 10^{-11}$ M (R2=0.99) and $4.7 \times 10^{-10}$ M (R2=0.99), respectively, and the binding strengths to TNF-α of $4.1 \times 10^{-11}$ M (R2=0.989) and $3.5 \times 10^{-11}$ M (R2=0.99), respectively, and it was concluded that they have similar binding strengths to both of the antigens (FIG. 7).

5-3. Examination of Cytotoxicity of Bispecific Antibody, HuE10-101

For an animal test for the bispecific antibody, HuE10-101, cytotoxicity was investigated. 60.28 mg of the HuE10-101 was produced and investigated, and Humira was produced at 43.68 mg as a control group.

After the HuE10-101 was purified, to measure a bacterial endotoxin of the purified antibody, Chromo-LAL (cat# C0031, CAPE COD) was used. A control standard bacterial endotoxin (CSE; cat# E0005, CAPE COD) used as a control group was prepared by dilutions to reduce a concentration by one half of the previous concentration from 1 EU/ml to have a final concentration of 0.03125 EU/ml. A negative control was prepared by adding 100 µl of LAL to 100 µl of LAL reagent water (LRW, cat# WP1001, CAPE COD), and a positive control was prepared by mixing 100 µl of LAL with 100 µl of CSE having a concentration of 0.125 EU/ml before used in the experiment. For analysis, 100 µl of a sample diluted with LRW to have a uniform concentration of 50 µg/ml and 100 µl of the LAL were prepared. Additionally, a positive control test for a product was carried out to check interference of the sample, 50 µl of 0.125 EU/ml CSE and 100 µl of LAL were added to 50 µl of the diluted sample. A reference value was set using a file (Chromo LAL setting.pda) making it a protocol in measurement using a VersaMax microplate reader (Molecular devices). A plate was preheated at 37° C. for about 10 minutes before use in the experiment. An optical density (OD) was measured with treatment of LAL, starting from the file protocol. In the standard curve, the X axis represents log EU/ml, the Y axis represents log Onset time, and a cytotoxicity level of the sample was represented by automatically calculating the previously measured OD using software, in a unit of EU/ml. When the R2 value in the standard curve is 0.98 or higher, the measurement value was considered reliable.

Figure 8:
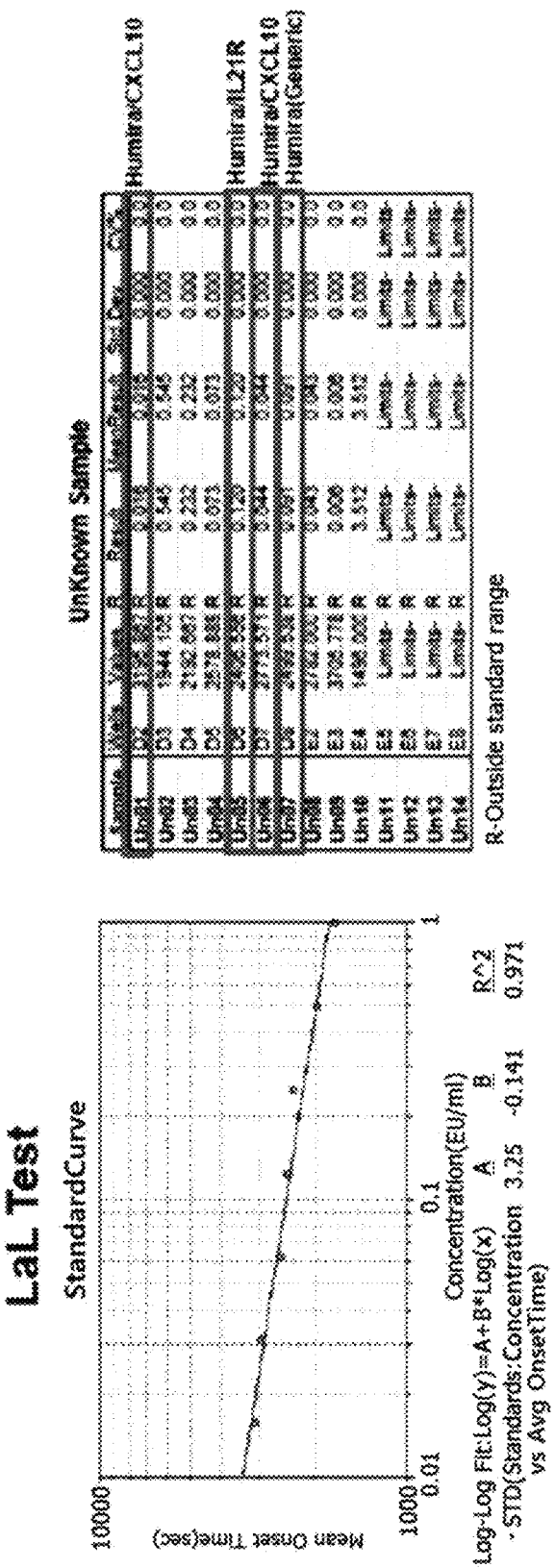
FIG. 8 shows a cytotoxicity of the purified HuE10-101 bispecific antibody.

Consequently, as shown in FIG. 8, it was seen that as the result of an LAL test carried out to check endotoxin levels of the HuE10-101 and Humira, LAL values of the HuE10-101 and Humira were all 0.1 EU/ml or less (FIG. 8).

Example 6: Establishment of HuE10-101 Producing Cell Line 6-1. Construction of HuE10-101 Expression Vector for Cell Line As a plasmid for expressing the heavy chain and light chain of the HuE10-101 antibody, a pOptiVec system (Invitrogen) was used. The advantage of the pOptiVec system is easy gene amplification since a gene of interest and a selection marker, DHFR, are present on the same transcriptome. Both of HuE10-101-Hc and HuE10-101-Lc were sub-cloned in the pOptivec vector, and the location of an enzyme used for DNA linearization in transfection was determined with PvuI in an ampicillin gene. A plasmid map is shown in FIG. 9. As a transfection reagent, lipofectamine 2000 was used, and ratios of DNA to lipofectamine 2000 were 1:1, 1.5 and 2.

6-2. Maintenance of CHO DG44

CHO DG44 cells used as an expression host were cultured using a MEM-α (w/)+10% FBS+AA medium. In cell passing, about 1 to $2 \times 10^6$ cells/well were detached from the bottom using 0.25% trypsin, 1/3 of the cells were transferred to a new well containing 2 ml of a medium. The development of a cell line was performed at the level of 96-well and 6-well plates.

6-3. Transfection

Cells were seeded in a 6-well plate at a density of $4 \times 10^5$ cells per well on the day before transfection, and cultured in an incubator for about 16 hours. On the day of transfection, a cell state was observed to be suitable for transfection, and the plate was washed with an MEM-α (w/) (-FBS, -AA) medium twice. 1 ml of the MEM-α (w/) (-FBS, -AA) medium was added, and cultured in an incubator for about 1 hour. DNAs required for the transfection were linearized HuE10-101-Hc and HuE10-101-Lc, and 2 µg of a mixture (Hc:1 μg+Lc:1 μg) and 4 μl of lipofectamine 2000 were mixed to 100 μl of the MEM-α (w/) (-FBS, -AA) to allow a reaction at room temperature for about 30 minutes at three ratios of DNA: lipofectamine 2000=1:1, 1.5 and 2. Herein, the ratio is 1:2. Transfection was carried out by dropping the mixture solution into a well, and the medium was exchanged with an MEM-α (w/)+10% FBS+AA medium 6 hours later. All the transfections were performed in multiples of 2.

Figure 10:
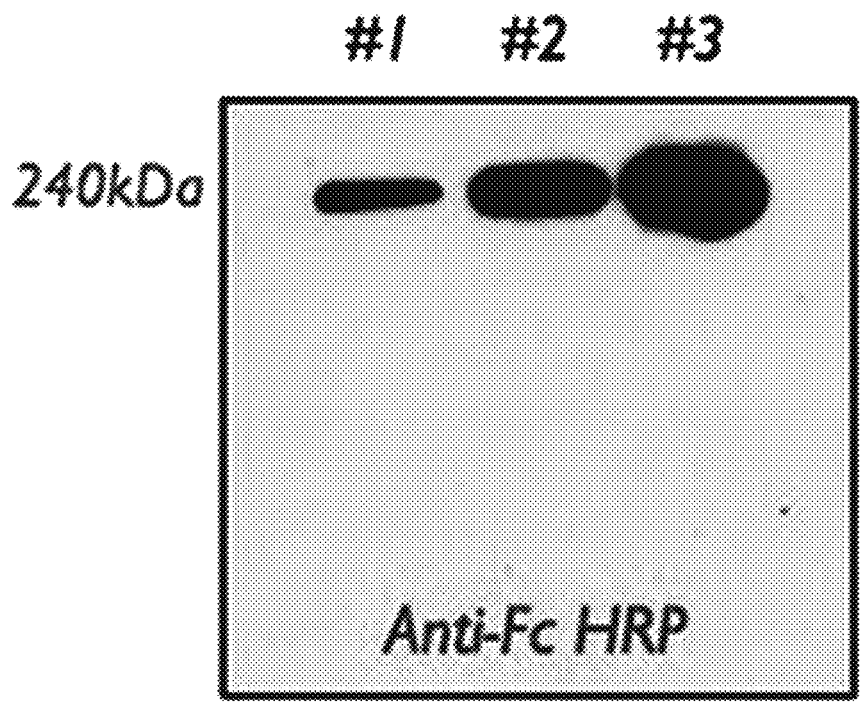
FIG. 10 shows a HuE10-101 expression level depending on a transfection condition.

To check if the transfection was well performed, western blotting was carried out. 2 to 3 days after the transfection, when cells filled in the 6-well plate, the medium was yielded, and western blotting was carried out. A 10% SDS PAGE gel was used, and 30 μl of the medium was loaded. It was confirmed that the transfection was most well performed under the condition of DNA: lipofectamine 2000=1:2 (FIG. 10).

6-4. Selection of Monoclones

Two days later, selection of monoclones was performed on 16 of 96-well plates of the transfected DG44s. All cells were detached with trypsin, counted, and seeded at a density of 200 cells per well. Here, for selection by DHFR, an MEM-α (w/o)+10% dFBS+AA medium was used. Two weeks later, generation of a colony was detected, and the medium was used to check a degree of expression of Hu10E-101 through ELISA. Therefore, 29 clones having a high expression rate were selected.

Figure 11:
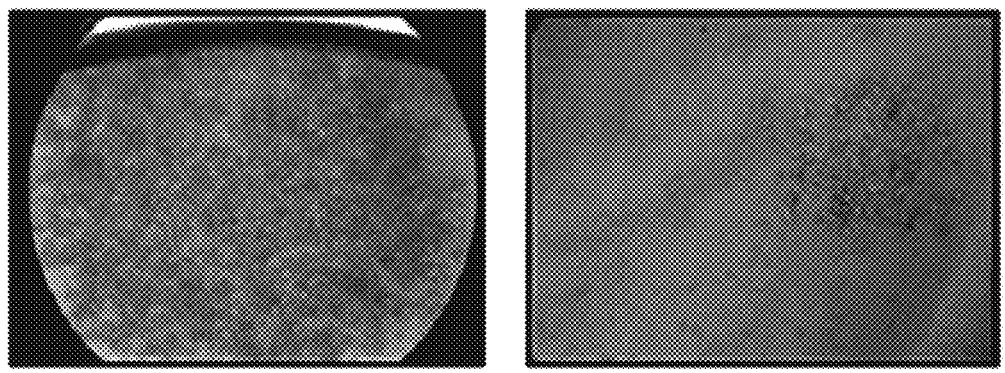
FIG. 11 is an image of a colony selected using DHFR.

FIG. 11 is a microscope image of colonies formed in the 96-well plate. For selection by DHFR, cell were seeded in 200 μl of MEM-α (w/o)+10% dFBS+AA at a density of 200 cells/well, and then transfected cells were grown in a selective medium, thereby forming colonies.

Figure 12:
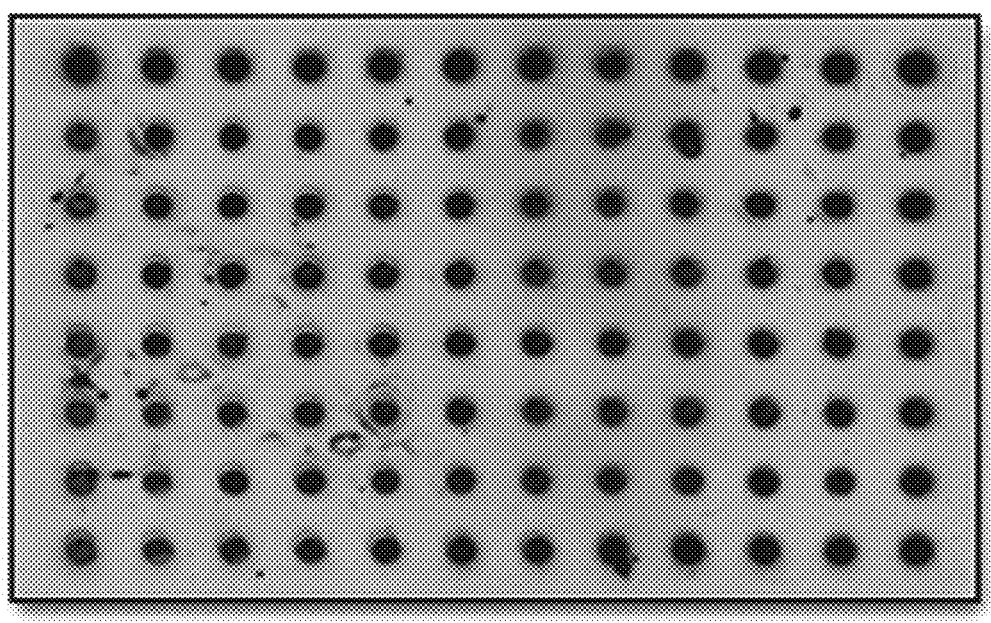
FIG. 12 shows a dot-blotting result to confirm HuE10-101 expression in a single clone selected using DHFR.

FIG. 12 is a dot-blotting result for checking colony expression. 30 μl of a medium was used, and probed with anti-Fc-HRP. It was seen that orange-circled clones having a high expression rate have stronger blots.

Figure 13:
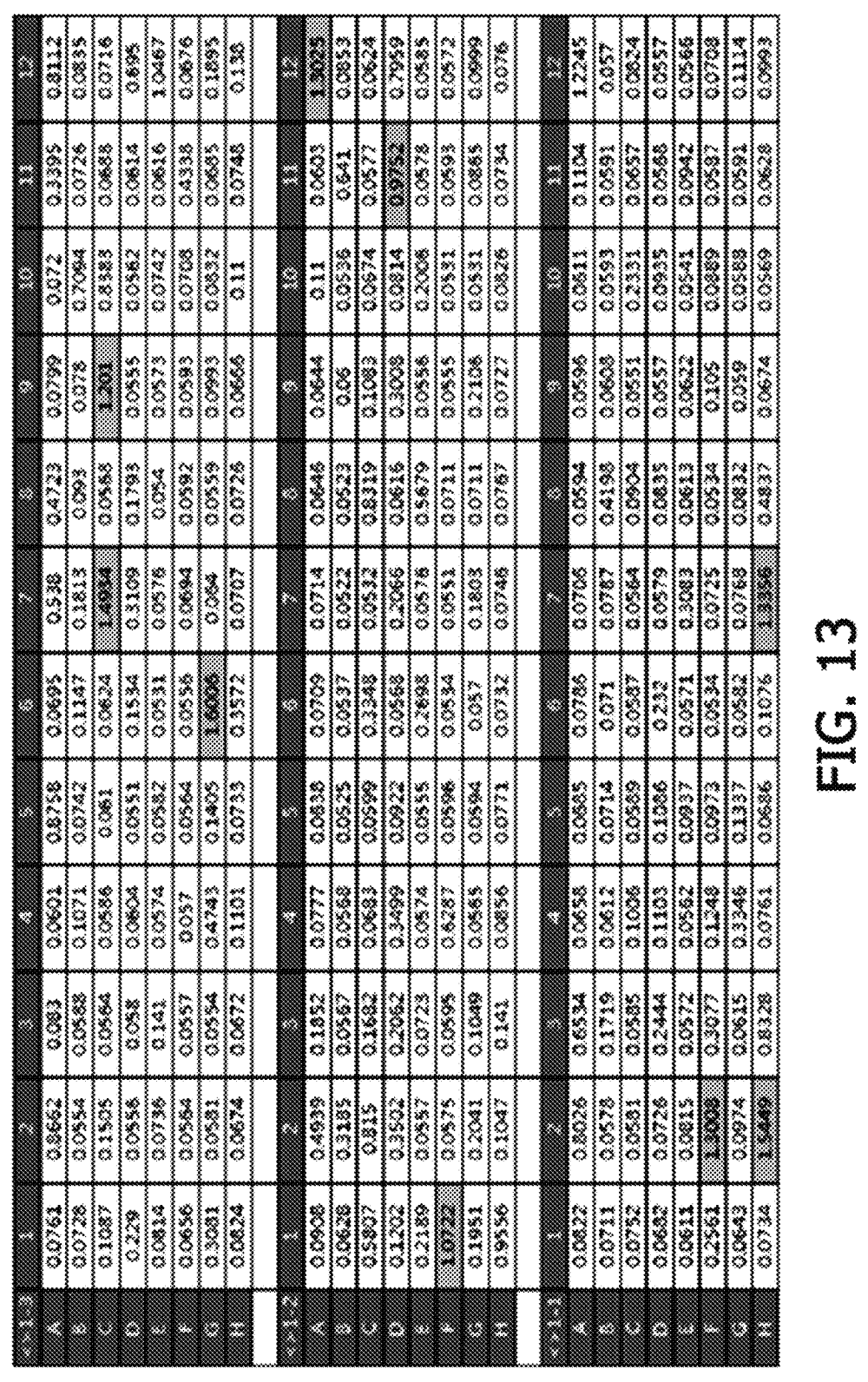

FIG. 13 shows relative expression levels, assessed by ELISA, for three of the 16 plates from which single clones were selected. An ELISA plate coated with anti-Fab antibodies at 100 ng/well was blocked with PBS containing 5% skim milk for 2 hours. Afterward, a colony-selected medium was yielded, and 100 μl of the medium was added to the plate. After a 2-hour reaction at room temperature, the plate was washed with 200 μl of 0.05% PBST three times, reacted with 100 μl of anti-Fc-HRPs in a ratio of 1:5,000 for 1 hour, and probed with OPD. Clones shown in purple are clones selected as having a relatively high expression rate.

Figure 14:
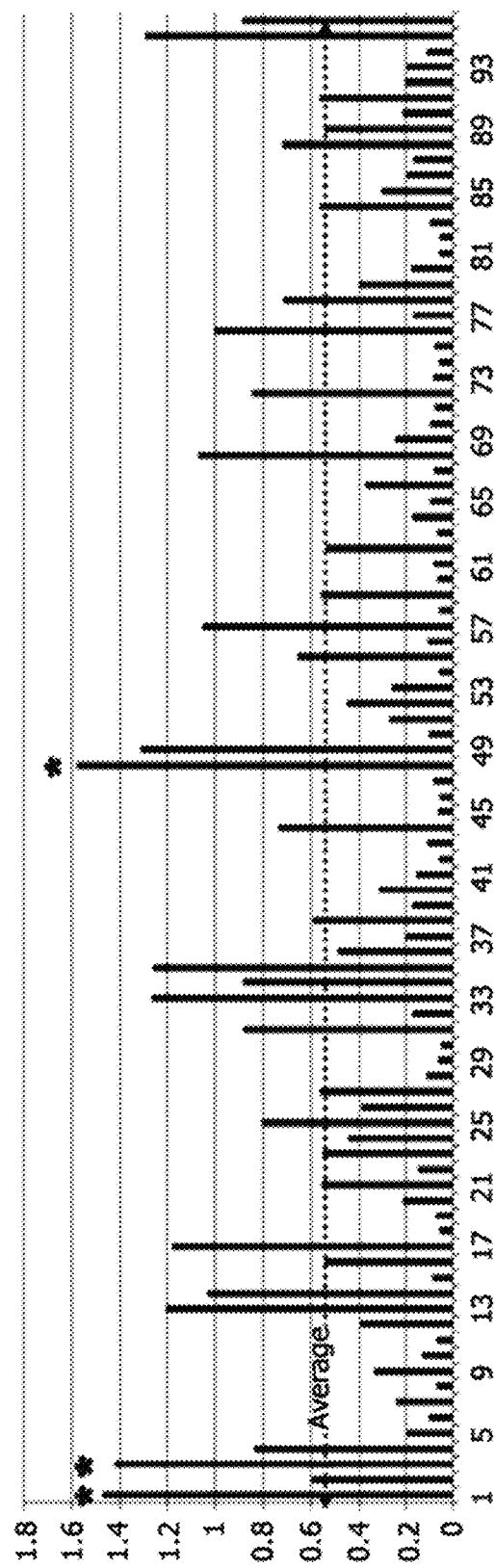
FIG. 14 is a graph showing 29 clones selected according to relatively high ELISA scores obtained from the result of FIG. 13.

Among the blots quantified by ELISA, 2 to 3 blots having a high expression level and a single colony were selected from one plate. The red dotted line shown in FIG. 14 indicates a mean value, and a colony shown as a red asterisk is the selected colony.

Figure 15:
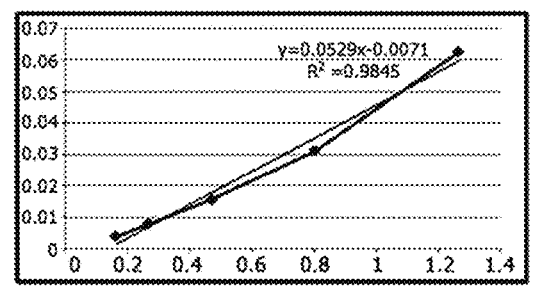
FIG. 15 shows HuE10-101 expression rates of clones transferred from 96 wells to ultimately 6 wells.

29 colonies having a high expression level were selected from the 16 plates by ELISA, and cells were amplified in 96 well in an order of 48 wells, 24 wells and 6 wells. When the cells were seeded in the final 6 wells at a density of $5 \times 10^5$ cells/well and fully grown, a medium was obtained and quantified by ELISA. Clones shown in red in FIG. 15 had a constant expression level even in the 6 wells, and gene amplification was performed with 100 nM MTX.

6-5. Gene Amplification

To amplify the expression of a HuE10-101 antibody, a MEM-α (w/o)+10% dFBS+AA medium to which MTX was added was used. Induction of adaptation started at an initial concentration of 100 nM. 29 previously selected HuE10-101 clones were dispensed at a density of $5 \times 10^5$ cells per well. At every third day, the medium was transferred to a fresh medium, and colony formation was observed. When the well was full, the cells were dispensed again into a new well plate at a density of $5 \times 10^5$ cells per well. After three passages of culture, an expression rate was assessed by ELISA. 1 μM of highly expressed clones among 100 nM of the reaction-completed clones were subjected to gene amplification.

FIG. 16 is a microscope image showing that colonies were formed a week after the cells were dispensed at an initial density of $5 \times 10^5$ cells per well. On every third day, the medium was replaced by a fresh medium, and colony formation was observed. When the plate was fully covered by the cells, the cells were detached with trypsin, and divided into a new plate. After three passages of culture, performed by the same method as described above, an expression rate was quantified by ELISA.

6-6. HuE10-101 Expression Rates of Reserve Cell Lines Selected at 100 nM

Quantification of the HuE10-101 antibody was carried out by the method of culturing cells adapted in each step under conditions of $5 \times 10^5$ cells/T-25 flask/5 ml for 6 days. Batch culturing was carried out with the cells adapted to 100 nM. The quantification of the antibody was carried out by ELISA.

Figure 17:
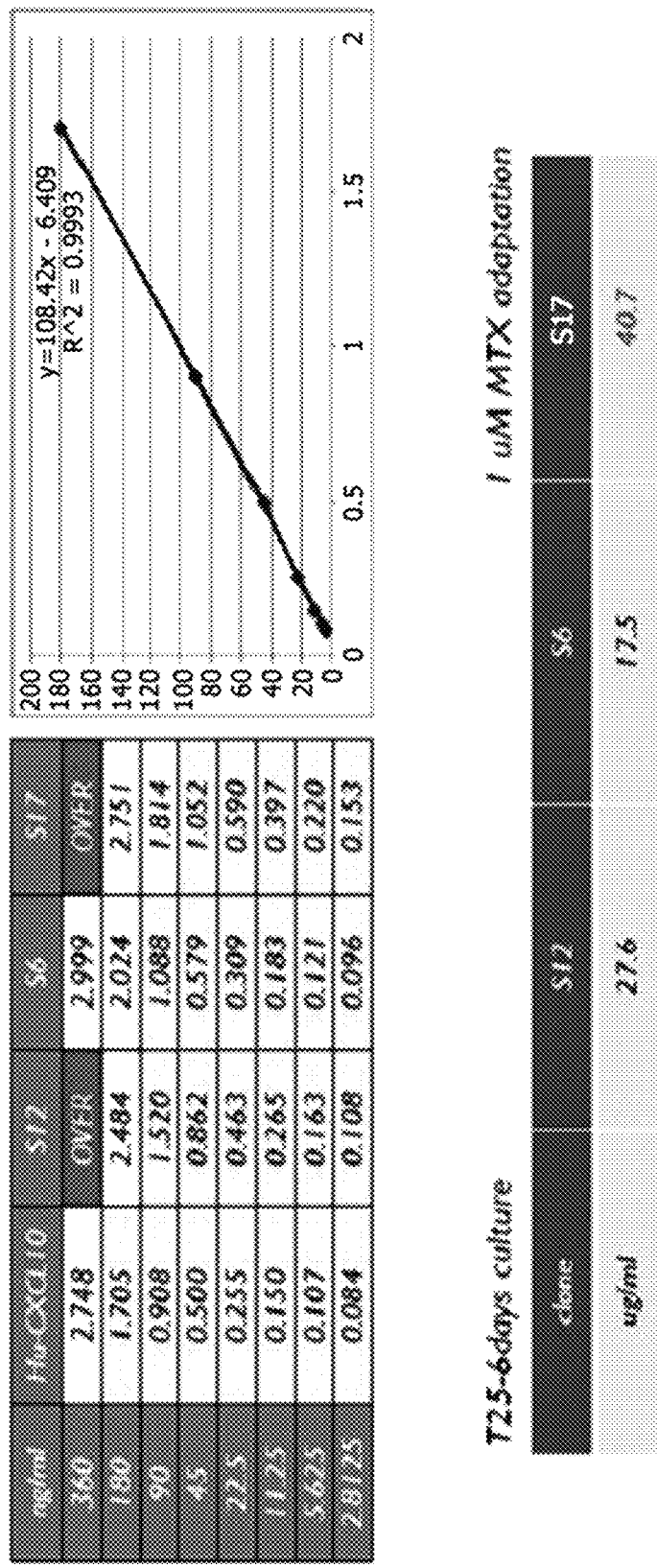
FIG. 17 shows HuE10-101 expression levels measured for three clones having high expression rates in 100 nM MTX.

In gene amplification at 100 nM, an adaptation rate varied depending on clones, and therefore, the three most rapidly growing clones were first dispensed into a T-25 flask by $5 \times 10^5$, and 6 days later, the medium was harvested, and quantification of the antibody was carried out by ELISA. The ELISA was carried out by the same method as described above. Consequently, it was seen that S17 clone exhibited the highest expression level of 40 mg/L. Therefore, the gene amplification of the S17 clone was induced with 1 μM MTX (FIG. 17).

6-7. Analysis of Protein Expression Level in Single Cell Line

Isolation of single cell lines were performed by a limiting dilution method using two types of cell groups (3 μM of Humira CXCL10 cell line S7, 4 μM of Humira CXCL10 cell line S7). To establish a single cell line, a cell line derived from single cells seeded in a 96-well plate at a density of 1 cell/well and formed a group was obtained. Expression levels of the obtained single cell lines were analyzed by ELISA using a cell culture obtained by culturing cells in a 24-well plate for 4 days, and a total of 20 single cell lines selected and listed in the following table were adapted to suspension culture in a 125 mL Erlenmeyer flask (Table 9).

TABLE 9

| Pool name | Single No. | μg/mL |
|---|---|---|
| S7 (3 μM) | 1 | 9.5 |
|  | 2 | 10.7 |
|  | 5 | 9.5 |
|  | 7 | 13 |
|  | 13 | 10.7 |
|  | 17 | 10.9 |
|  | 18 | 17.9 |
|  | 22 | 10.4 |
|  | 24 | 14 |
|  | 31 | 11.3 |
|  | 32 | 8.6 |
| S7 (4 μM) | 1 | 9.7 |
|  | 3 | 12.1 |
|  | 21 | 12.6 |
|  | 25 | 13.7 |
|  | 37 | 12.2 |
|  | 47 | 17.7 |
|  | 57 | 10.4 |

TABLE 9-continued

| Pool name | Single No. | µg/mL |
|---|---|---|
| | 69 | 14.9 |
| | 85 | 10.5 |

The selected 20 cell lines were adapted to suspended cells and resuspended in a chemically-defined medium to have a density of 5×cells/mL to be used in inoculation, and then 6-day fed-batch culture was carried out in a 34° C., 5% $CO_2$ incubator at a stirring rate of 140±10 rpm, followed by analyzing an expression level (Table 10).

TABLE 10

| No. | Sample | Productivity (µg/ml) |
|---|---|---|
| 1 | S7 (3 µM) - 2D6 | 66.58 |
| 2 | S7 (3 µM) - 7D6 | 64.19 |
| 3 | S7 (3 µM) - 18D6 | 73.46 |
| 4 | S7 (3 µM) - 24D6 | 64.28 |
| 5 | S7 (3 µM) - 31D6 | 70.68 |
| 6 | S7 (4 µM) - 3 D6 | 89.24 |
| 7 | S7 (4 µM) - 21 D6 | 85.22 |
| 8 | S7 (4 µM) - 25 D6 | 53.23 |
| 9 | S7 (4 µM) - 47 D6 | 64.6 |
| 10 | S7 (4 µM) - 69 D6 | 93.2 |

Figure 18:
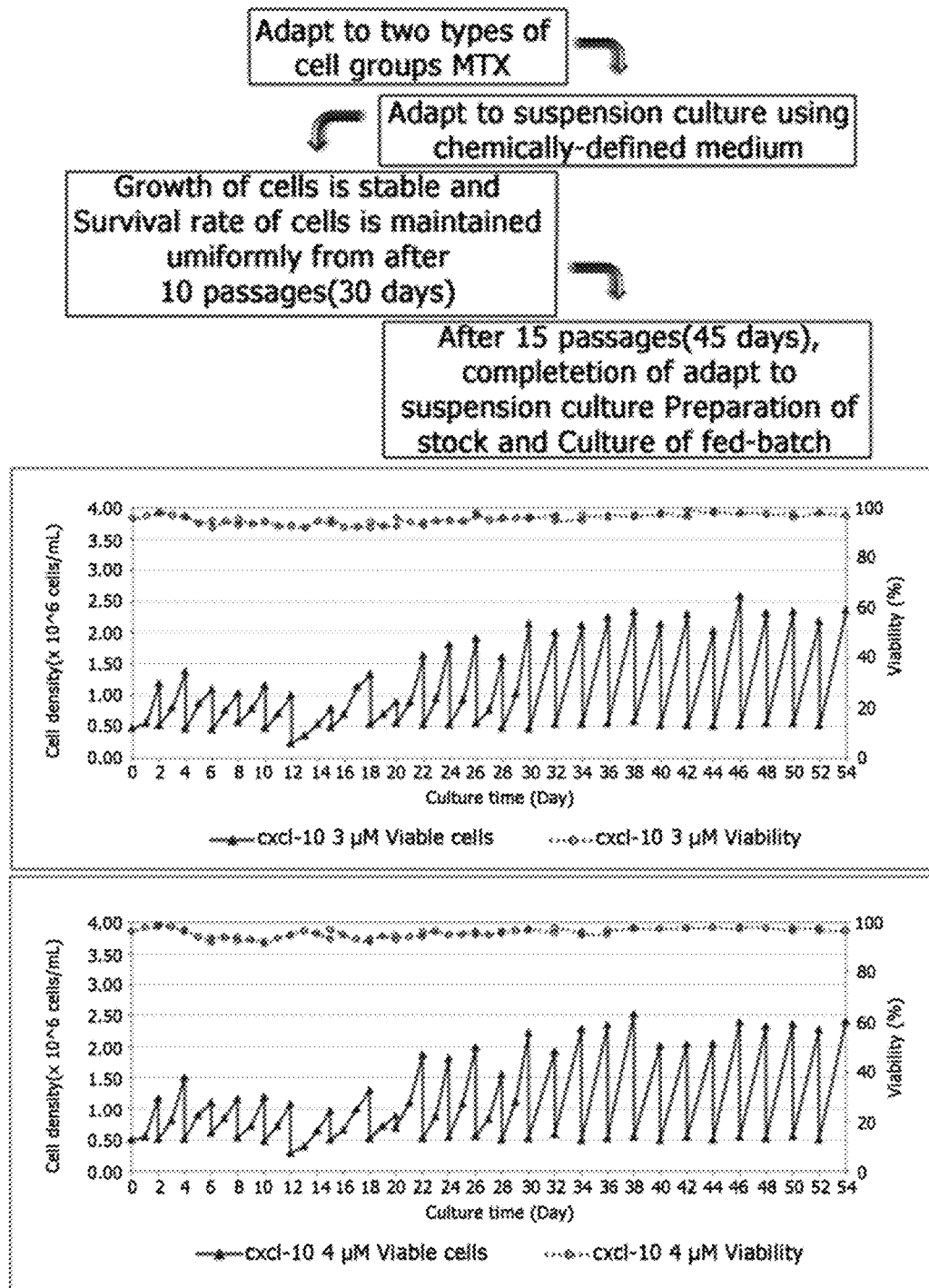
FIG. 18 shows culture stability.

6-8. Expression Stability of Antibody-Producing Cell Line 10 cell lines exhibiting an expression level of about 50 µg/mL or more by the analysis described in the previous step were selected, and cultured to confirm expression stability during long-term subculture. Frozen cells stored after adapted to suspension culture were defrosted in a chemically-defined medium and subcultured in a 125 mL Erlenmeyer flask every three days for 90 days. At every passage, a part of a cell culture was taken and frozen for storage, and stability was analyzed based on the result of the analysis of an expression level by ELISA. A cell line having a subculture maintained to 80% or more was selected as a cell line for process development. Based on the analysis result, a S7 (4 µM)-3 cell line was finally selected, and to confirm culture stability until 30 passages of the S7 (4 µM)-3 cell line, as a result of comparative analysis of mean expression levels between early stages of culturing (4 to 9 passages) and 26 to 30 passages, it was confirmed that the subculture stability was maintained 95% or more. Therefore, the S7 (4 µM)-3 cell line was used as a production cell line for process development and 10 g production (FIG. 18).

Example 7: Analysis of Physiochemical Property of Antibody 7-1. Analysis for Structure or Components of Antibody
7-1-1. Identification of N-Terminus Amino Acid Sequence Analysis of an N-terminus amino acid sequence was performed on each of a heavy chain and a light chain of an antibody protein.

When the first amino acid of the N-terminus sequence of a conventional antibody protein was glutamine, the amino acid, glutamine, was often modified with pyroglutamate. However, both the heavy chain and light chain of HuE10-101 consisted of glutamic acid and aspartic acid, not glutamine, and thus were less likely to having specific modification.

According to the analysis result, it was identified that the N-terminus sequence of the heavy chain had 16 amino acids, and the N-terminus sequence of the light chain had 18 amino acids. The identified amino acid sequence was equal to a theoretical amino acid sequence.

The HuE10-101 sample was precipitated with TCA to remove a storage buffer, and denatured by treatment with 5 M urea. The antibody was cleaved into peptide fragments by trypsin treatment, and deglycosylated by adding PNGase-F. Finally, DTT was added to remove a disulfide bond, and then a peptide analysis experiment was carried out with LC-MS. The N-terminus sequence of the antibody protein is highly likely to have post-translational modification (PTM), compared to an amino acid of a different part during the expression of a protein, and may be associated to activity of the antibody protein and other immune rejections. The HuE10-101 is structurally divided into a heavy chain and a light chain, and in the present experiment, final sequencing was performed on each of the N-terminus of the heavy chain and the N-terminus of the light chain by LC-MS/MS. For the N-terminus analysis, the N-terminus of the heavy chain and the N-terminus of the light chain were analyzed with trypsin.

Figure 19A:
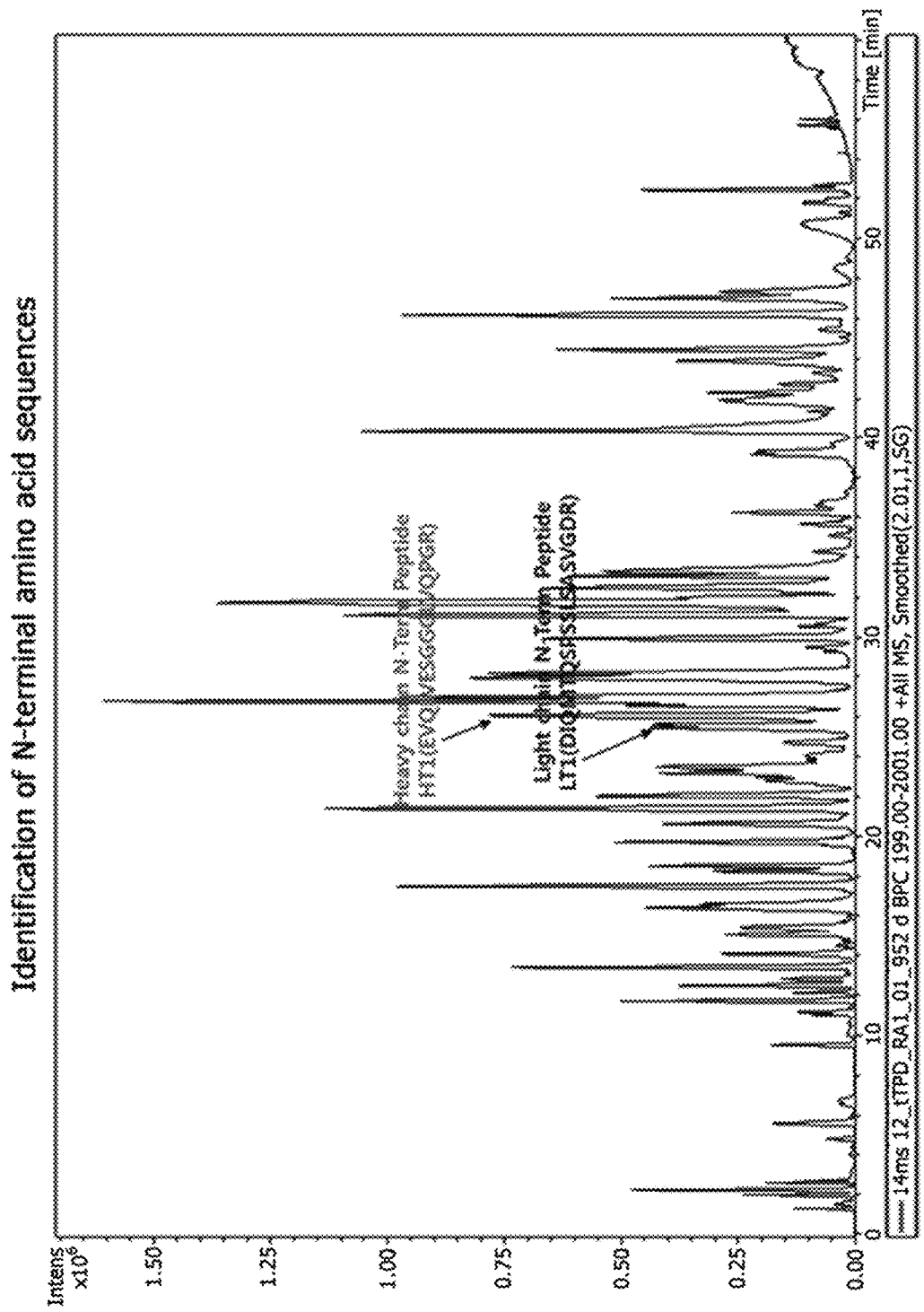
FIG. 19 shows an N-terminal amino acid sequence of HuE10-101.
Figure 19B:
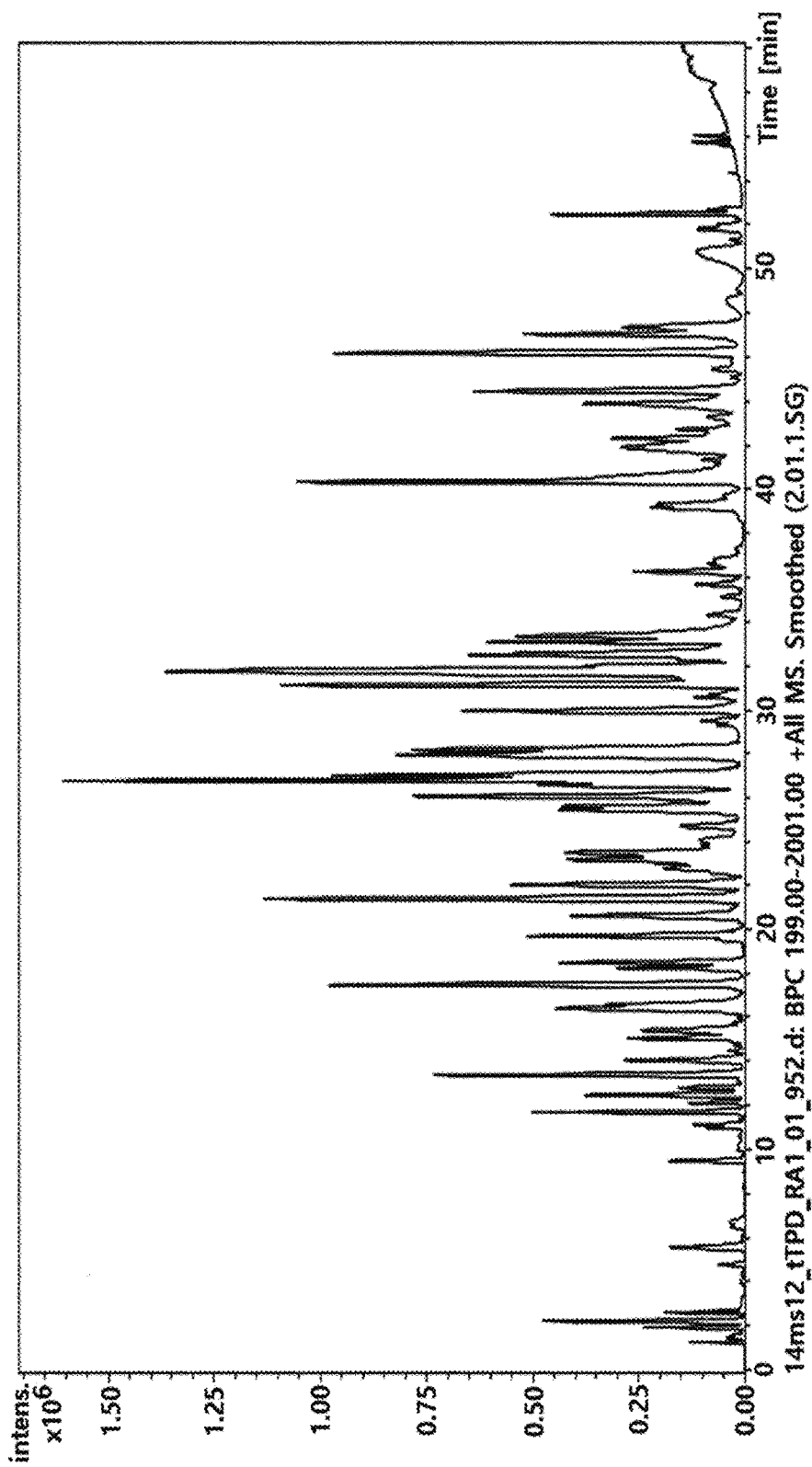

The antibody-derived peptides cleaved with trypsin were subjected to LC-MS peptide mapping and LC-MS/MS sequencing analysis, and an N-terminus peptide was identified by calculating a theoretical peptide molecular weight (FIG. 19A).

Figure 19C:
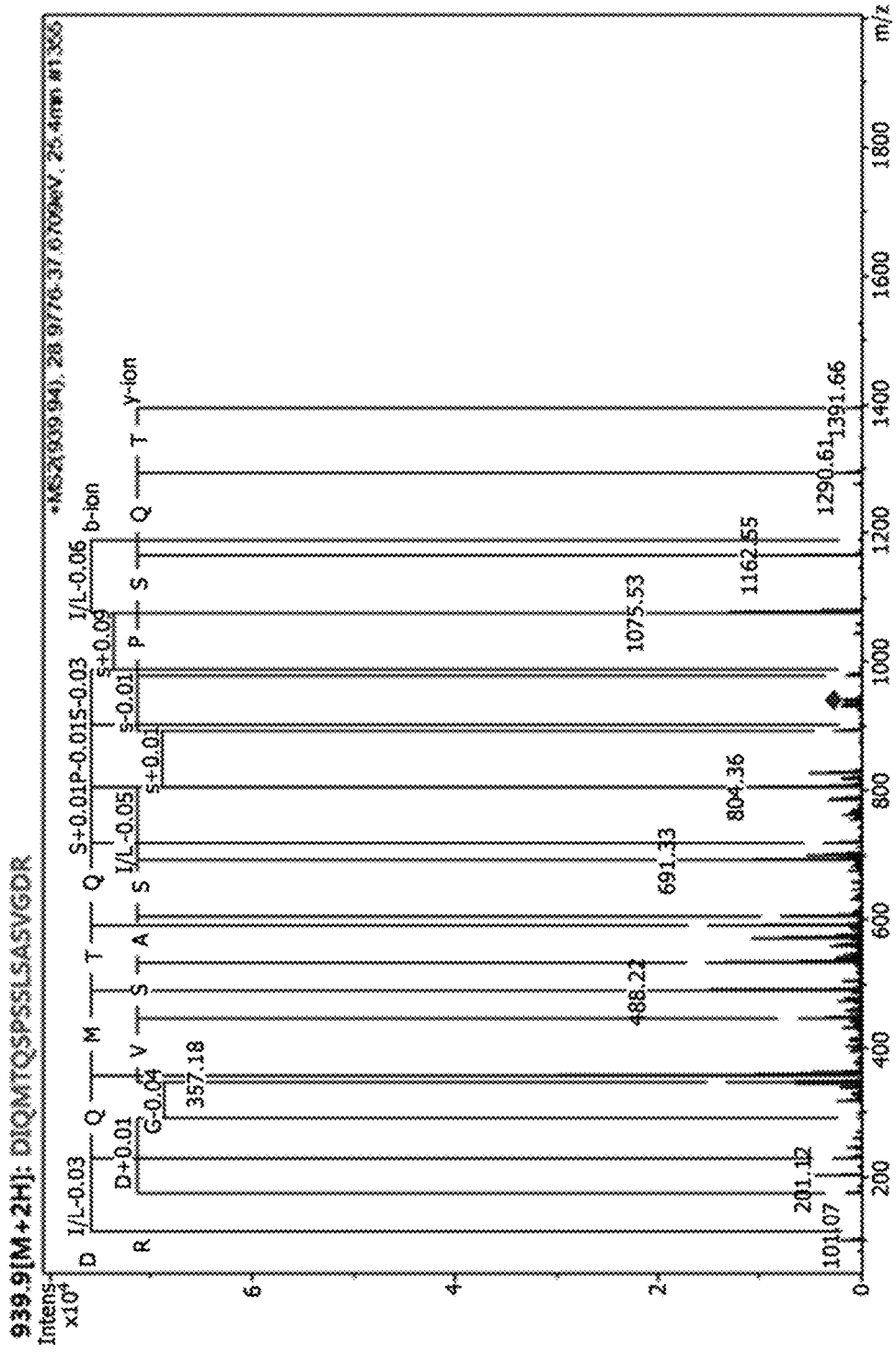
Figure 19D:
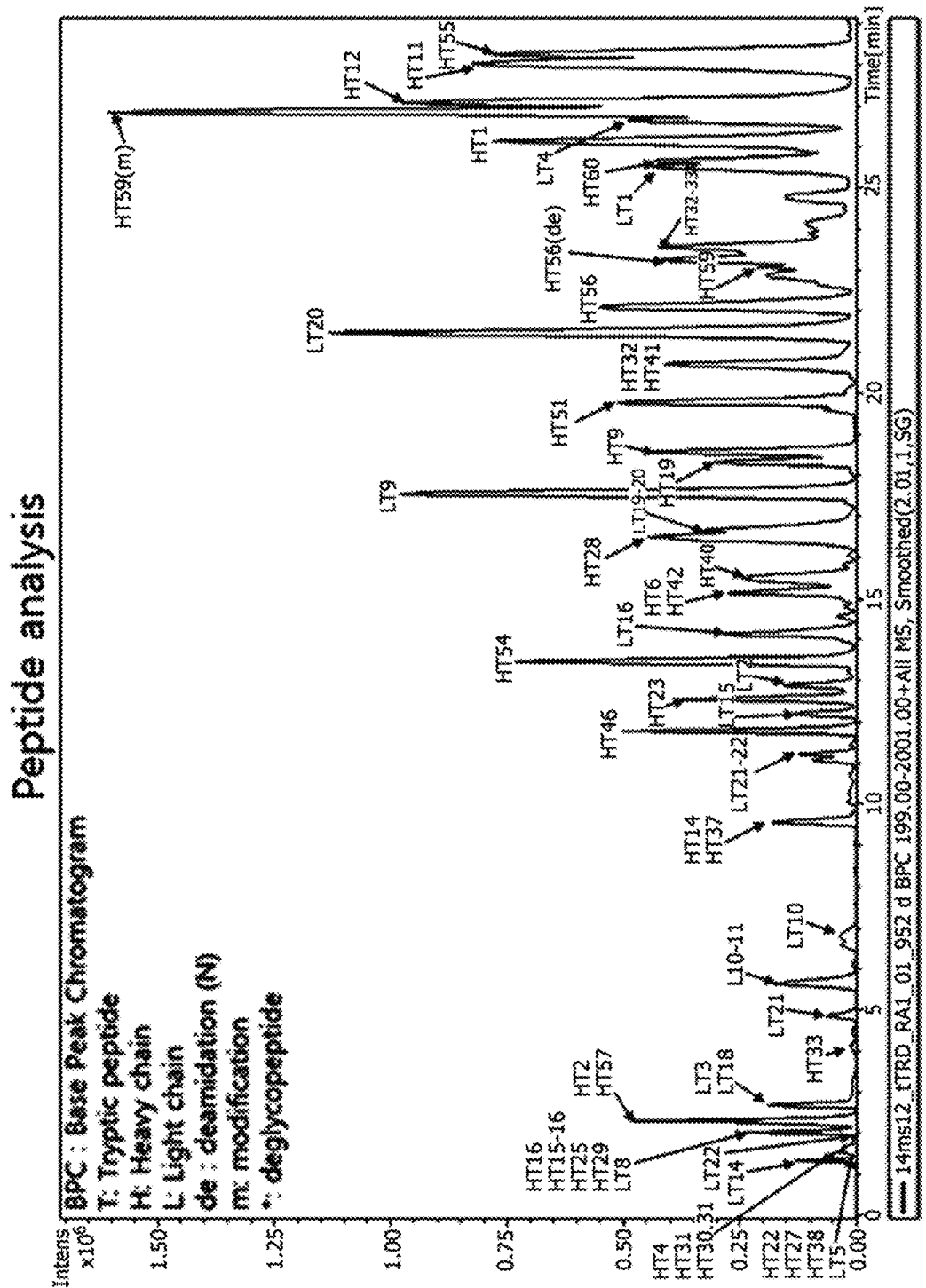
Figure 19E:
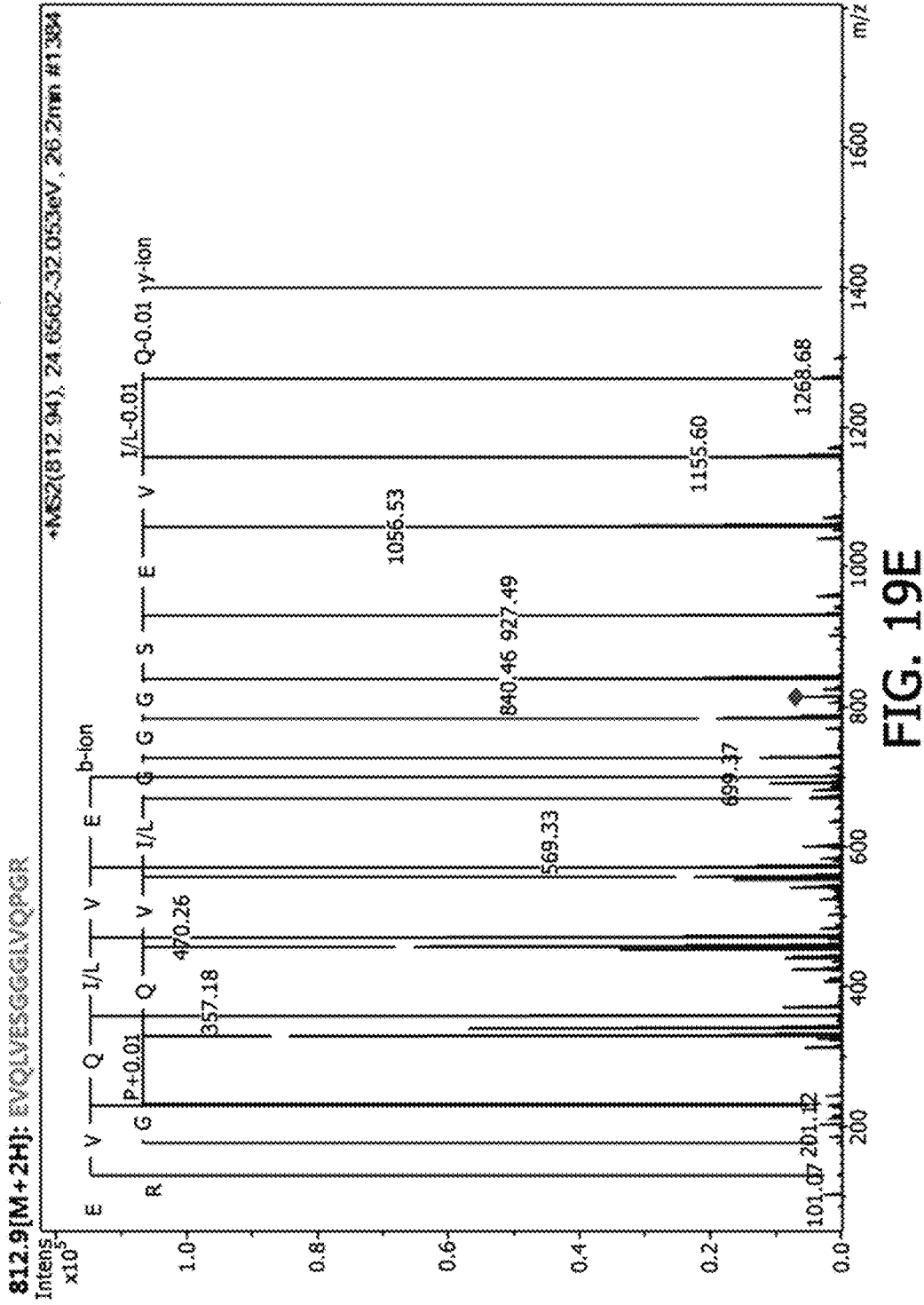
Figure 19F:
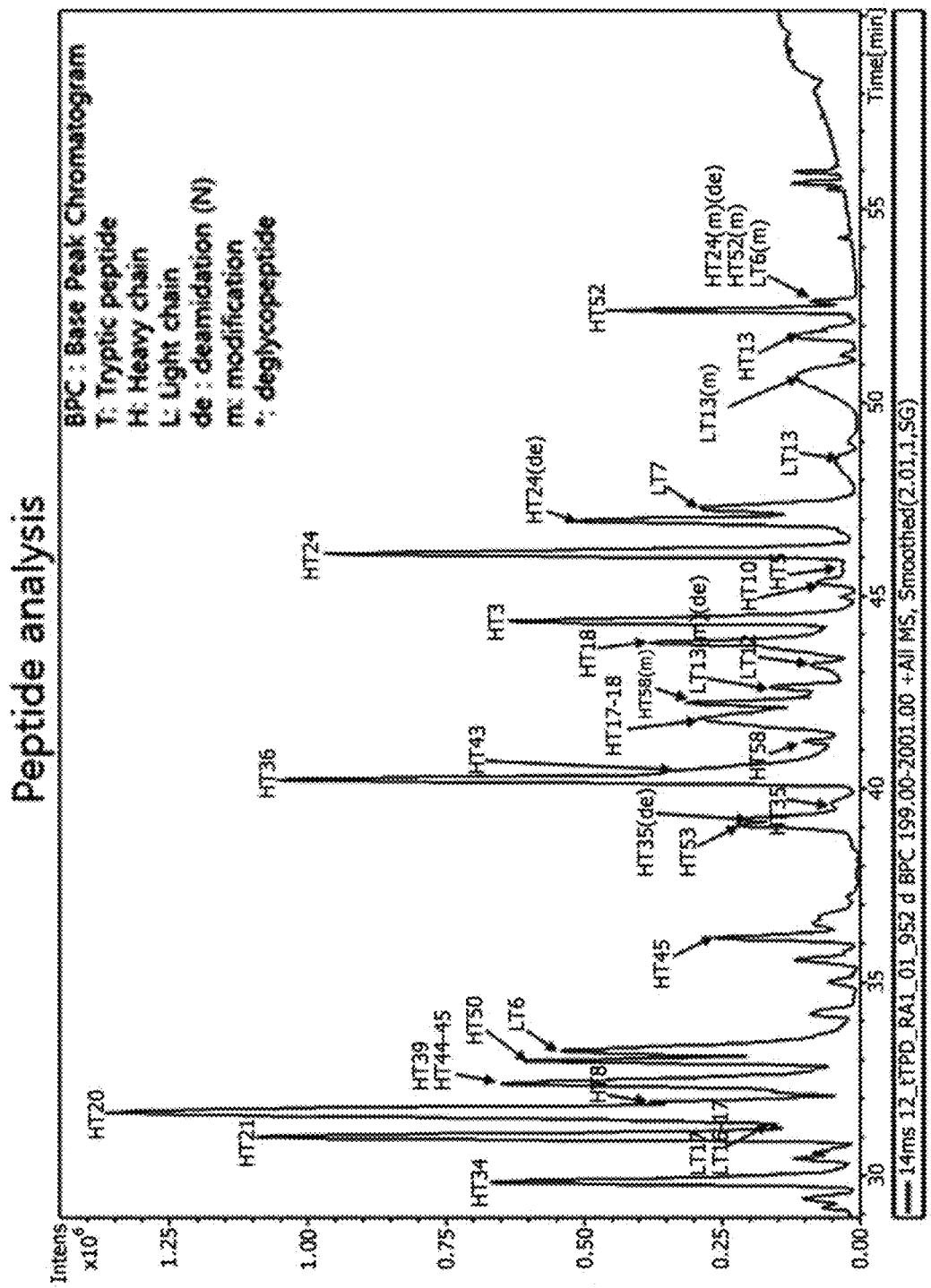

A retention time of the corresponding peptide was checked by previously performing LC-MS under the same condition, and peptide sequencing was performed by LC-MS/MS analysis under an LC condition. FIGS. 19A and 19C show the N-terminus sequencing results for the heavy chain and light chain of HuE10-101 by LC-MS/MS analysis. Consequently, the N-terminus sequences of the heavy chain and light chain of the HuE10-101 protein were sequenced with the N-terminus sequence of a theoretical HuE10-101 protein having the same peptide molecular weight, and the N-terminus sequence of the heavy chain was identified as EVQLVESGGGLVQPGR, and the N-terminus sequence of the light chain was identified as DIQMTQSPSSLSAS-VGDR (FIG. 19).

Table 11 shows the summary of theoretical molecular weights of the N-terminus sequences, molecular weights observed by LC-MS and N-terminus sequences identified by MS/MS sequencing. A pyrrolidone carboxylic acid form, which is a modified form of the N-terminus of a conventional protein, and modifications such as cleavage, deamidation and oxidation were not found in the HuE10-101 protein (Table 11).

TABLE 11

| Frag# | Res# | Theoretical mass (TPD) | | | Observed mass (LC-MS) | Charge | Sequencing |
|---|---|---|---|---|---|---|---|
| | | M + H | M + 2H | M + 3H | | | |
| HT1 | 1-16 | 1624.87 | 812.94 | 542.29 | 812.91 | 2 | EVQLVESGGGLVQPGR (residues 1 to 16 of SEQ ID NO: 4) |
| LT1 | 1-18 | 1878.89 | 939.95 | 626.97 | 939.92 | 2 | DIQMTQSPSSLSASVGDR (residues 1 to 18 of SEQ ID NO: 8) |

HT: Heavy chain tryptic peptide
LT: Light chain tryptic peptide

According to the results shown in the above table, through HuE10-101 N-terminus sequencing, the N-terminus sequence of the heavy chain was identified as EVQLVES-GGGLVQPGR (residues 1 to 16 of SEQ ID NO: 4), and the N-terminus sequence of the light chain was identified as DIQMTQSPSSLSASVGDR (residues 1 to 18 of SEQ ID NO: 8), and therefore no specific modification was found.

7-1-2. Peptide Analysis

To investigate the morphological characteristic of HuE10-101, after protease (trypsin) treatment, the identity of a theoretical amino acid sequence was analyzed by LC-MS peptide mapping.

The HuE10-101 was identified as the sequence having 98% or more identity to a predicted theoretical amino acid sequence of the protein. Modification occurred at some amino acids due to a chemical bond, but it was found in a very small amount that can be observed in the experiment and analysis processes.

The HuE10-101 sample was precipitated with TCA to remove a storage buffer, and denatured by treatment with 5 M urea. Subsequently, the antibody was cleaved into peptide fragments by trypsin treatment, and deglycosylated by adding PNGase-F. Finally, DTT was added to remove a disulfide bond, and then the peptide was analyzed with LC-MS.

The HuE10-101 is a macroprotein, which has a total molecular weight of about 190 kDa and consists of a heavy chain and a light chain. HuE10-101 is comprised of 919 amino acids in total, with heavy chain and light chain each being consisted of 705 and 214 amino acids, respectively (SEQ ID NOs: 59 and 60). A conventional antibody protein has a molecular weight of 150 kDa, but in the HuE10-101 protein, a heavy chain variable domain sequence was additionally linked behind C-terminal 451 lysine of the heavy chain.

For analyses of morphological characteristics of the heavy chain/light chain of the HuE10-101 protein, the HuE10-101 protein sequence was analyzed by measuring the consistency of the mass of a corresponding peptide based on the theoretical molecular weight of the peptide cleaved by the protease and a peptide peak-assigned peptide molecular weight obtained from an LC-MS chromatography profile of the actual HuE10-101 protein. FIG. 20 is a peptide mapping result for the analysis sample, HuE10-101, which is an LC-MS chromatogram obtained by elution of a tryptic peptide derived from the HuE10-101 antibody.

Figure 20A:
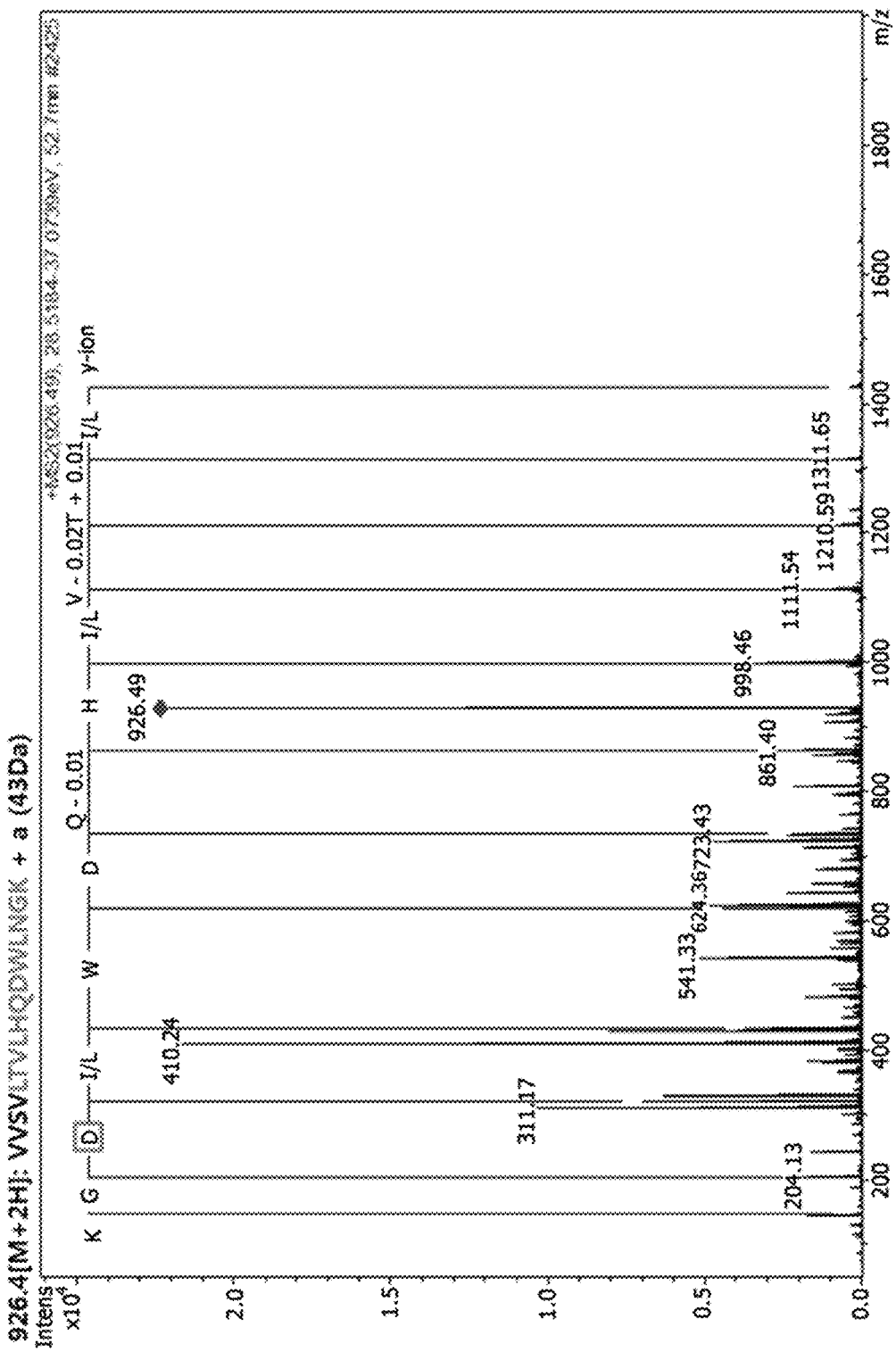
FIG. 20 is a peptide mapping result for HuE10-101.
Figure 20B:
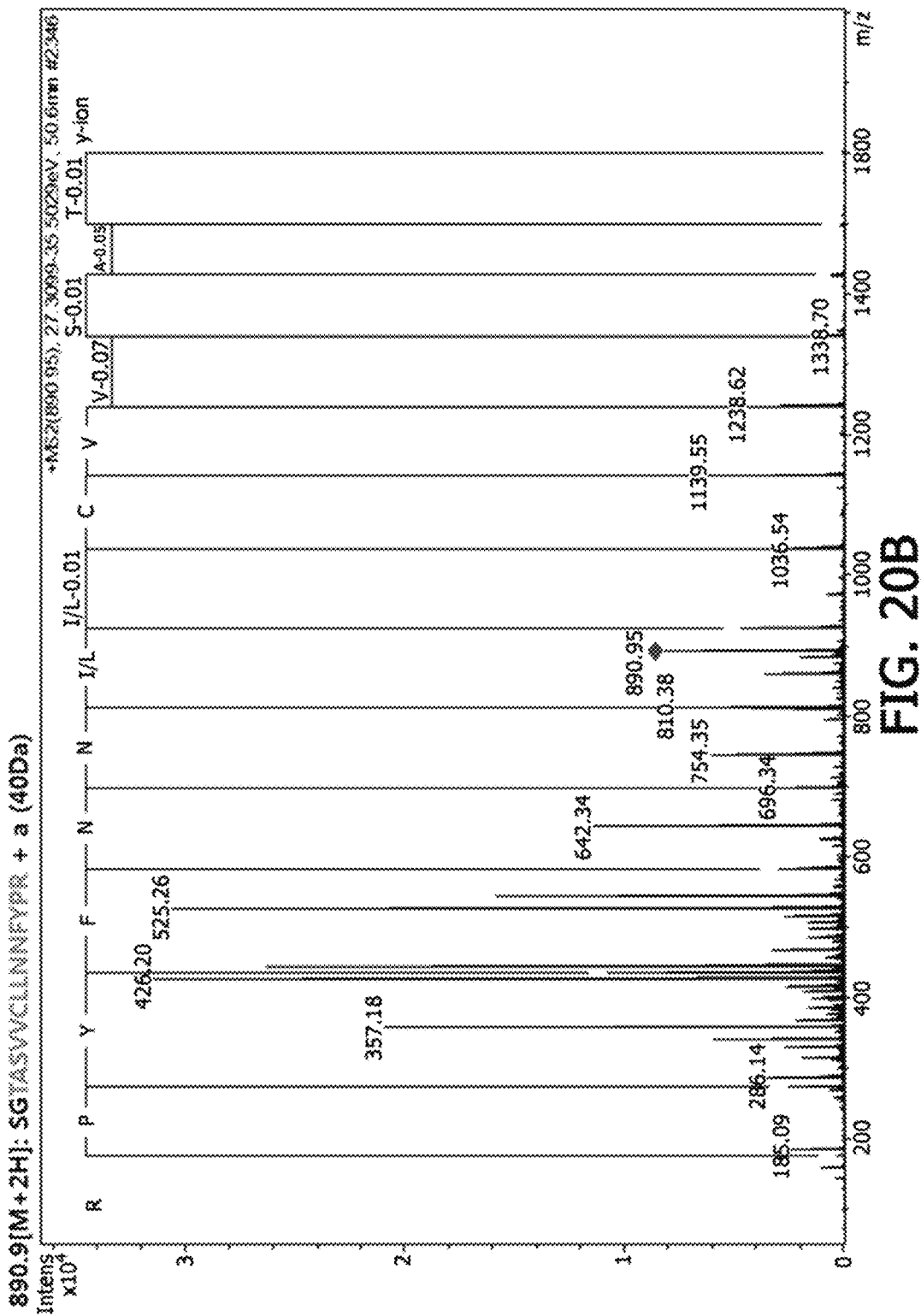

Since the number of the HuE10-101 protein-derived peptides was large, peptide peak assignment results are shown in FIGS. 20A and 20B depending on elution time points.

A theoretical molecular weight of a tryptic peptide in the heavy chain and light chain sequences of the HuE10-101 antibody protein, the molecular weight of the peptide detected in the LC-MS chromatogram and the sequencing result are summarized. Through the peptide mapping using trypsin, 1.9% of the antibody protein sequence was not identified. This is because, when the protein was cleaved with a protease, the cleaved peptide is very small or a very weak signal of the specific peptide was detected. Also, when the antibody protein had unpredictable post-translational modification (PTM), it was impossible to detect the sequence only with the mass. Such an unpredictable peptide was finally identified by peptide sequencing using LC-MS/MS. In Tables 16 and 17, a peptide having a difference from the theoretical molecular weight of the tryptic peptide was able to be identified, and 7 modified peptides were found in the heavy chain, and three modified peptides in the light chain. Identification of modified peptides shown in Tables 12 and 13 was carried out by LC-MS/MS, and thereby a change in sequence was observed by final de-novo sequencing. As a result, in both of the heavy chain and the light chain, deamination at an asparagine amino acid and binding of some compounds thereto were also observed.

TABLE 12

| Frag# | Res# | Theoretical mass(TPD) | | | | | Observed mass (LC-MS) | Charge |
|---|---|---|---|---|---|---|---|---|
| | | M + H | M + 2H | M + 3H | M + 4H | M + 5H | | |
| HT1 | 1-16 | 1624.87 | 812.94 | 542.29 | 406.97 | 325.78 | 812.91 | 2 |
| HT2 | 17-19 | 375.24 | 188.12 | 125.75 | 94.56 | 75.85 | 375.22 | 1 |
| HT3 | 20-38 | 2176.96 | 1088.98 | 726.32 | 545.00 | 436.20 | 726.30 | 3 |
| HT4 | 39-43 | 500.28 | 250.65 | 167.43 | 125.83 | 100.86 | 500.26 | 1 |
| HT5 | 44-67 | 2662.25 | 1331.63 | 888.09 | 666.32 | 533.26 | 888.08 | 3 |
| HT6 | 68-72 | 623.35 | 312.18 | 208.46 | 156.59 | 125.48 | 623.33 | 1 |
| HT7 | 73-76 | 447.22 | 224.11 | 149.75 | 112.56 | 90.25 | N.D | |
| HT8 | 77-87 | 1338.68 | 669.85 | 446.90 | 335.43 | 268.54 | 669.82 | 2 |
| HT9 | 88-98 | 1233.55 | 617.28 | 411.85 | 309.14 | 247.52 | 617.26 | 2 |
| HT10 | 99-125 | 2808.39 | 1404.70 | 936.80 | 702.85 | 562.49 | 936.77 | 3 |
| HT11 | 126-137 | 1186.65 | 593.83 | 396.22 | 297.42 | 238.14 | 593.81 | 2 |

TABLE 12-continued

| Frag# | Res# | Theoretical mass(TPD) | | | | | Observed mass (LC-MS) | Charge |
|---|---|---|---|---|---|---|---|---|
| | | M + H | M + 2H | M + 3H | M + 4H | M + 5H | | |
| HT12 | 138-151 | 1264.66 | 632.83 | 422.22 | 316.92 | 253.74 | 632.81 | 2 |
| HT13 | 152-214 | 6656.29 | 3328.65 | 2219.44 | 1664.83 | 1332.06 | 1332.03 | 5 |
| HT14 | 215-217 | 361.21 | 181.11 | 121.07 | 91.06 | 73.05 | 361.19 | 1 |
| HT15 | 218-218 | 175.12 | 88.06 | 59.05 | 44.54 | 35.83 | — | |
| HT16 | 219-222 | 472.28 | 236.64 | 158.10 | 118.83 | 95.26 | 472.26 | 1 |
| HT15-16 | 218-222 | 628.38 | 314.69 | 210.13 | 157.85 | 126.48 | 314.68 | 2 |
| HT17 | 223-226 | 452.18 | 226.59 | 151.40 | 113.80 | 91.24 | N.D | |
| HT18 | 227-252 | 2730.42 | 1365.71 | 910.81 | 683.36 | 546.89 | 683.34 | 4 |
| HT17-18 | 223-252 | 3163.58 | 1582.29 | 1055.20 | 791.65 | 633.52 | 791.62 | 4 |
| HT19 | 253-259 | 835.43 | 418.22 | 279.15 | 209.61 | 167.89 | 418.21 | 2 |
| HT20 | 260-278 | 2082.01 | 1041.51 | 694.67 | 521.26 | 417.21 | 694.65 | 3 |
| HT21 | 279-292 | 1677.80 | 839.41 | 559.94 | 420.21 | 336.37 | 559.92 | 3 |
| HT22 | 293-296 | 501.31 | 251.16 | 167.78 | 126.08 | 101.07 | 501.29 | 1 |
| HT23 | 297-305 | 1189.51 | 595.26 | 397.18 | 298.13 | 238.71 | — | |
| HT23* | 297-305 | 1190.51 | 595.76 | 397.50 | 298.38 | 238.90 | 595.73 | 2 |
| HT24 | 306-321 | 1808.01 | 904.51 | 603.34 | 452.76 | 362.41 | 603.32 | 3 |
| HT24(de) | 306-321 | 1809.01 | 905.01 | 603.67 | 453.00 | 362.60 | 603.65 | 3 |
| HT24(m)(de) | 306-321 | 1851.80 | 926.40 | 617.93 | 463.70 | 371.16 | 926.40 | 2 |
| HT25 | 322-324 | 439.22 | 220.11 | 147.08 | 110.56 | 88.65 | 439.20 | 1 |
| HT26 | 325-326 | 250.12 | 125.57 | 84.05 | 63.29 | 50.83 | — | |
| HT27 | 327-330 | 447.26 | 224.13 | 149.76 | 112.57 | 90.26 | 447.24 | 1 |
| HT28 | 331-338 | 838.50 | 419.76 | 280.17 | 210.38 | 168.51 | 419.74 | 2 |
| HT29 | 339-342 | 448.28 | 224.64 | 150.10 | 112.83 | 90.46 | 448.26 | 1 |
| HT30 | 343-344 | 218.15 | 109.58 | 73.39 | 55.29 | 44.44 | — | |
| HT31 | 345-348 | 457.25 | 229.13 | 153.09 | 115.07 | 92.26 | 457.23 | 1 |
| HT30-31 | 343-348 | 656.38 | 328.70 | 219.47 | 164.85 | 132.08 | 656.36 | 1 |
| HT32 | 349-359 | 1286.67 | 643.84 | 429.56 | 322.42 | 258.14 | 643.82 | 2 |
| HT33 | 360-364 | 605.31 | 303.16 | 202.44 | 152.08 | 121.87 | 605.29 | 1 |
| HT32-33 | 349-364 | 1872.97 | 936.99 | 625.00 | 469.00 | 375.40 | 624.97 | 3 |
| HT34 | 365-374 | 1104.61 | 552.81 | 368.87 | 276.91 | 221.73 | 552.79 | 2 |
| HT35 | 375-396 | 2544.13 | 1272.57 | 848.72 | 636.79 | 509.63 | 848.69 | 3 |
| HT35(de) | 375-396 | 2545.13 | 1273.07 | 849.04 | 637.03 | 509.83 | 1273.01 | 2 |
| HT36 | 397-413 | 1873.92 | 937.47 | 625.31 | 469.24 | 375.59 | 937.44 | 2 |
| HT37 | 414-418 | 575.34 | 288.17 | 192.45 | 144.59 | 115.87 | 575.32 | 1 |
| HT38 | 419-420 | 262.15 | 131.58 | 88.06 | 66.29 | 53.24 | 262.14 | 1 |
| HT39 | 421-443 | 2744.25 | 1372.63 | 915.42 | 686.82 | 549.66 | 686.79 | 4 |
| HT40 | 444-451 | 788.45 | 394.73 | 263.49 | 197.87 | 158.50 | 394.72 | 2 |
| HT41 | 452-467 | 1608.88 | 804.95 | 536.97 | 402.98 | 322.58 | 804.92 | 2 |
| HT42 | 468-470 | 375.24 | 188.12 | 125.75 | 94.56 | 75.85 | 375.22 | 1 |
| HT43 | 471-489 | 2133.96 | 1067.49 | 711.99 | 534.25 | 427.60 | 711.97 | 3 |
| HT44 | 490-494 | 500.28 | 250.65 | 167.43 | 125.83 | 100.86 | N.D | |
| HT45 | 495-509 | 1621.79 | 811.40 | 541.27 | 406.20 | 325.16 | 811.37 | 2 |
| HT44-45 | 490-509 | 2103.05 | 1052.03 | 701.69 | 526.52 | 421.42 | 701.66 | 3 |
| HT46 | 510-516 | 845.40 | 423.21 | 282.47 | 212.11 | 169.89 | 423.19 | 2 |
| HT47 | 517-518 | 232.14 | 116.57 | 78.05 | 58.79 | 47.23 | — | |
| HT48 | 519-523 | 623.35 | 312.18 | 208.46 | 156.59 | 125.48 | N.D | |
| HT49 | 524-527 | 463.22 | 232.11 | 155.08 | 116.56 | 93.45 | N.D | |
| HT50 | 528-538 | 1339.70 | 670.36 | 447.24 | 335.68 | 268.75 | 670.33 | 2 |
| HT51 | 539-549 | 1277.55 | 639.28 | 426.52 | 320.14 | 256.32 | 639.26 | 2 |
| HT52 | 550-564 | 1879.83 | 940.42 | 627.28 | 470.71 | 376.77 | 940.39 | 2 |
| HT52(m) | 550-564 | 1919.80 | 960.40 | 640.60 | 480.70 | 384.76 | 960.40 | 2 |
| HT53 | 565-612 | 4129.06 | 2065.03 | 1377.02 | 1033.02 | 826.62 | 1032.99 | 4 |
| HT54 | 613-621 | 923.46 | 462.23 | 308.49 | 231.62 | 185.50 | 462.22 | 2 |
| HT55 | 622-642 | 2310.11 | 1155.56 | 770.71 | 578.28 | 462.83 | 770.68 | 3 |
| HT56 | 643-658 | 1784.94 | 892.97 | 595.65 | 446.99 | 357.79 | 595.63 | 3 |
| HT56(de) | 643-658 | 1785.94 | 893.47 | 595.98 | 447.24 | 357.99 | 595.96 | 3 |
| HT57 | 659-663 | 525.27 | 263.14 | 175.76 | 132.07 | 105.86 | 525.25 | 1 |
| HT58 | 664-691 | 3001.30 | 1501.15 | 1001.11 | 751.08 | 601.07 | 1001.08 | 3 |
| HT58(m) | 664-691 | 3041.20 | 1521.10 | 1014.40 | 761.05 | 609.04 | 1014.40 | 3 |
| HT59 | 692-701 | 934.54 | 467.77 | 312.18 | 234.39 | 187.71 | 467.76 | 2 |
| HT59(m) | 692-701 | 974.40 | 487.70 | 325.47 | 244.35 | 195.68 | 487.70 | 2 |
| HT60 | 702-705 | 445.30 | 223.16 | 149.11 | 112.08 | 89.87 | 445.29 | 1 |

HT: Heavy chain tryptic peptide
(de): Asn deamination
(m): modification (chemical attachment)
*De-glycosylated peptide
N.D: Not detected

TABLE 13

| Frag# | Res# | Theoretical mass(TPD) | | | | | Observed mass (LC-MS) | Charge |
|---|---|---|---|---|---|---|---|---|
| | | M + H | M + 2H | M + 3H | M + 4H | M + 5H | | |
| LT1 | 1-18 | 1878.89 | 939.95 | 626.97 | 470.48 | 376.58 | 939.92 | 2 |
| LT2 | 19-24 | 692.38 | 346.69 | 231.46 | 173.85 | 139.28 | 692.35 | 1 |
| LT3 | 25-30 | 631.35 | 316.18 | 211.12 | 158.59 | 127.08 | 631.39 | 1 |
| LT4 | 31-42 | 1495.77 | 748.39 | 499.26 | 374.70 | 299.96 | 499.25 | 3 |
| LT5 | 43-45 | 315.20 | 158.11 | 105.74 | 79.56 | 63.85 | 315.19 | 1 |
| LT6 | 46-61 | 1675.94 | 838.47 | 559.32 | 419.74 | 335.99 | 838.45 | 2 |
| LT6(m) | 46-61 | 1718.80 | 859.90 | 573.60 | 430.45 | 344.56 | 859.90 | 2 |
| LT7 | 62-90 | 3130.43 | 1565.72 | 1044.15 | 783.36 | 626.89 | 1044.12 | 3 |
| LT8 | 91-93 | 452.23 | 226.62 | 151.41 | 113.81 | 91.25 | 452.21 | 1 |
| LT9 | 94-103 | 1069.53 | 535.27 | 357.18 | 268.14 | 214.71 | 535.25 | 2 |
| LT10 | 104-107 | 488.31 | 244.66 | 163.44 | 122.83 | 98.47 | 486.29 | 1 |
| LT11 | 108-108 | 175.12 | 88.06 | 59.05 | 44.54 | 35.83 | — | |
| LT10-11 | 104-108 | 644.41 | 322.71 | 215.48 | 161.86 | 129.69 | 322.70 | 2 |
| LT12 | 109-126 | 1932.01 | 966.51 | 644.68 | 483.76 | 387.21 | 966.48 | 2 |
| LT13 | 127-142 | 1740.87 | 870.94 | 580.96 | 435.97 | 348.98 | 870.91 | 2 |
| LT13(m) | 127-142 | 1780.80 | 890.90 | 594.27 | 445.95 | 356.96 | 890.90 | 2 |
| LT13(m)(de) | 127-142 | 1781.80 | 891.40 | 594.60 | 446.20 | 357.16 | 891.40 | 2 |
| LT14 | 143-145 | 347.19 | 174.10 | 116.40 | 87.55 | 70.24 | 347.18 | 1 |
| LT15 | 146-149 | 560.32 | 280.66 | 187.45 | 140.84 | 112.87 | 560.30 | 1 |
| LT16 | 150-169 | 2135.97 | 1068.49 | 712.66 | 534.75 | 428.00 | 712.64 | 3 |
| LT17 | 170-183 | 1502.76 | 751.88 | 501.59 | 376.45 | 301.36 | 751.86 | 2 |
| LT16-17 | 150-183 | 3619.71 | 1810.36 | 1207.24 | 905.68 | 724.75 | 1207.21 | 3 |
| LT18 | 184-188 | 625.28 | 313.15 | 209.10 | 157.08 | 125.86 | 625.26 | 1 |
| LT19 | 189-190 | 284.17 | 142.59 | 95.40 | 71.80 | 57.64 | — | |
| LT20 | 191-207 | 1818.91 | 909.96 | 506.97 | 455.48 | 364.59 | 606.96 | 3 |
| LT19-20 | 189-207 | 2084.06 | 1042.53 | 695.36 | 521.77 | 417.62 | 521.75 | 4 |
| LT21 | 208-211 | 523.26 | 262.14 | 175.09 | 131.57 | 105.46 | 523.24 | 1 |
| LT22 | 212-214 | 308.09 | 154.55 | 103.37 | 77.78 | 62.42 | 308.08 | 1 |
| LT21-22 | 208-214 | 812.34 | 406.67 | 271.45 | 203.84 | 163.27 | 406.66 | 2 |

LT: Light chain tryptic peptide
(de): Asn deamination
(m): modification (chemical attachment)

In FIG. 20, according to the LC-MS/MS de-novo sequencing result, binding of a compound to the peptide was detected. In FIG. 20A, a compound of 43 Da bound to the N-terminus of HT24(m)(de) peptide represented by a sequence of VVSVLTVLHQDWLNGK (residues 306 to 321 of SEQ ID NO: 59), and asparagine amino acid 319 was modified by deamination. In FIG. 20B, an LT13(m) peptide was identified as a chemical-binding peptide having a molecular weight increased by 43 Da from the theoretical molecular weight. Other modified peptides shown in a peptide mapping table were finally identified by the LC-MS/MS peptide sequencing method as described above (FIG. 21).

Therefore, it was confirmed that 902 amino acids of the total 919 amino acids (in the heavy chain and the light chain) correspond to the amino acids of the heavy chain/light chain in the HuE10-101 protein. After completion of the analysis, total sequence coverage was detected at 98.1%.

From the above results, through the peptide mapping for HuE10-101, it was confirmed that the peptides had a 98.1% identical basic amino acid structure, and some had chemical-binding peptides and were weakly deaminated at an asparagine amino acid.

7-2-1. Analysis of Circular Dichroism (CD)

This experiment was carried out to estimate a secondary structure of a sample using circular dichroism (CD). Far-UV data obtained by the CD analysis was used to predict the secondary structure using JASCO secondary structure estimation software (FIG. 22).

Figure 22:
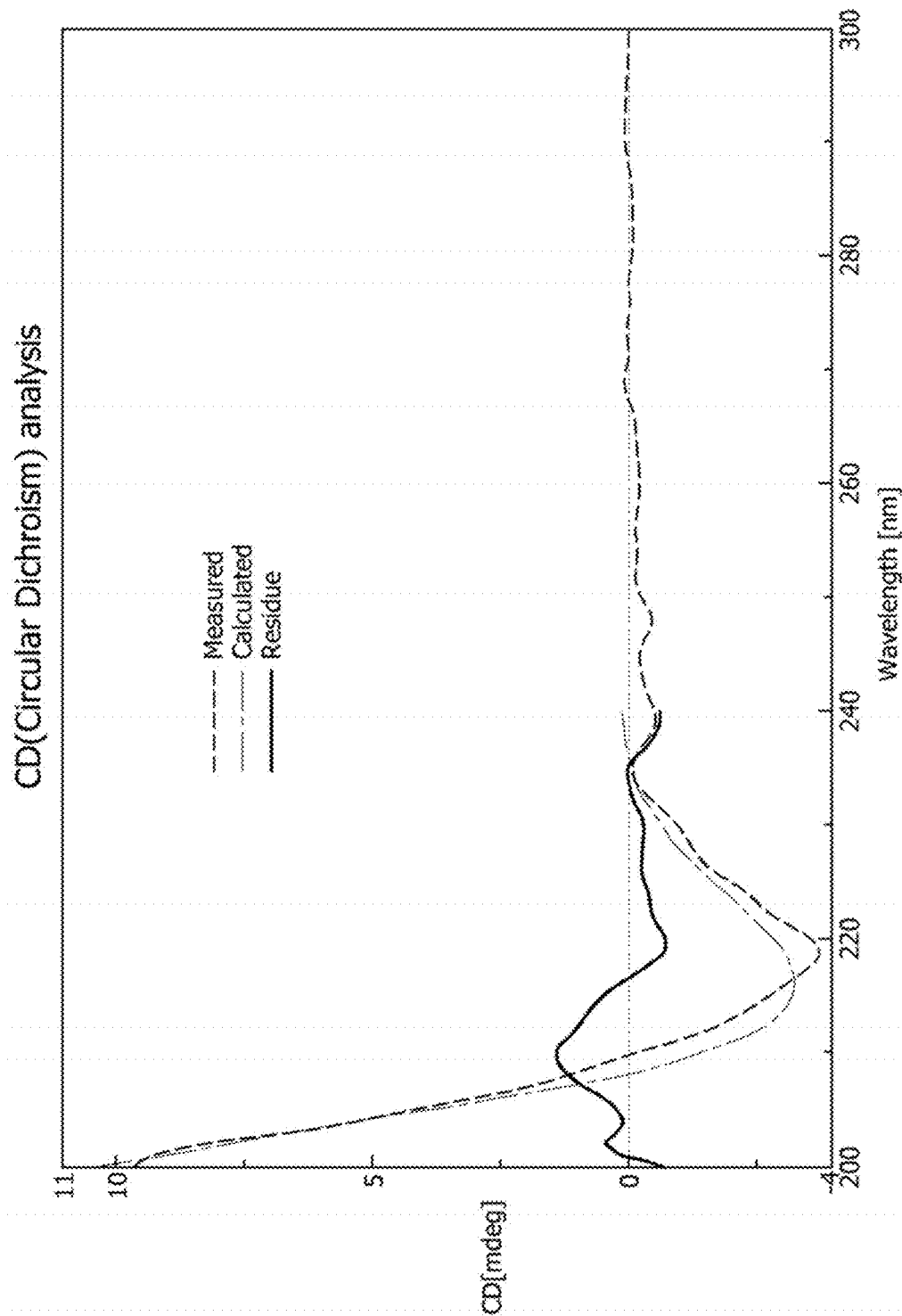
FIG. 22 shows a circular dichroism (CD) analysis result for predicting a secondary structure of the HuE10-101 protein.

As shown in FIG. 22, from the far-UV analysis result at 300-200 nm, it was confirmed that the HuE10-101 sample is present in a ratio of 77.9% beta and 22.1% turn.

7-2-2. Surface Plasmon Resonance (SPR) Analysis

For analysis of a binding strength of HuE10-101 to an antigen, one of the SPR tools, which is Bio-Rad ProteOn XPR36, was used. As a result of analyzing the binding strength of the antibody by individually coating an antigen such as TNF-α or CXCL10, the HuE10-101 had a binding strength of 0.195 nM with respect to TNF-α, and 3.54 nM with respect to CXCL10. The Humira used as a control group had a binding strength to TNF-α of 0.116 nM, but it did not bind to CXCL10 as expected.

Two channels of an XPR GLC chip were coated with 100 nM of TNF-α and CXCL10, respectively, and the antibody flowed over the channels, thereby evaluating the binding strength. For measurement, the GLC chip was initialized with 50% glycerol on ProteOn XPR 36, and stabilized with running buffer PBST (10 mM Na-phosphate, 150 mM NaCl, 0.005% Tween20, pH 7.4), which was flowed at 25° C. Five channels of the GLC chip were activated with 220 µl of a mixture of 0.04 M N-ethyl-N'-(3-dimethylaminopropyl) carbodiimide (EDC) and 0.001 M sulfo-N-hydroxysuccinimide (sulfo-NHS) at 1:1 ratio, which was flowed at a flow rate of 30 µl/min. Subsequently, 100 nM TNF-α or CXCL10 was coated using an acetate buffer (pH 5.5) at a rate of 30 µl/min. The chip activated with 1 M ethanol amine-HCl (pH 8.5) was inactivated. An immobilization level was detected at 800 RU (resonance units). PBS/T was used as a reference, the HuE10-101 or Humira antibody was diluted to reach a half of the original concentration, 5 nM, and thus the solutions were prepared in five serial concentrations and flowed over the coated antigens, and then a KD value was obtained.

Figure 23A:
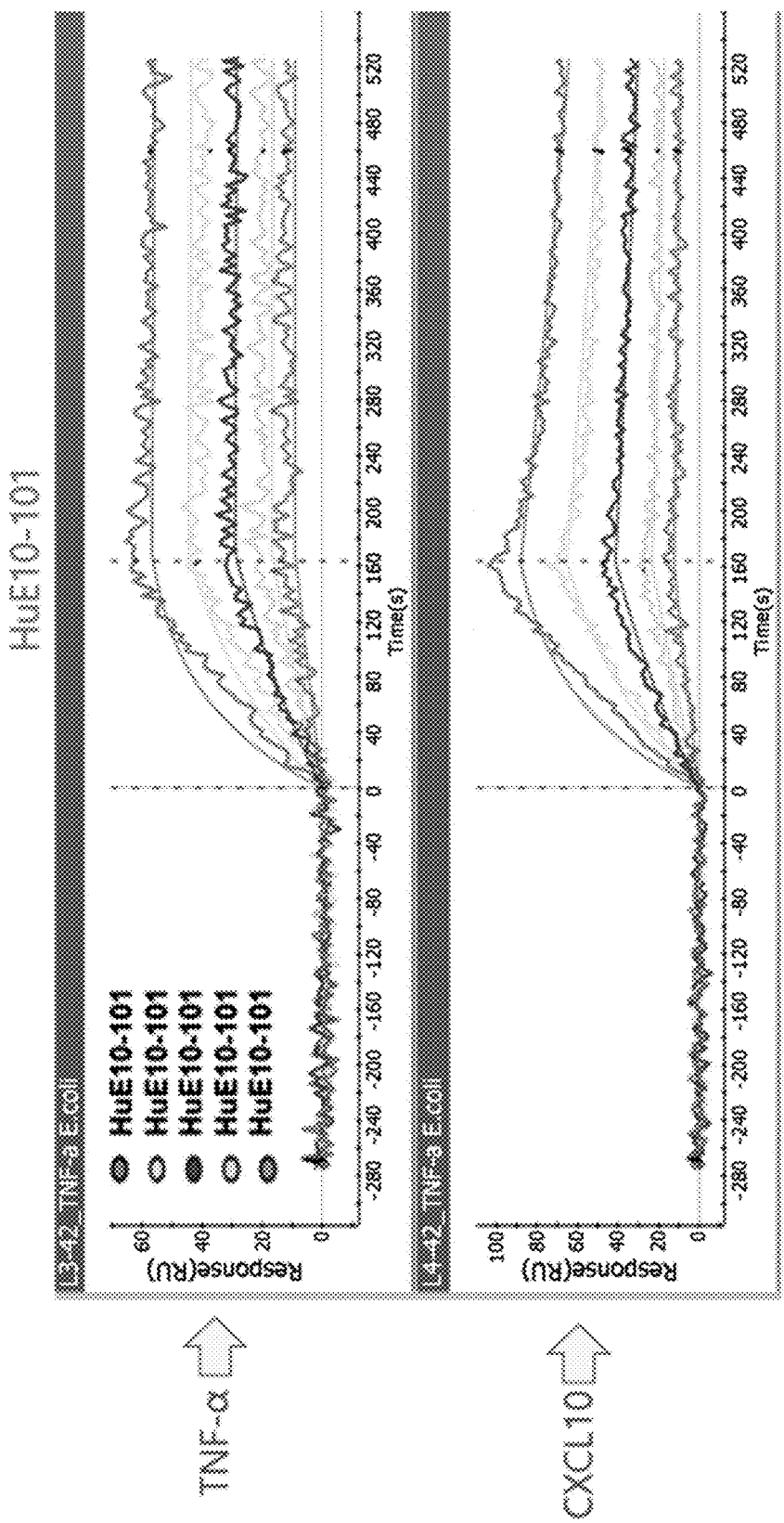
FIG. 23 shows the binding strength of Humira and HuE10-101 with respect to TNF-α and CXCL10, which is evaluated by ProteOn XPR36.
Figure 23B:
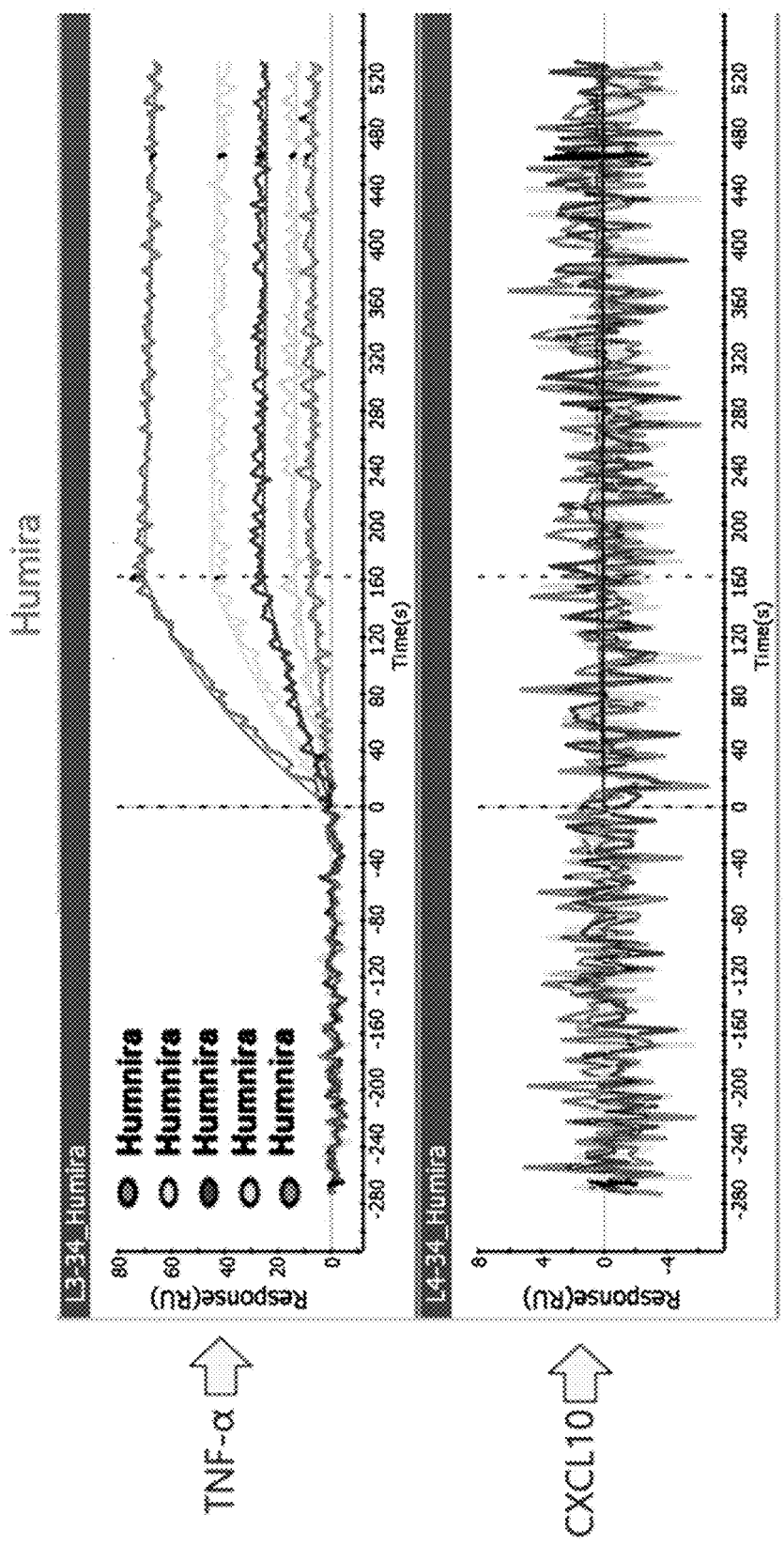

The XPR GLC chip was coated with 100 nM of TNF-α or CXCL10, and the Humira or HuE10-101 was diluted to reach a half of the original concentration, 5 nM, and the solutions prepared thereby were prepared in five concentrations and flowed over the antigens, and therefore, the sensogram shown in FIG. 23 was obtained.

FIG. 23 shows that the Humira easily bound to the antigen, TNF-α, but did not bind to CXCL10 at all. However, it was reconfirmed that HuE10-101 is a bispecific antibody that well binds to CXCL10 as well as TNF-α.

Table 14 shows KD values of antibodies against corresponding antigens obtained from the sensogram of FIG. 23. ka represents an association constant, kd represents a dissociation constant, and KD represents an equilibrium dissociation constant, which is a value obtained by dividing the kd value by the ka value. The binding strength of Humira only to the antigen, TNF-α, was detected, and the KD value of Humira was 0.116 nM. On the other hand, the bispecific antibody, HuE10-101 has the binding strength to TNF-α similar to that of Humira, and thus the KD value was 0.195 nM, but has a weaker binding strength to CXCL10, resulting in the KD value of 3.54 nM. The lower KD value of HuE10-101 to CXCL10 is because, when all of the results shown in FIG. 23 and Table 15 are combined, kd is a little lower than that to TNF-α.

TABLE 14

| Ligand | Coating | Ka $(M^{-1}S^{-1})$ | Kd $(S^{-1})$ | KD (M) | $R_{max}$ | Chi$^2$ |
|---|---|---|---|---|---|---|
| HuE10-101 | TNF-α | 3.60E+06 | 7.01E−04 | 1.95E−10 | 63.93 | 10.47 |
| | CXCL10 | 2.57E+06 | 9.11E−03 | 3.54E−9 | 116.13 | 10.66 |
| Humira | TNF-α | 1.43E+06 | 1.66E−04 | 1.16E−10 | 103.64 | 6.10 |
| | CXCL10 | N.D | N.D | N.D | — | — |

N.D: Not Detected
Ka: Association rate constant
kd: Dissociation rate constant
KD: Equilibrium dissociation constant 7-3. Immunochemical Assay 7-3-1. Enzyme-Linked Immunosorbent Assay (ELISA)

For an immunochemical assay for HuE10-101 against an antigen, ELISA was carried out. As a result of analyzing a binding strength of the antibody by individually coating of the antigen TNF-α or CXCL10, the binding strength of HuE10-101 against TNF-α was 0.495 nM, and the binding strength of HuE10-101 against CXCL10 was 1.9 nM. Humira used as a control group exhibited the binding strength to TNF-α of 0.5 nM, but did not bind to CXCL10 as expected.

The antigen TNF-α or CXCL10 was added to a 96-well immunoplate at a density of 100 ng/well to allow coating overnight at 4° C. 5% skim milk was added at 200 μl/well, and incubated at room temperature for 2 hours. Afterward, HuE10-101 and Humira were diluted to reach a half of the original concentration, 50 nM, and the resultant solution was added at 100 μl/well and incubated at room temperature for 2 hours. Two hours later, the plate was washed with 0.05% PBST 200 μl/well three times. In addition, anti-human FC-HRP (in goat) was mixed with 1% skim milk PBS at a 1:1000 ratio, thereby preparing a solution, and the resultant solution was added at 100 μl/well and incubated at room temperature for 1 hour. Subsequently, one hour later, the plate was washed with 0.05% PBST at 200 μl/well three times. An OPD solution was prepared and added at 100 μl/well to allow color development, and then the reaction was terminated with a stop buffer. Absorbance was analyzed at 492 nm.

Figure 24:
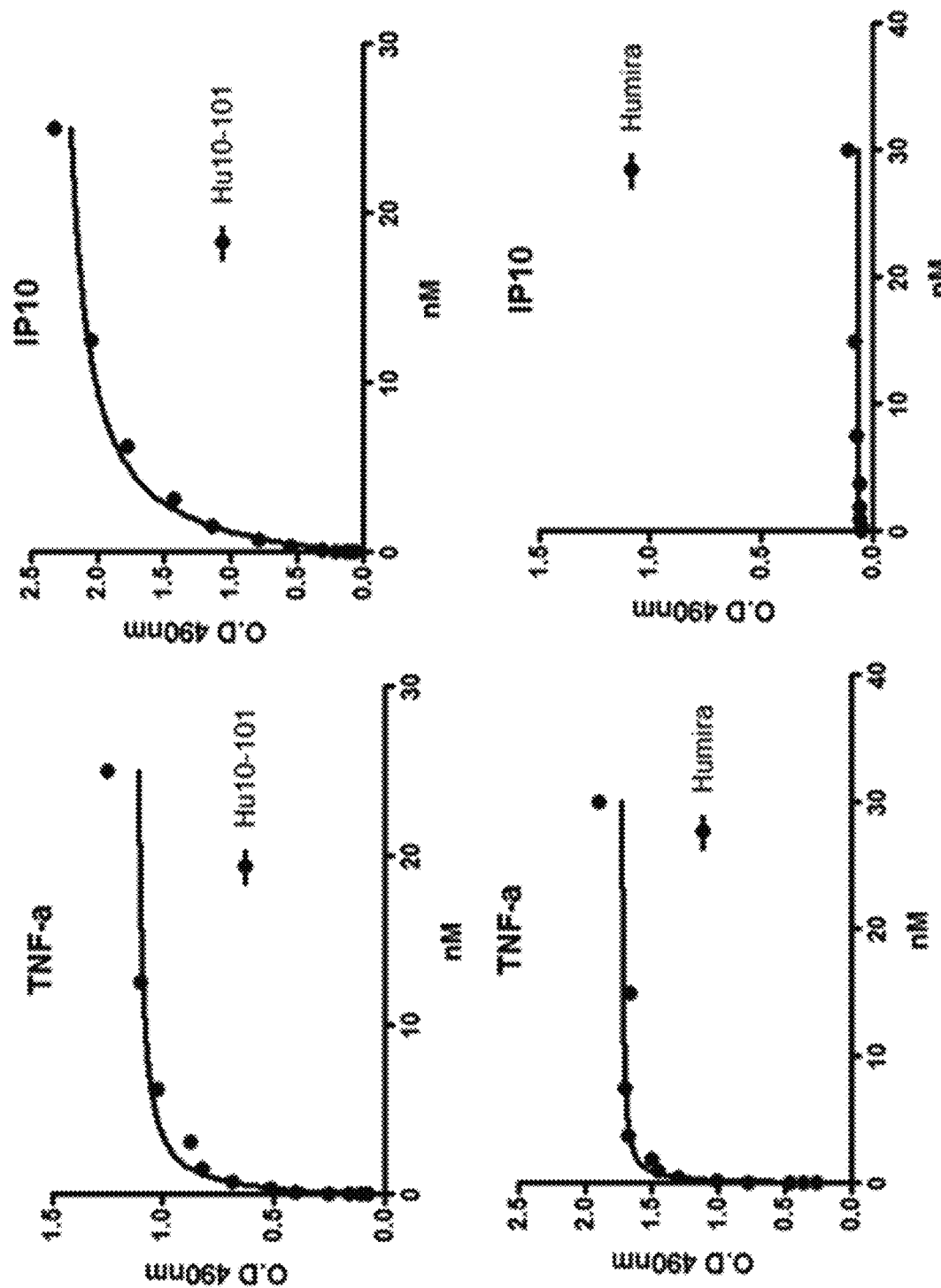
FIG. 24 shows the binding affinity confirmed by measuring a KD value based on ELISA.

A binding affinity as follows was determined by measuring a KD value through ELISA. An R2 value exhibiting reliability of the measurement value was 0.97 or more, which showed that reliabilities in all experiments were high. As a result, HuE10-101 was determined as a bispecific antibody easily binding to both of TNF-α and CXCL10 (FIG. 23). It was seen that the HuE10-measured antigen binding strengths were 4.5×10$^{-10}$ M (0.45 nM) and 1.9×10$^{-9}$ M (1.9 nM) to the respective antigens TNF-α and CXCL10. Meanwhile, it was determined that Humira used as a control group easily bound to TNF-α as expected, but did not bind to CXCL10 at all (FIG. 24). The binding affinity was 1.5×10$^{-10}$ M (0.15 nM), which was similar to that of HuE10-101, within an error range (Table 15).

TABLE 15

| ligand | TNF-a | | CXCL10 | |
|---|---|---|---|---|
| Ab | Hu10-101 | Humira | Hu10-101 | Humira |
| Kd value | 4.5 × 10$^{−10}$ | 1.5 × 10$^{−10}$ | 1.9 × 10$^{−9}$ | — |
| R2 | 0.97 | 0.98 | 0.99 | — |

Example 8: Evaluation of In Vitro Efficacy of Candidate Antibody 8-1. Evaluation of TNF-α Inhibitory Activity To evaluate TNF-α inhibitory activity of a candidate antibody, a technique for evaluating anti-TNF-α inhibitory activity was established using WEHI164 cells having a TNF-α receptor was established.

Figure 25:
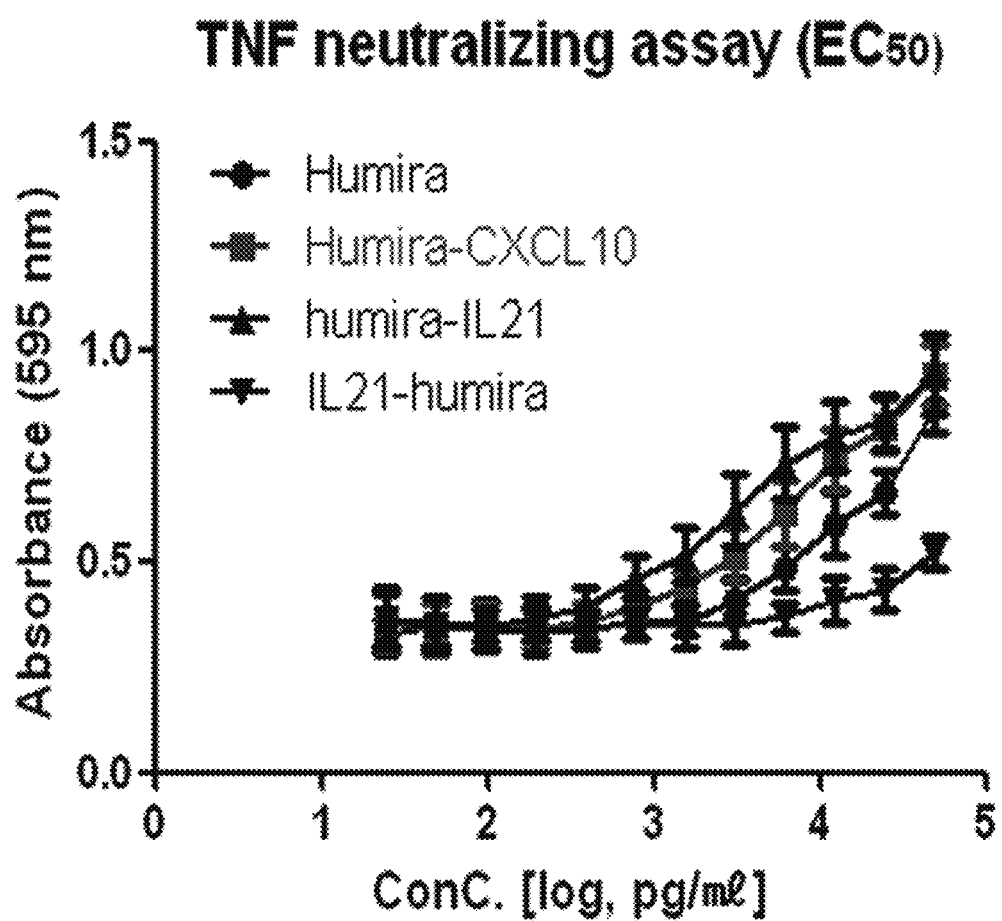
FIG. 25 shows evaluation results on the anti-TNF-α inhibitory activity of Humira, a Humira-generic antibody, HuE10-101, HuIL21R-101 and HuIL21R-100.

As a control group antibody, Humira (Abbott Laboratories) was used, and as a candidate antibody, a Humira-generic antibody (developed in the project), HuE10-101, was used. A concentration of each antibody was diluted to a half of the original concentration, and hTNF-α was added to the dilution to allow cell culturing, and then cells were cultured in a 5% CO$_2$, 37° C. incubator with addition of thiazolyl blue tetrazolium (MTT). After lysis of the cells, absorbance was measured at 595 nm (FIG. 25).

According to the analysis, the TNF-α inhibitory activity was observed at lower concentrations of the Humira-generic antibody, HuE10-101, HuIL21R-101, and HuIL21R-100 (developed in the project) than a positive control, Humira. As a result, the inhibitory activity of the candidate antibody against TNF-α was improved compared to Humira (FIG. 25).

8-2. Evaluation of CXCL10 Inhibitory Activity

Figure 26:
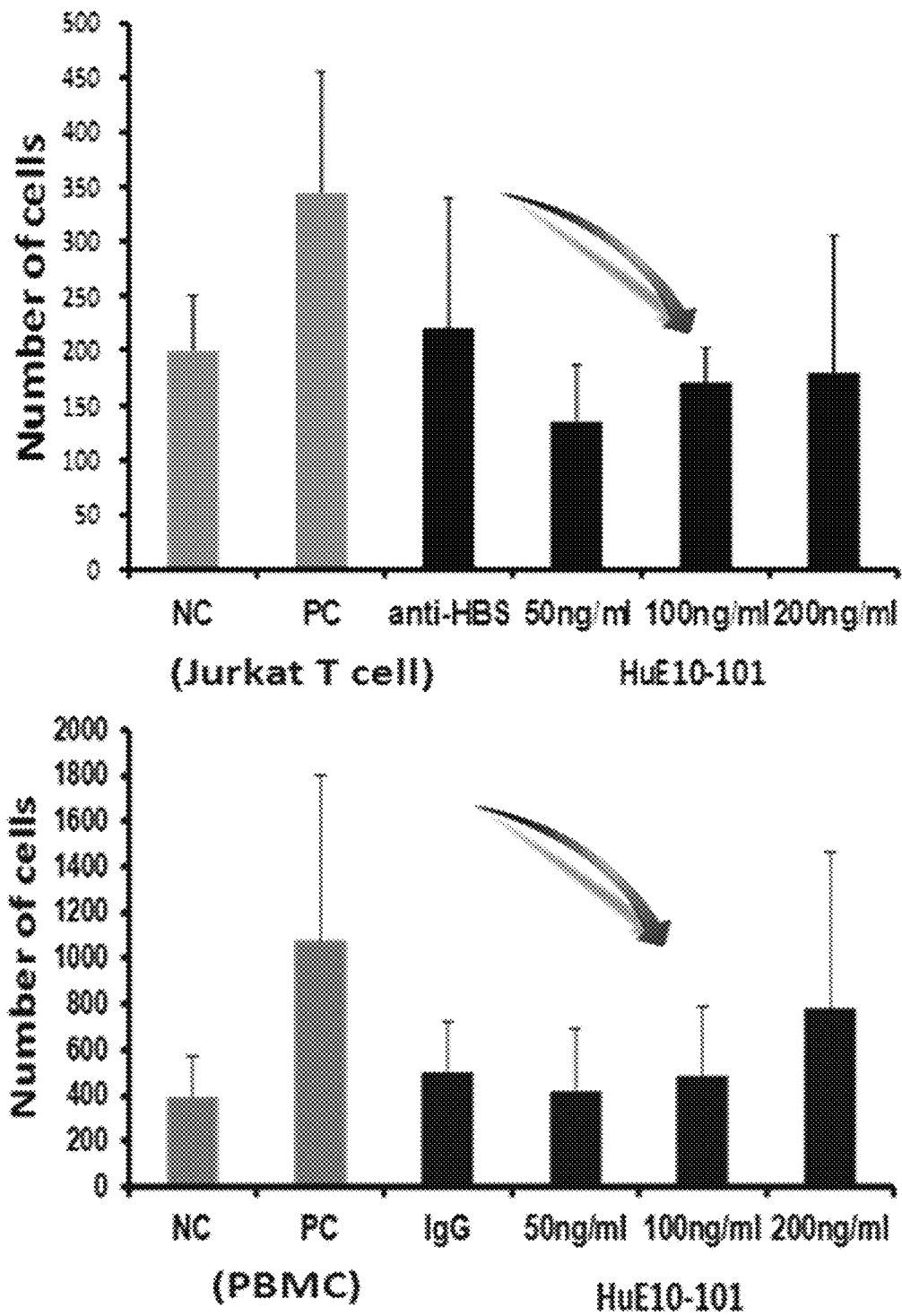
FIG. 26 shows graphs of evaluation results of chemotactic responsiveness of HuE10-101 with respect to CXCL10, where NC: negative control, PC: positive control (left: Jurkat T cell, right: PBMC) NC: negative control, PC: positive control (left: Jurkat T cell, right: PBMC).

To evaluate the efficacy of the candidate antibody, an experimental method for cell chemotaxis using a transwell system was established. Through the previous study showing that chemotaxis of T cells is increased by CXCL10, the inventors observed a change in the cell chemotaxis increased by CXCL10 when the anti-CXCL10 antibody, HuE10-101, was used as a treatment. Jurkat T cells were cultured in a cell culture transwell having a pore size of 5.0 μm for 4 hours, and mobilization of the Jurkat T cells was evaluated. For an experimental group, upper and lower chambers were treated with HuE10-101 at concentrations of 50 ng/ml, 100 ng/ml and 200 ng/ml, and to prepare the chemotaxis condition increased by CXCL10, the lower chamber was additionally treated with hCXCL10. For a positive control, only the lower chamber was treated with hCXCL10, and the increase in chemotaxis by CXCL10 was observed. As a result, it was shown that cell mobilization was effectively decreased in the experimental group, compared to the positive control (PC) (FIG. 26).

Figure 27:
FIG. 27 is a schematic diagram showing experimental conditions for osteoclast differentiation when a coculture system is introduced.

In a conventional osteoclast differentiation experiment, a macrophage differentiated into an osteoclast by directly adding M-CSF and RANKL. However, to analyze a degree of osteoclast differentiation depending on an amount of RANKL emitted from CD4+ cells due to CXCL10 stimulation, the inventors introduced a CD4+/CD14+ coculture system to induce osteoclast differentiation, and thus established experimental conditions (FIG. 27).

Figure 28:
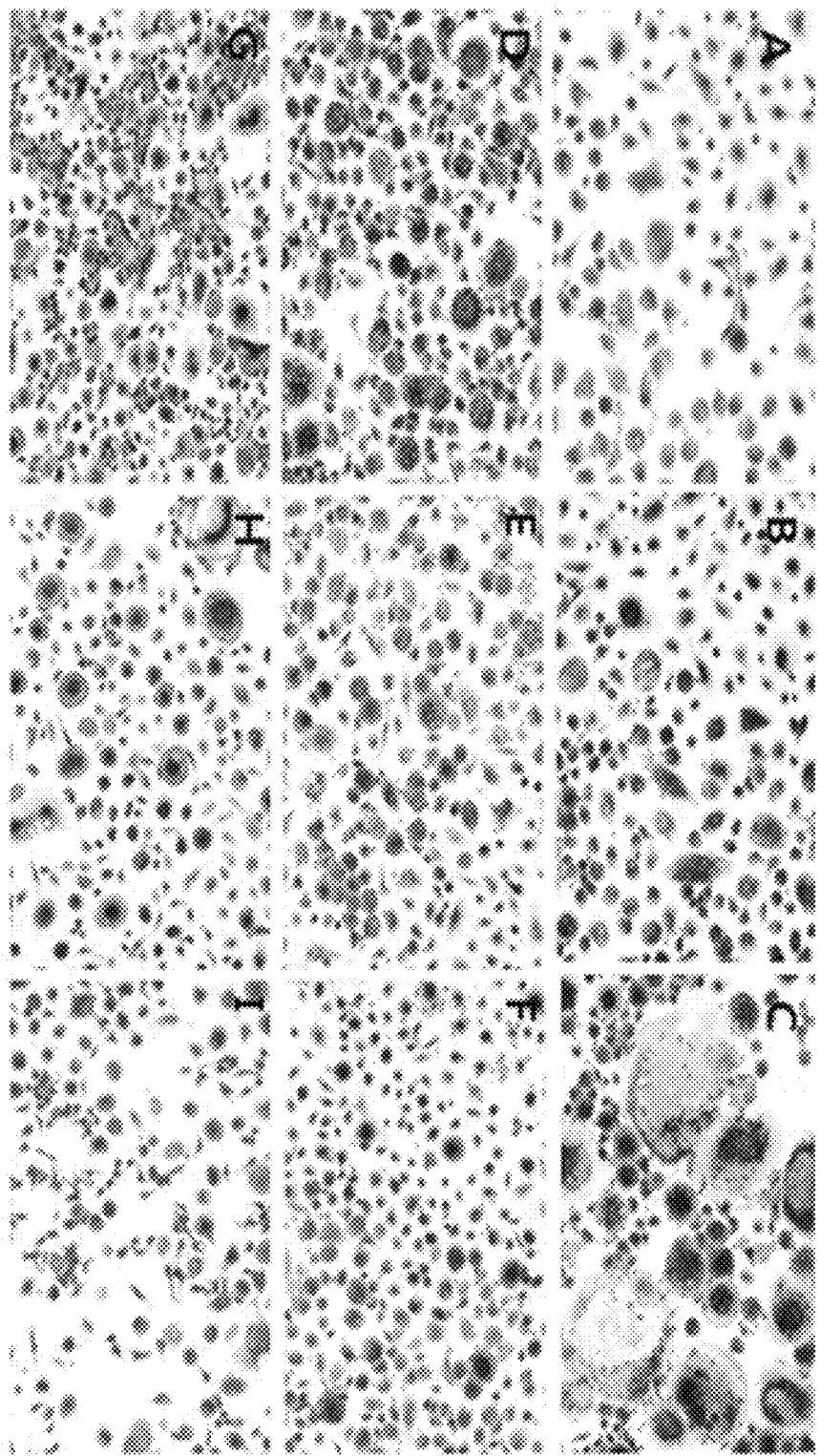
FIG. 28 shows osteoclast differentiation results obtained by TRAP staining.

To observe the osteoclast differentiation inhibitory activity, osteoclast precursor cells (CD14+) and CD4+ cells were separated from the blood, and osteoclast differentiation from two cells was induced using a coculture system, tartrate resistant acid phosphatase (TRAP) staining was carried out and observed with a microscope (FIG. 28).

Figure 29:
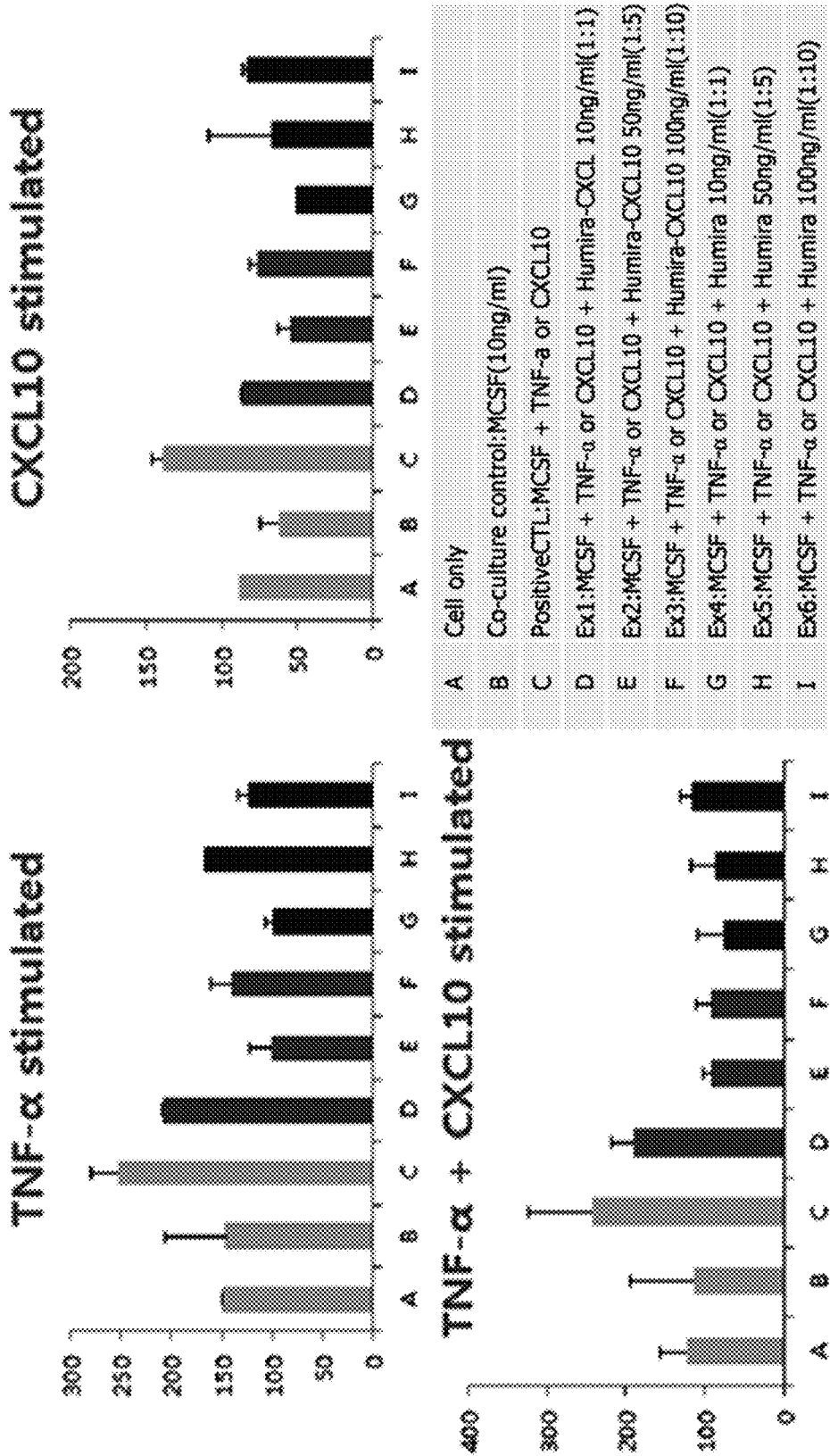
FIG. 29 shows an inhibitory effect of the osteoclast differentiation by anti-TNF-α and anti-CXCL10 (as the result of TRAP positive polynucleated cell counting), where RANKL induction conditions for CD4+ cells: stimulation of TNF-α, CXCL10, and TNF-α+CXCL10.

As a result of evaluating the osteoclast differentiation inhibitory activity by HuE10-101, it was shown that, compared to Humira used as a control group (G-I), in a group independently stimulated by TNF-α or CXCL10 and the coculture system which were stimulated by both of TNF-α and CXCL10, the osteoclast differentiation was decreased, independent of concentration (FIG. 29).

8-4. Evaluation of TNF-α Neutralizing Capacity of Antibody

To evaluate the efficacy of an antibody produced in a production cell line, TNF-α neutralizing capacity established in the second year was evaluated. In the experiment, WEHI164 cells having a TNF-α receptor were used. As a control group antibody, Humira (Abbott Laboratories) was used, and as an experimental group, HuE10-101 was used. The concentration of each antibody was subjected to 2-fold serial dilution, and the diluted cells were cultured by addition of recombinant human TNF-α, and cultured in a 5% $CO_2$, 37° C. incubator by addition of thiazolyl blue tetrazolium (MTT). After lysis of the cells, absorbance was measured at 595 nm to analyze an EC50 value.

Figure 30:
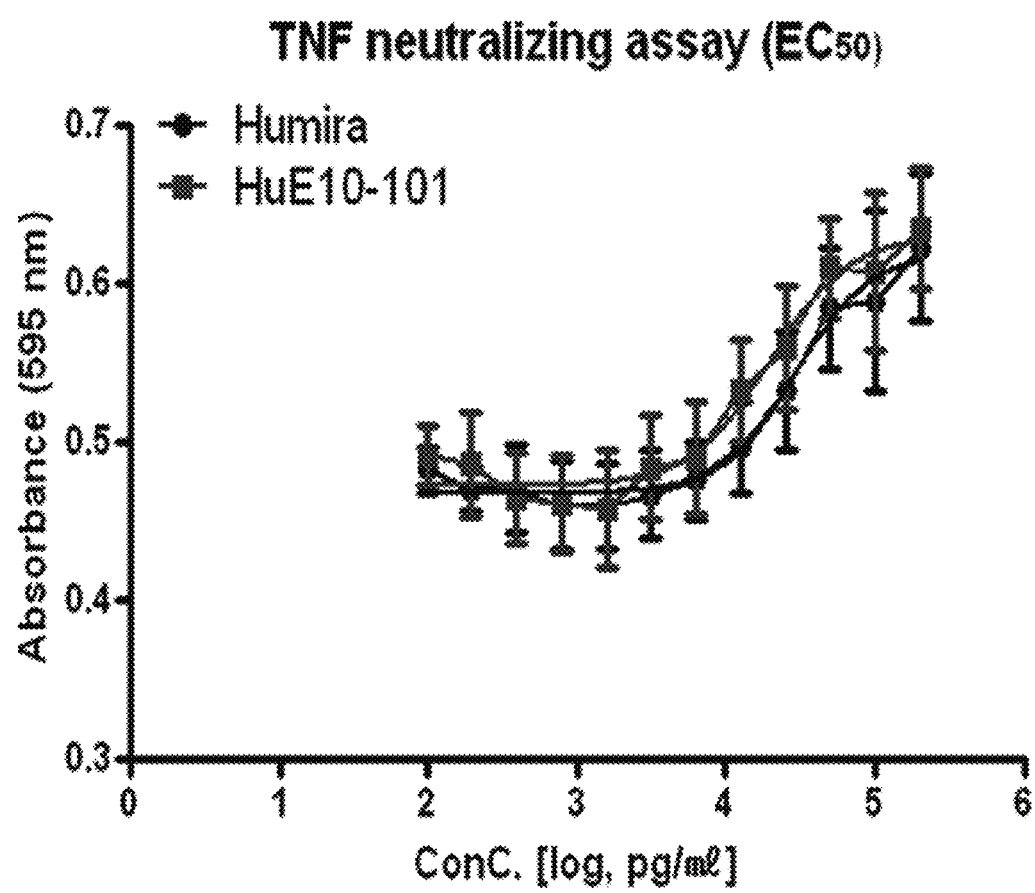
FIG. 30 shows TNF-α neutralizing capacity measured to evaluate the efficacy of an antibody produced in a production cell line.

According to the analysis, it was shown that, in the HuE10-101 treated group, compared to the Humira® treated group used as a control group, TNF-α neutralizing capacity was finally observed at a lower concentration. Also, compared with the antibody used in the second year, it was shown that the TNF-α neutralizing capacity was improved in the antibody produced in the newly-developed production cell line (FIG. 30).

Example 9: Evaluation of In Vivo Efficacy of Antibody 9-1. Evaluation of Efficacy of Bispecific Antibody in Humanized TNF Mouse 9-1-1. Humanized TNF Transgenic Mouse A TNF transgenic mouse model established by Keffer in 1991 was manipulated to remove TNF 3'UTR (untranslated region) serving to inhibit TNF, and a TNF transgenic gene was introduced to the mouse. Therefore, expression of TNF was increased to allow spontaneous induction of arthritis. The arthritis induced by the method described above, similar to rheumatoid arthritis, pathologically showed synovial thickening, infiltration of inflammatory cells into an articular cavity, pannus formation, and cartilage and bone damage.

The TNF transgenic mouse model paved the way to prove that TNF plays an important role in the occurrence of arthritis through confirmation of pathogenesis of arthritis induced by TNF. Today, the TNF transgenic mouse model is useful to evaluate the efficacy of a TNF-related therapeutic agent.

Accordingly, the inventors used the TNF transgenic mouse model to evaluate the efficacy of a bispecific antibody against TNF. A request to evaluate the efficacy of the bispecific antibody using the TNF transgenic mouse model was made to the Contract Research Organization (CRO) in Greece. The strain used in efficacy evaluation was Tg197, which is one of the human antibody evaluation models for rheumatoid arthritis suggested by the Food & Drug Administration (FDA). To develop a currently available TNF-α antagonist, Infliximab (Remicade), the Tg197 strain was used.

The progression of arthritis in the Tg197 TNF transgenic mouse model, which is the strain, has no critical difference between the sexes, and as the disease progresses, compared to a general mouse, the TNF transgenic mouse model was decreased in body weight. When tissues of the Tg197 strain were pathologically analyzed, very similar to rheumatoid arthritis, inflammatory infiltration, synovial thickening, cartilage damage, and bone erosion may be observed.

In the Tg197 TNF transgenic mouse model, a lesion was observed from three weeks after the experiment had started. Models having the third- to sixth-week lesions, which is an early stage of the lesion, were used to check a preventing effect, and models having the sixth-to ninth-week lesions were generally used to check a therapeutic effect. Therefore, to evaluate the efficacy of the bispecific antibody, an experiment was carried out from the third to ninth weeks. Clinical evaluation was carried out with arthritis scores during the evaluation period and the change in body weight.

TABLE 16

| Arthritis scores | |
|---|---|
| Arthritis score | Characteristic |
| 0/not diseased | Not arthritic (normal appearance, the mouse was suspended and able to bear its own body weight) |
| 0.5/mildly diseased | Arthritis occurred (lightly swollen joint) |
| 1.0/mildly-moderately diseased | Light symptoms (distortion of joint due to swelling, inflammatory foot) |
| 1.5/moderately diseased | Moderate arthritis (joint-foot swellings, reduction of entire body flexibility, reduction in grip strength) |
| 2.0/moderately-seriously diseased | moderate arthritis (serious joint, foot and finger swelling, joint-deformation of a leg, not suspended, no body flexibility, no grip strength, the body trembled when moved, but able to move forward) |
| 2.5/seriously diseased | serious arthritis (the symptoms at 2.0 become serious, difficulty in moving) |
| 3.0/very seriously diseased | Very serious arthritis (ankylosis occurred, difficulty in moving) |

Also, after the end of the experiment, through histopathological evaluation, the severity of arthritis lesions was evaluated. Among the histopathological characteristics of rheumatoid arthritis, over-proliferation of joint synoviocytes and destruction of cartilage tissues caused thereby were representative. A mouse knee tissue was isolated and immobilized with formalin, a calcium compound was removed, a block was manufactured with paraffin, and a 4-μm tissue slice was manufactured using a microtome. Synovial inflammation, bone erosion, cartilage damage and leukocyte infiltration were investigated by hematoxylin and eosin (H&E) staining Here, the evaluation was carried out by a blind test in which a sample was unknown. Histopathological evaluation was carried out with reference to the table below.

TABLE 17

Histopathology scoring system
HISTOPATHOLOGICAL CRITERIA FOR
SCORING ARTHRITIC PHENOTYPE

| SCORE[1] | CRITERIA |
|---|---|
| 0 | No detectable pathology |
| 1 | Hyperplasia of the synovial membrane and presence of polymorphonuclear infiltrates. Mild tendonitis may be present. |
| 2 | Pannus and fibrous tissue formation and focal subchondral bone erosion |
| 3 | Cartilage destruction and bone erosion |
| 4 | Extensive cartilage destruction and bone erosion. Bone outline structure is lost |

Figure 31:
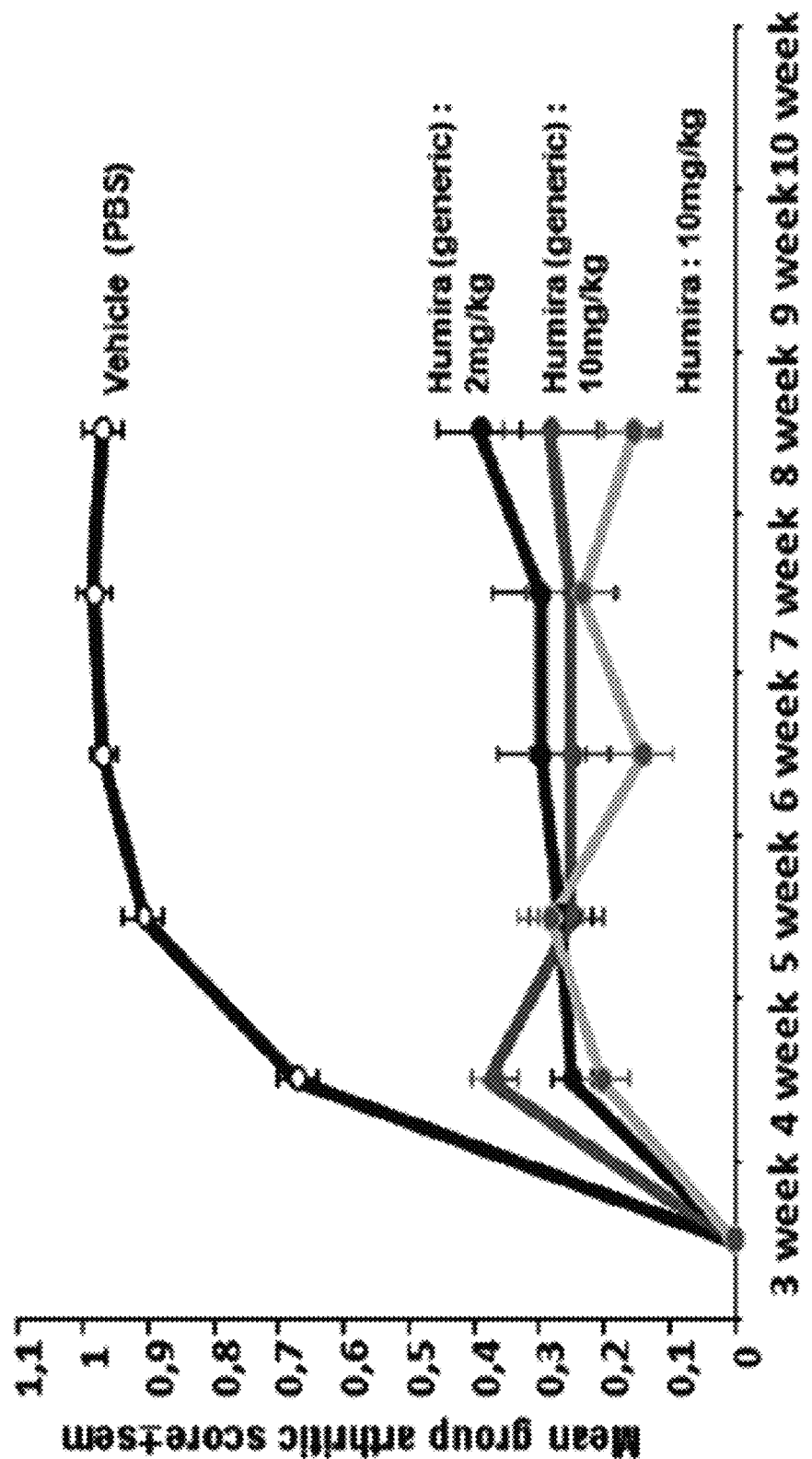
FIG. 31 shows arthritis scores determined after the Humira and Humira-generic antibodies are administered at different concentrations.
Figure 32:
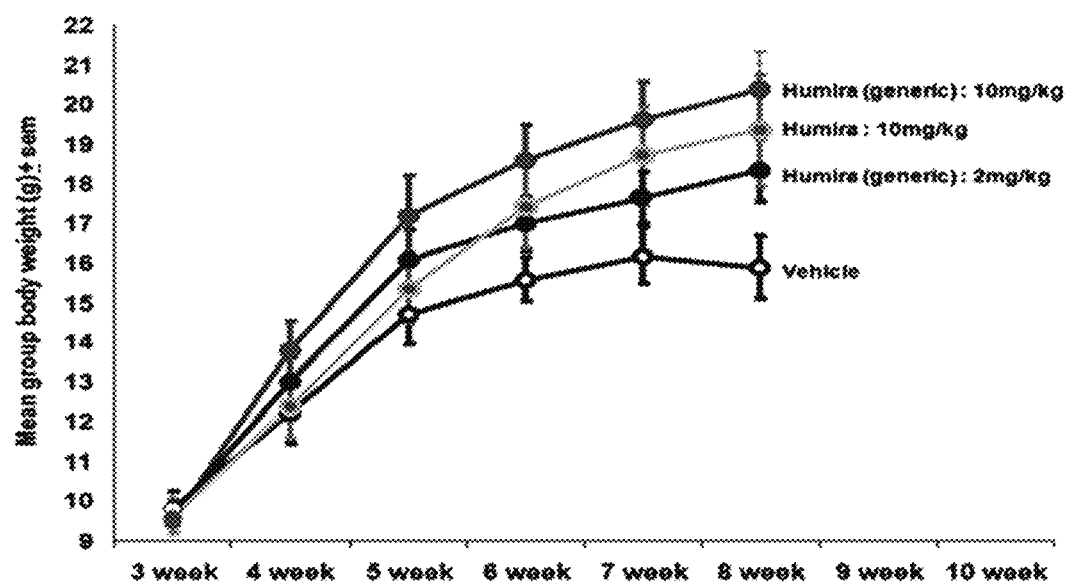
FIG. 32 shows body weight changes determined after the Humira and Humira-generic antibodies are administered at different concentrations.

9-1-2. Evaluation Result for Efficacy of Candidate Antibody Using Humanized TNF Transgenic Mouse Humira, which was conventionally commercialized and widely used, was administered into mice at 10 mg/kg, and Humira-generic antibodies developed by the inventors were administered into mice at 2 and 10 mg/kg, and clinical changes were observed and evaluated. As the result of measuring arthritis scores of Humira and the Humira-generic antibodies, in a vehicle group, the arthritis score was 1.48, and when the concentration of Humira used as a control group was 10 mg/kg, the arthritis score was 0.22. When the concentrations of the Humira-generic antibodies were 2 and 10 mg/kg, the arthritis scores were 0.66 and 0.52, respectively (FIG. 31). As a disease progresses, the TNF transgenic mouse model shows clinically considerable reduction in body weight. Measurement of the change in body weight was performed in the same manner as used in measurement of arthritis scores. In the vehicle group, the body weight was 15.26 g, and when the concentration of Humira used as a control group was 10 mg/kg, the body weight was 20.23 g. When the concentrations of the Humira-generic antibodies were 2 and 10 mg/kg, respectively, the body weights were 18.3 g and 20.58 g, respectively (FIG. 32). As a result of clinical evaluation of the Humira-generic antibody, similar to Humira used as a control group, as the concentration of the Humira-generic antibody was increased, the arthritis score was reduced, and a distinctive increase in body weight was shown.

Figure 33:
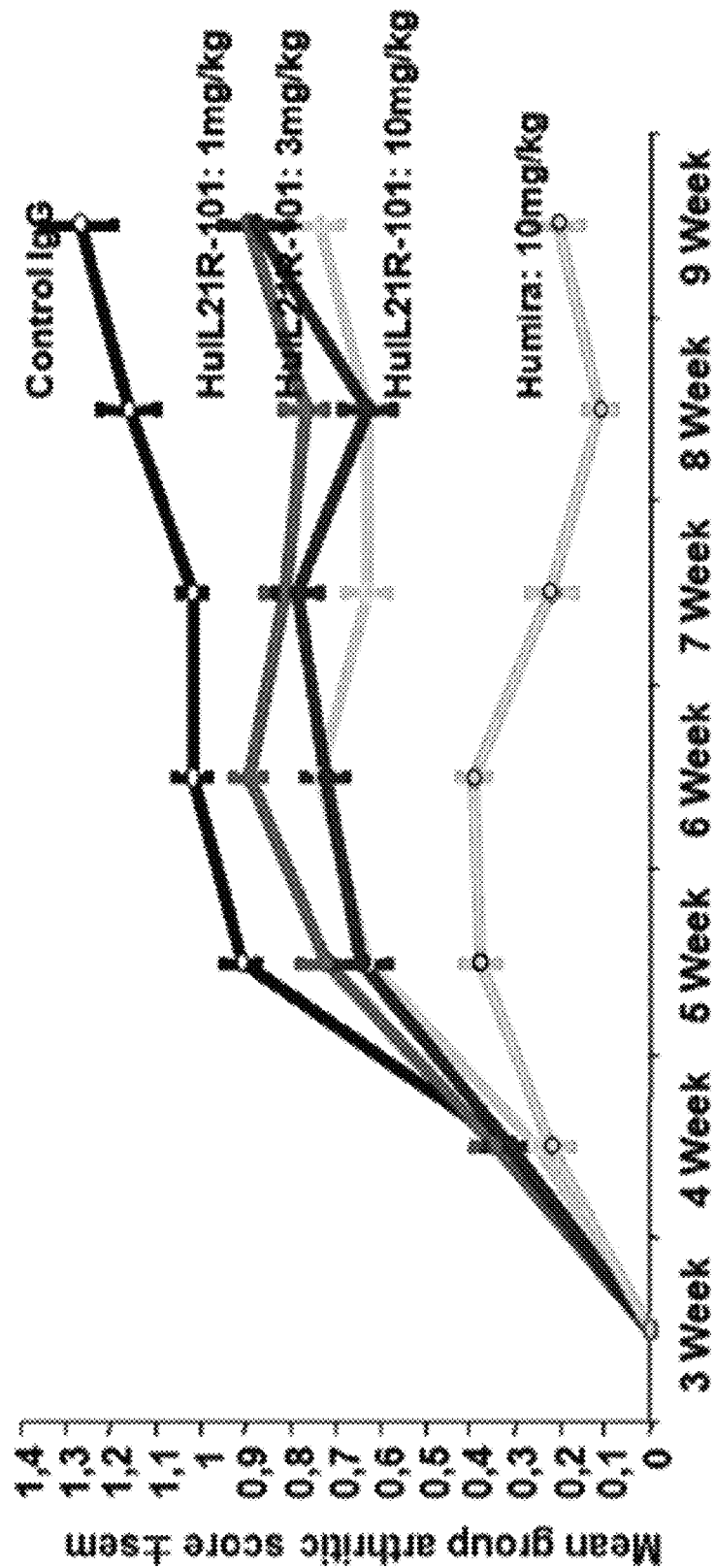
FIG. 33 shows arthritis scores determined after HuIL21-101 is administered at different concentrations.
Figure 34:
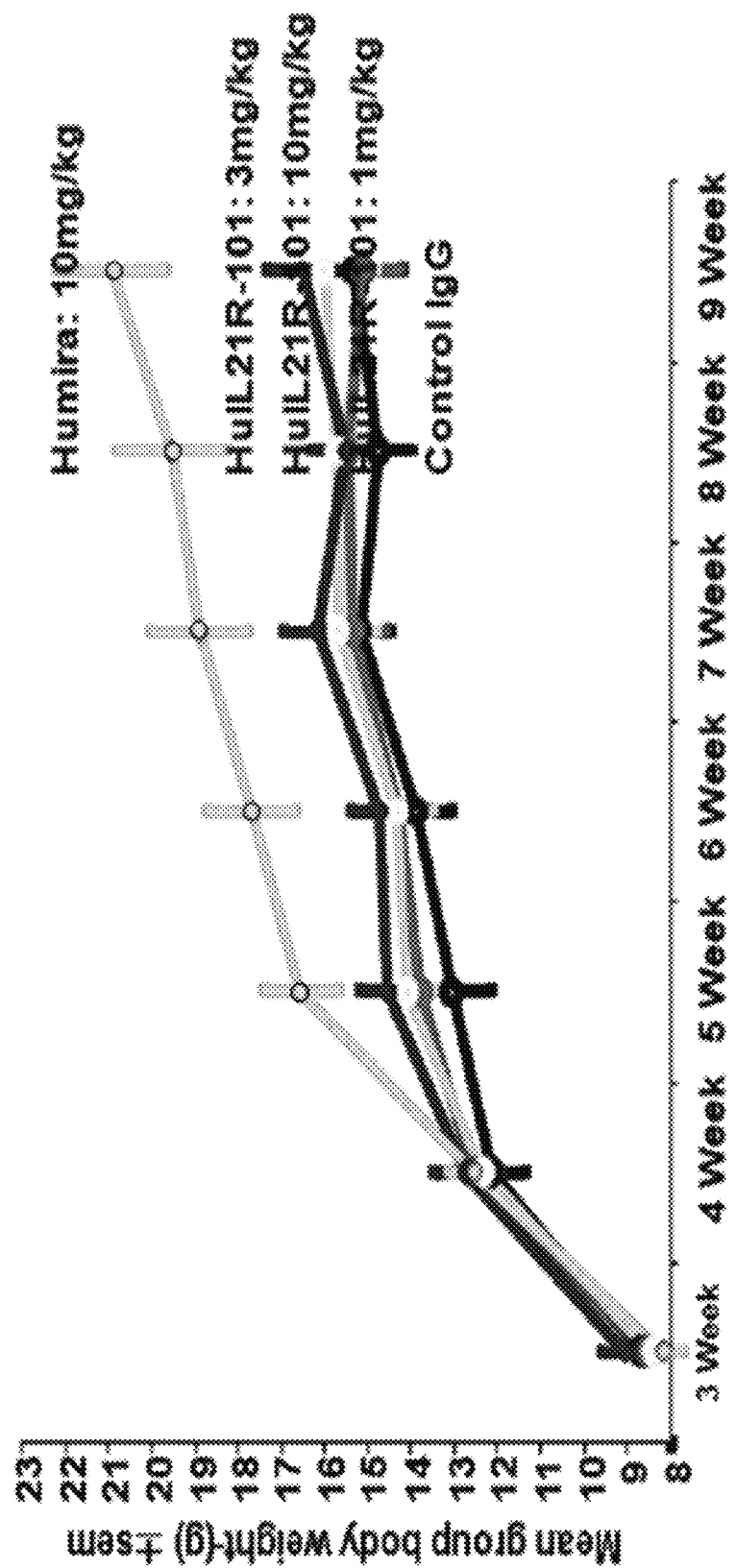
FIG. 34 shows body weight changes determined after HuIL21-101 is administered at different concentrations.

To evaluate the efficacy of HuIL21R-101, as a control group, Humira was used, as an experimental group, HuIL21R-101 was administered into mice at various concentrations of 1, 3 and 10 mg/kg, and clinical changes were observed and evaluated. As a result of measuring arthritis scores of HuIL21R-101, a vehicle group, human control IgG, had an arthritis score of 1.27, and when the concentration of a control, Humira was 10 mg/kg, the arthritis score of Humira was 0.20. When the concentration of the experimental group, HuIL21R-101, was 1, 3, or 10 mg/kg, respectively, the arthritis score was 0.89, 0.73 or 0.88 (FIG. 33). As a result of measuring the change in body weight, in the vehicle group, the body weight was 15.4 g, and when the concentration of the control, Humira was 10 mg/kg, the body weight was 20.9 g. When the concentration of the experimental group, HuIL21R-101, was 1, 3 or 10 mg/kg, respectively, the body weight was 15.1, 16.0 or 16.5 g (FIG. 34).

According to the clinical evaluation of HuIL21R-101, compared to the control, Humira, the arthritis score of HuIL21R-101 was not significantly reduced, and a distinctive increase in body weight was not shown. Based on the previous result for HuIL21R-101 and the efficacy evaluation result using the TNF transgenic mouse model, HuIL21R-101 was excluded in the final candidate antibody group.

Figure 35:
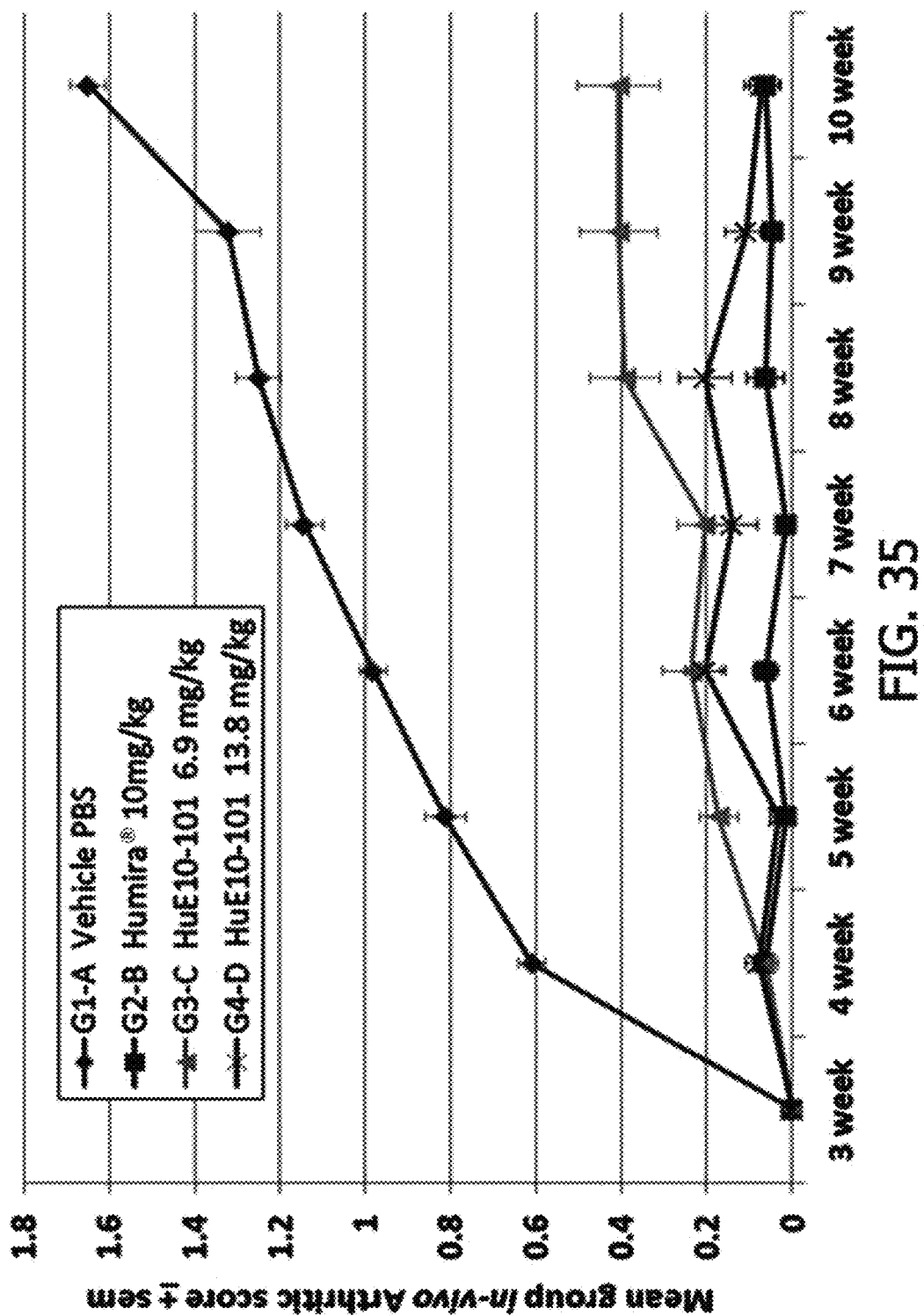
FIG. 35 shows arthritis scores determined after HuE10-101 is administered at different concentrations.

9-1-3. Evaluation Result for Efficacy of Bispecific Antibody Using Humanized TNF Transgenic Mouse As a control group, Humira® was used, and as experimental groups, HuE10-101 was administered into mice at concentrations of 6.9 and 13.8 mg/kg, which are equivalent amounts relative to the mass of the control, in order to observe and evaluate clinical changes. The arthritis score of HuE10-101 was 1.65 in a vehicle group, Human Control IgG, and the arthritis score was 0.06 in the control group in which the concentration of Humira® was 10 mg/kg. In the experimental groups in which the concentrations of HuE10-101 were 6.9 and 13.8 mg/kg, the arthritis scores were 0.41 and 0.07, respectively (FIG. 35).

Figure 36:
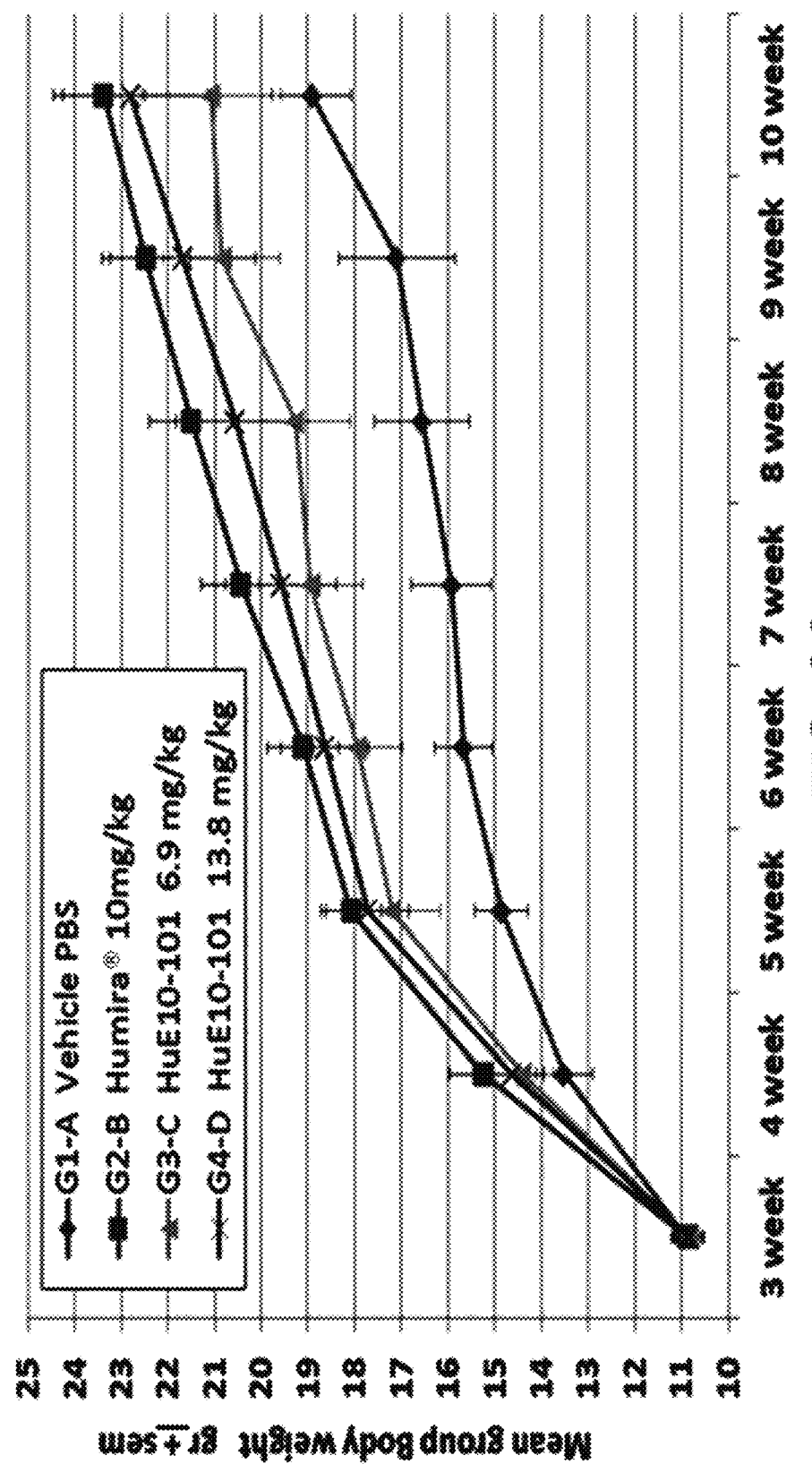
FIG. 36 shows body weight changes determined after HuE10-101 is administered at different concentrations.

The TNF transgenic mouse model shows a clinically considerable decrease in body weight as the disease is progressing. Measurement of the change in body weight was carried out at the same stage as the arthritis score measurement. As a result, a body weight was 18.92 g in the vehicle group, and 23.38 g in the control group in which the concentration of Humira® was 10 mg/kg. In the experimental groups, when the concentrations of HuE10-101 were 6.9 and 13.8 mg/kg, the body weights were 21.08 g and 22.80 g, respectively (FIG. 36).

According to the clinical evaluation for HuE10-101, the arthritis score was decreased, similar to that in the control group, the Humira-generic antibody, and it can be seen that as the concentration of HuE10-101 was increased, the arthritis score was decreased. Also, according to the measurement of the change in body weight, it was shown that the body weight reduced as a lesion is developing increases as the concentration of the administered HuE10-101 increases, similar to that in the Humira-generic antibody group.

Figure 37:
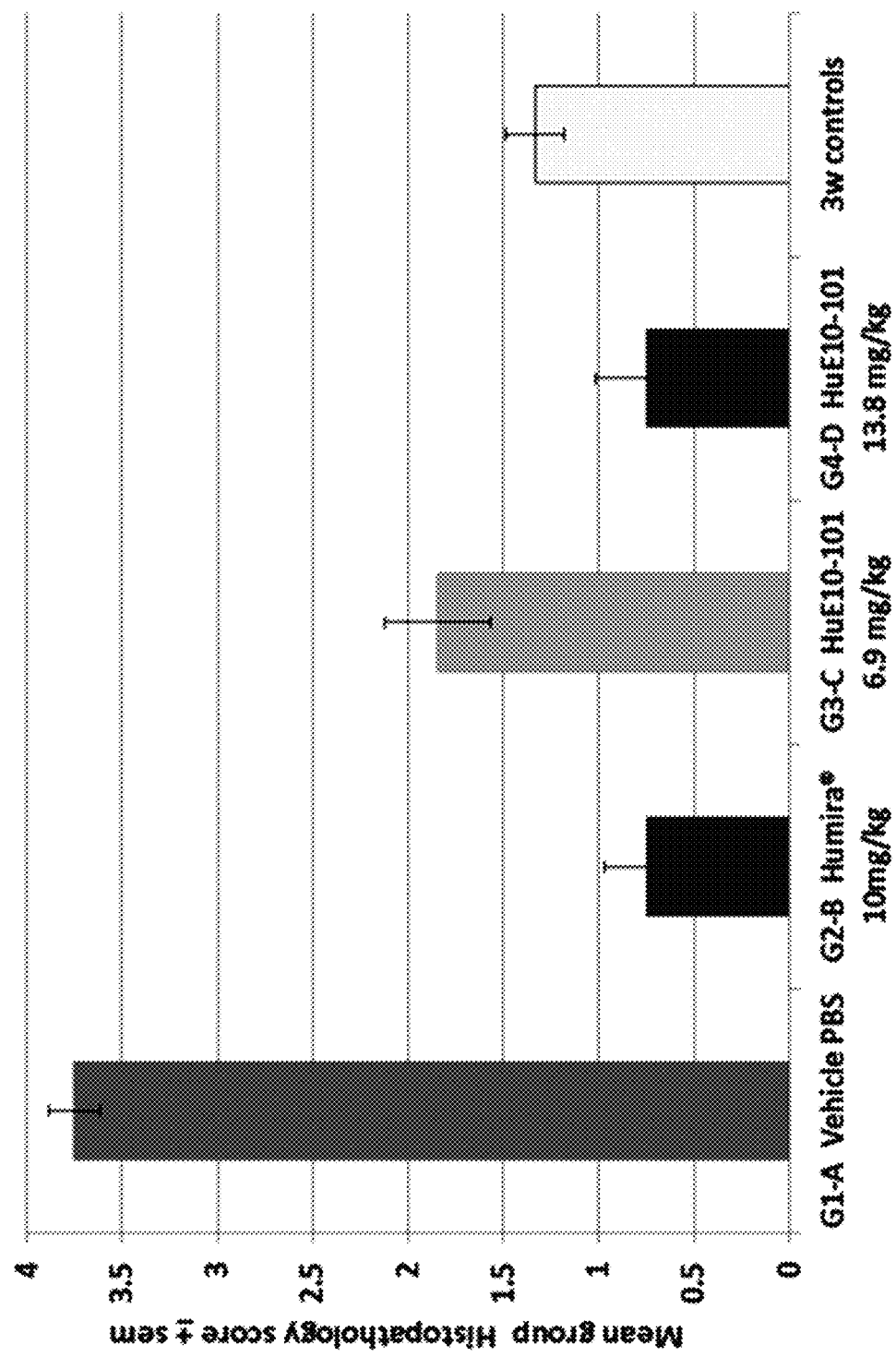
FIG. 37 shows histological scores determined after HuE10-101 is administered at different concentrations.

The histopathological score was 3.75 in the vehicle group, and 0.75 in the control group in which the concentration of Humira® was 10 mg/kg. In the experimental groups in which the concentrations of HuE10-101 were 6.9 and 13.8 mg/kg, the histopathological scores were 1.84 and 0.75, respectively. Before the drug was administered, the three-week-old mouse showed a histopathological score of 1.33. As a result of comparing the histopathological evaluation results between HuE10-101 and Humira®, it can be noted that they showed equivalent effects (FIG. 37).

Figure 38:
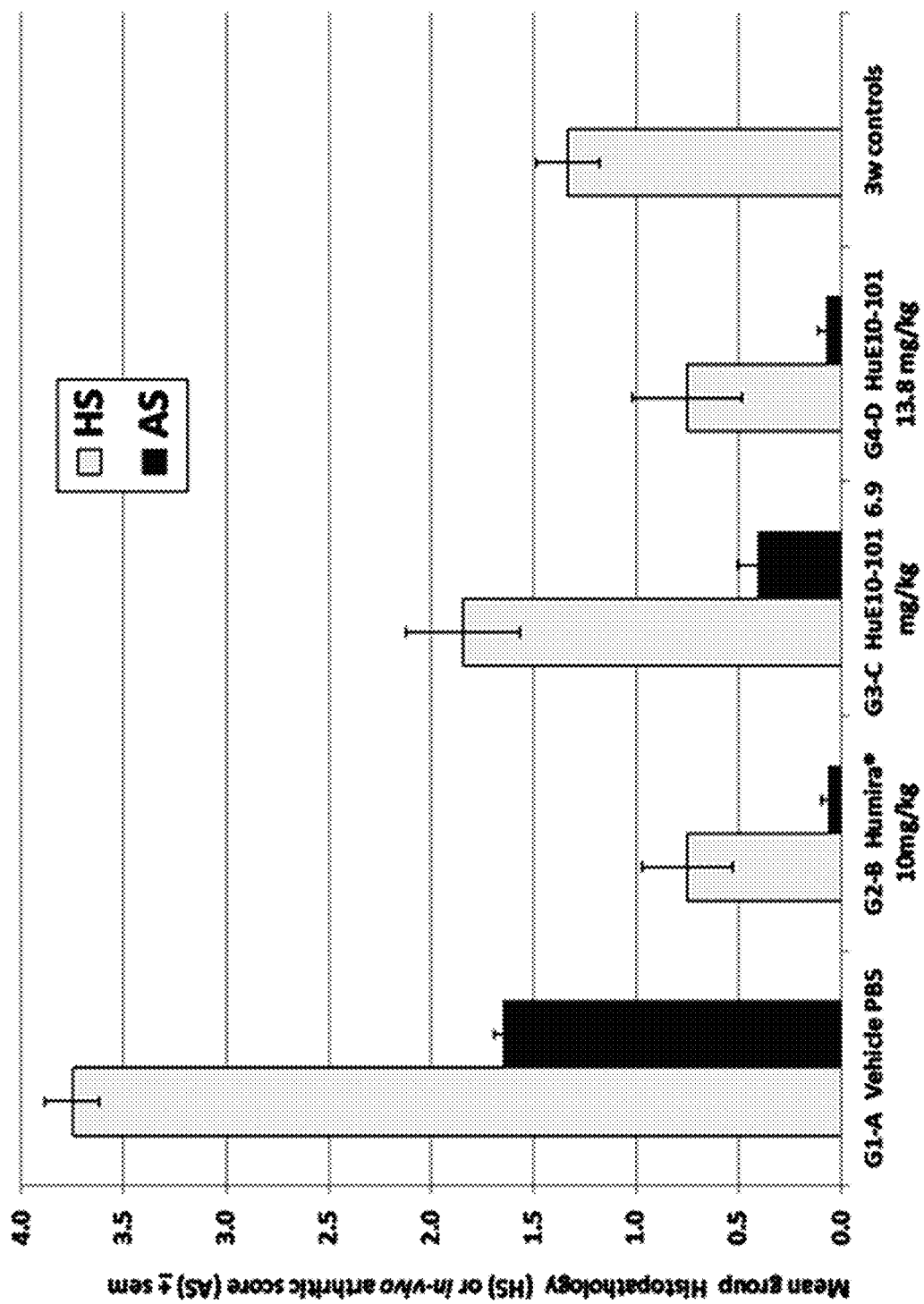
FIG. 38 are comparative results of the arthritis scores and the histological scores.

The histopathological evaluation results and the arthritis scores of HuE10-101 were compared and analyzed. The vehicle groups showed a histopathological evaluation value of 3.75 and an arthritis score of 1.65, the Humira® group showed a histopathological evaluation value of 0.75 and an arthritis score of 0.06, the group in which HuE10-101 was used as a treatment at a concentration of 6.9 mg/kg showed a histopathological evaluation value of 1.84 and an arthritis score of 0.41, and the group in which HuE10-101 was used as a treatment at a concentration of 13.8 mg/kg showed a histopathological evaluation value of 0.75 and an arthritis score of 0.07. Before the drugs were administered, the three-week-old mouse showed a histopathological evaluation value of 1.33 and an arthritis score of 0. When HuE10-101 and Humira® were used as therapeutic agents, according to the comparative results of the histopathological scores and the arthritis scores, it can be confirmed that the both drugs showed an equivalent therapeutic effect (FIG. 38).

According to the clinical evaluation for HuE10-101, compared to the control group Humira®, the arthritis score was not significantly reduced, but as the concentration of HuE10-101 increased, the arthritis score was reduced.

Also, according to the measurement of the change in body weight, it was shown that the body weight reduced as the lesion were developing increased as the concentration of the administered HuE10-101 increased, similar to the Humira® group.

9-1-4. Evaluation of Efficacy of Bispecific Antibody Produced in Production Cell Line Using Humanized TNF Transgenic Mouse To evaluate the efficacy of an antibody produced from a production cell line, efficacy evaluation using the TNF transgenic mouse model was further carried out.

Figure 39:
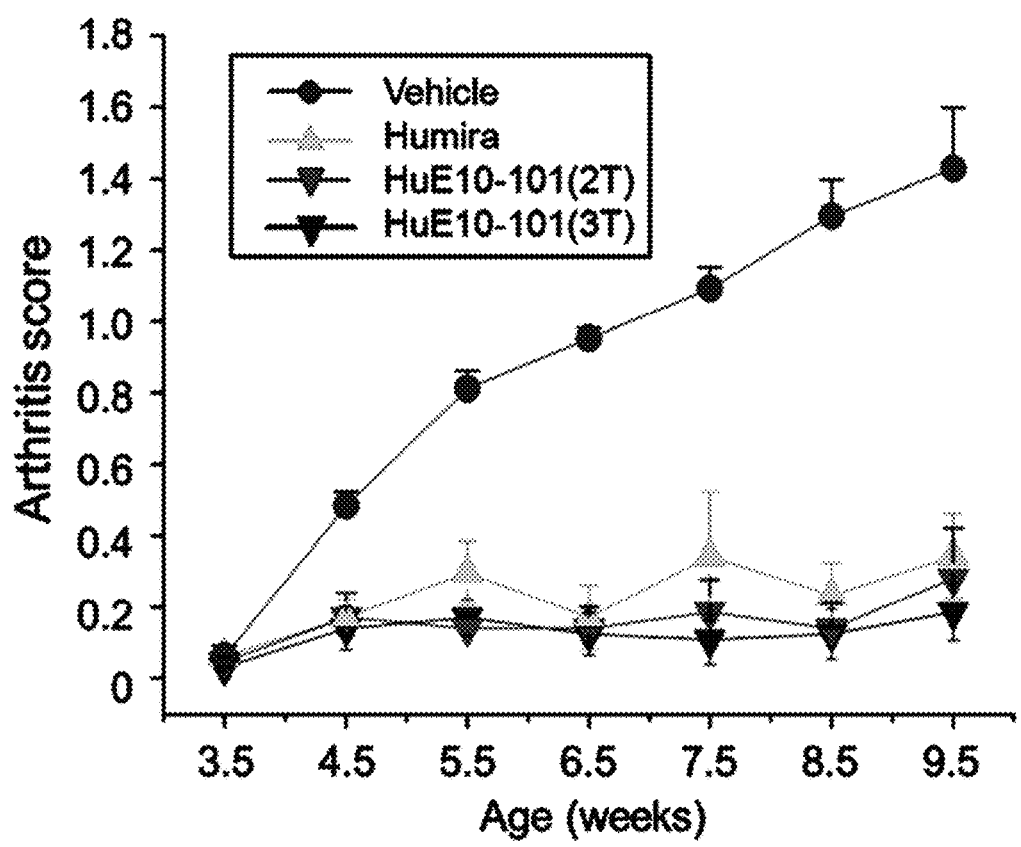
FIG. 39 shows arthritis scores determined after HuE10-101 produced in a production cell line is administered at different concentrations.

As a control group for the re-executed experiment condition, Humira® was used, and as experimental groups, HuE10-101 was administered at a concentration of 13.8 mg/kg twice and three times a week. Changes in body weight and arthritis scores were detected after 3.5 weeks to 9.5 weeks. As a result, the arthritis score was 1.43 in a vehicle group, 0.34 in the Humira® group, 0.28 in the group in which HuE10-101 was administered at the same intervals as Humira®, and 0.19 in the group in which HuE10-101 was administered three times a week (FIG. 39).

Figure 40:
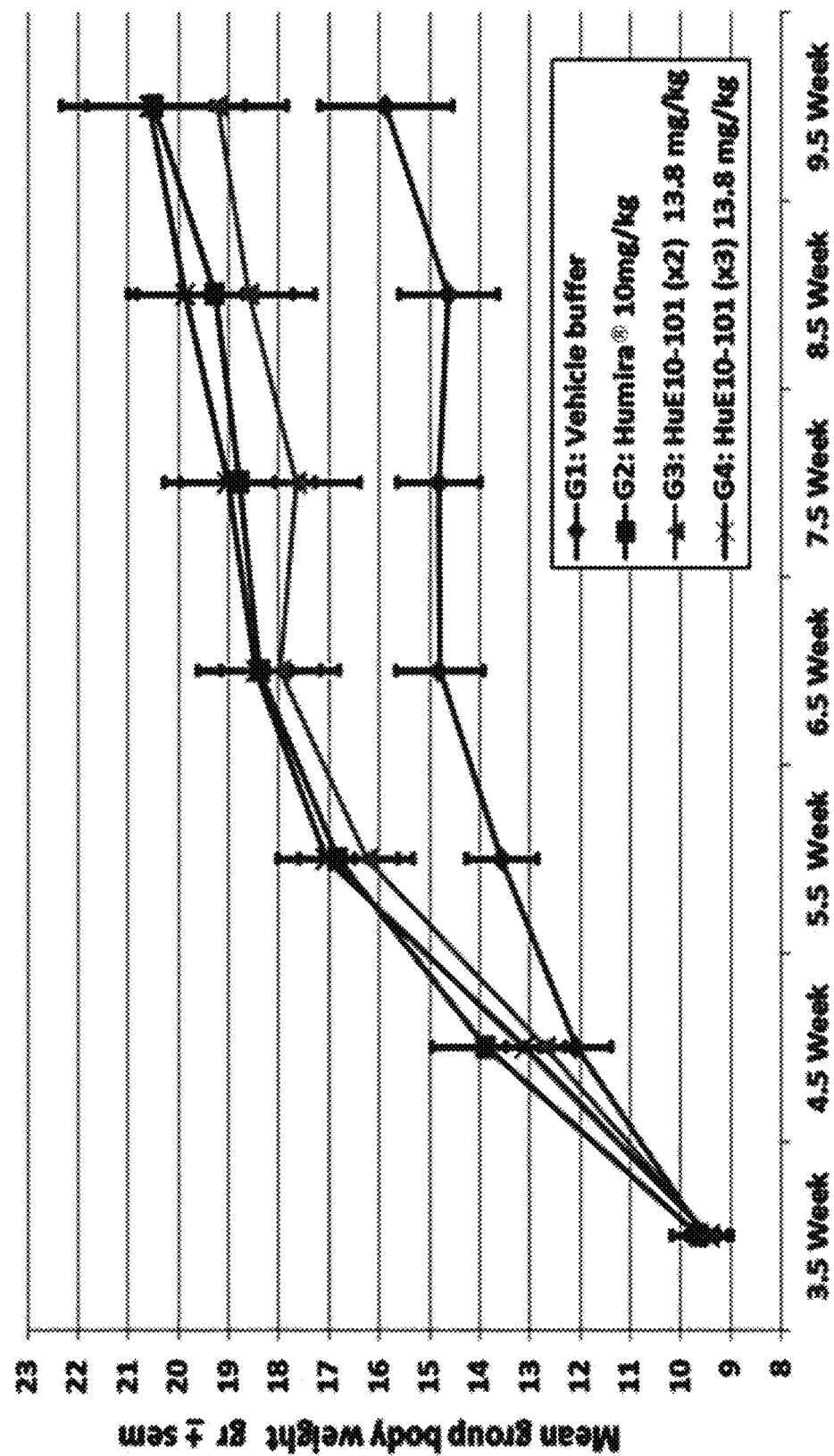
FIG. 40 shows body weight changes determined after the HuE10-101 produced in a production cell line is administered at different concentrations.

The measurement of the change in body weight was carried out at the same stage as the arthritis score measurement. As a result, the body weight was 15.87 g in the vehicle group, and 20.50 g in the Humira® group. The body weight was 19.21 g in the group in HuE10-101 was administered at the same intervals as Humira®, and 20.58 g in the group in which HuE10-101 was administered three times a week (FIG. 40).

Figure 42:
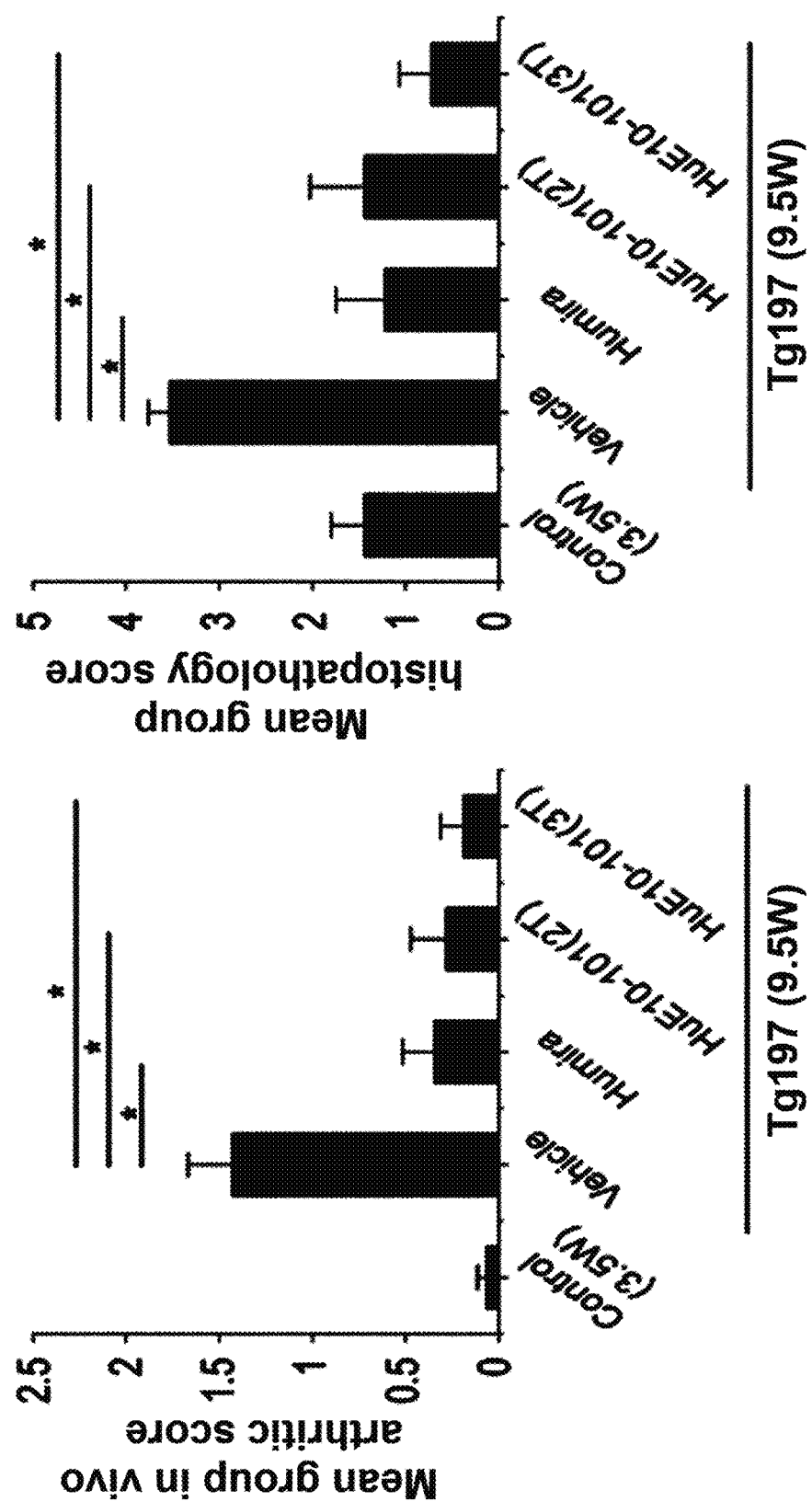
FIG. 42 shows histological scores determined after the HuE10-101 produced in a production cell line is administered at different concentrations.

Compared to the Humira® group, the arthritis scores were significantly reduced in the HuE10-101 groups, and the arthritis score was reduced as the concentration of HuE10-101 increased. According to the measurement in changes in body weight, it was shown that the body weight reduced as the lesion was developing increased as the concentration of HuE10-101 increased, similar to that in the Humira® group (FIG. 42).

Figure 41:
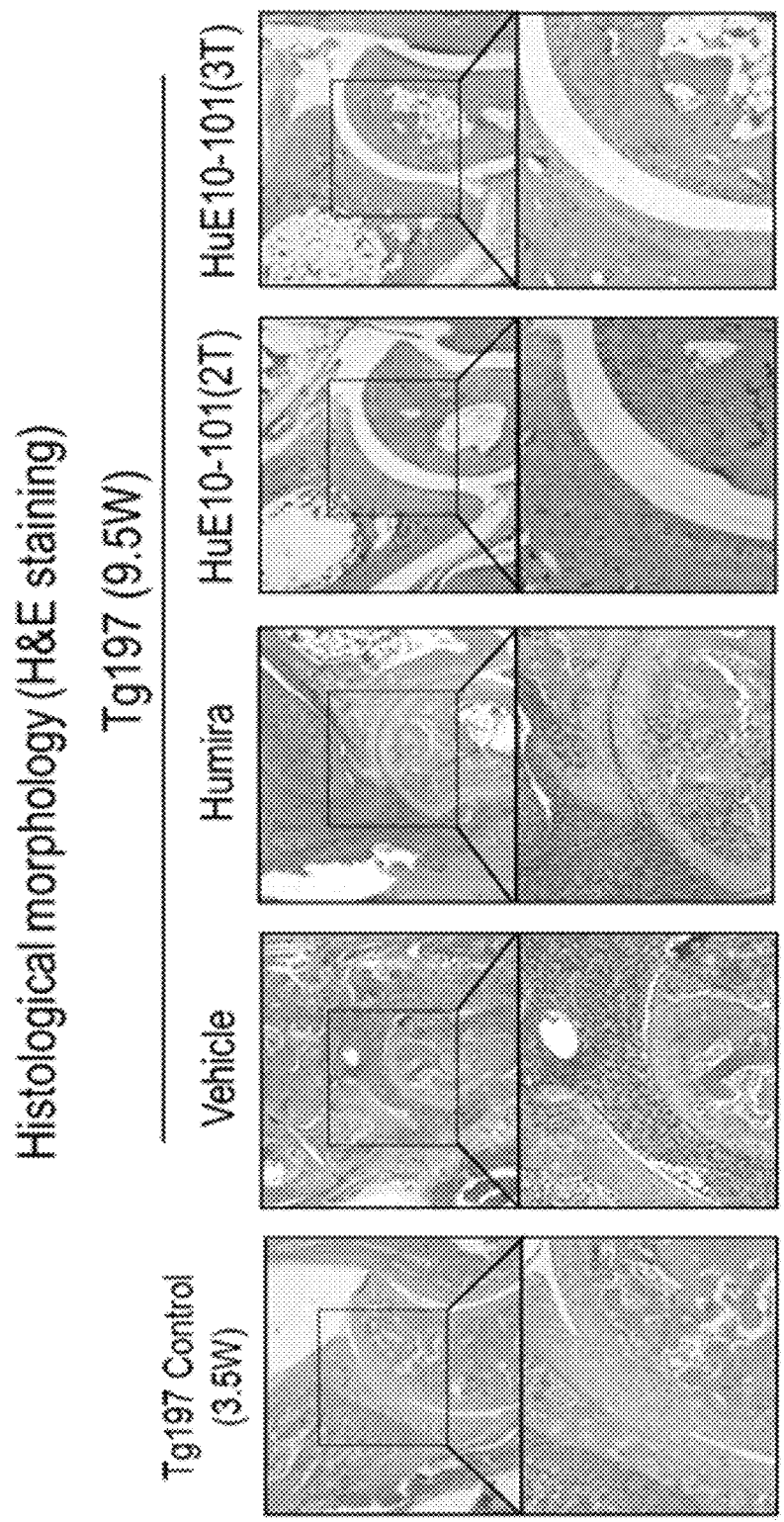
FIG. 41 shows pathological changes of Tg197 mouse tissues after an experiment is finished.

According to the histopathological evaluation for HuE10-101, the score was 3.53 in the vehicle group, and 1.22 in the Humira® group. The score was 1.44 in the group in HuE10-101 was administered at the same intervals as Humira® and 0.72 in the group in which HuE10-101 was administered three times a week. Before the drugs were administered, the 3.5-week-old mouse showed a histopathological score of 1.44. According to the comparative result of the histopathological evaluation between HuE10-101 and Humira®, it was confirmed that the histopathological score of the group in which HuE10-101 was administered three times a week was lower than that of Humira®, which indicates that HuE10-101 is more effective than Humira® (FIG. 41, 42).

Figure 43:
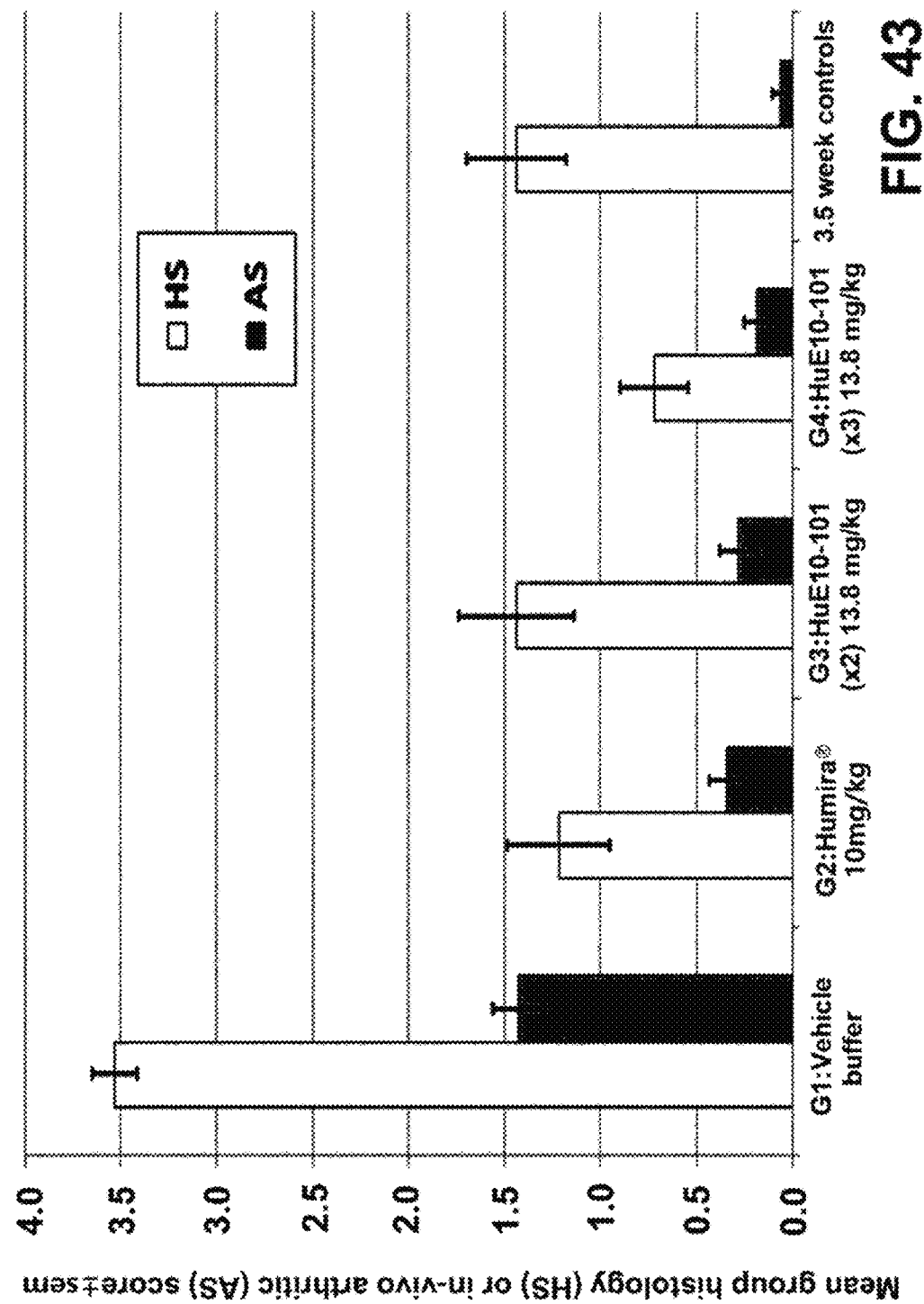
FIG. 43 shows comparative results of the arthritis scores and the histological scores of the HuE10-101 produced in production cell line.

The histopathological evaluation results and the arthritis scores of HuE10-101 were compared and analyzed. The vehicle group showed a histopathological evaluation value of 3.53 and an arthritis score of 1.435, the Humira® group showed a histopathological evaluation value of 1.22 and an arthritis score of 0.34, the group in HuE10-101 was administered at the same intervals as Humira® showed a histopathological evaluation value of 1.44 and an arthritis score of 0.28, and the group in which HuE10-101 was administered three times a week showed a histopathological evaluation value of 0.72 and an arthritis score of 0.19. Before the drugs were administered, the 3-week-old mouse showed a histopathological score of 1.44 and an arthritis score of 0.06 (FIG. 43).

When HuE10-101 and Humira® were used as therapeutic agents, according to the comparison of the histopathological evaluation values and the arthritis scores, of these two therapeutic agents, it was confirmed that the both drugs exhibited an equal or higher therapeutic effect.

Afterward, cytokine in a mouse serum was measured, and observation of pathological changes and statistical analysis for tissues obtained from the mouse proceeded.

9-2. Evaluation of Efficacy of Bispecific Antibody in Mouse Model Using K/B×N Serum 9-2-1. K/B×N Spontaneous Arthritis Animal Model (K/B×N Serum Transfer Arthritis model)

An arthritis (K/B×N serum transfer arthritis) mouse model, established by Benoist and Mathis, is a model obtained by crossing KRN TCR transgenic mice with a C57BL/6 background with non-obese diabetic (NOD) mice. A KRN TCR transgene pathogenesis is designed by altering antigen specificity to recognize glucose 6 phosphate isomerase (GPI) 282-294 as well as a ribonuclease, thereby allowing anti-GPI antibody produced by B cells to play a critical role in the occurrence of arthritis. This model was named K/B×N spontaneous arthritis because it spontaneously developed arthritis at the age of about 4 weeks, and symptoms of the arthritis are similar to those of rheumatoid arthritis.

According to the pathological observation of a joint in the K/B×N mouse, clinical features such as leukocyte infiltration, proliferation of synoviocytes, pannus formation, synovial inflammation and bone and cartilage damage, which appear in a patient with rheumatoid arthritis and a collagen-inducible arthritis model, were observed, and immunological features such as polyclonal activity of B cells, hypergammaglobulinemia and production of an autoantibody were shown. However, the K/B×N serum transfer arthritis is different from rheumatoid arthritis in that there is no rheumatoid factor recognized as an indicator for rheumatoid arthritis.

The inventors introduced the rheumatoid arthritis (K/B×N serum transfer arthritis) model based on the idea in that a serum obtained from K/B×N spontaneous arthritis mice is administered, thereby relatively easily triggering arthritis, and an experiment period is short, for example, within 2 weeks.

9-2-2. Results of Efficacy Evaluation Using K/B×N Spontaneous Arthritis Mouse Model The K/B×N spontaneous arthritis mice used in the experiment were 8-week-old or older, 150 μl of obtained serum was intraperitoneally administered into the 6-week-old or older mice each twice at day 0 and day 2, resulting in the induction of arthritis. At day 1 and day 3, HuE10-101 was administered.

Clinical evaluation was performed by evaluating an arthritis score and a rate of increase in edema. From the day after the final serum administering day of the K/B×N mouse, arthritis occurred, and the arthritis scores and the rates of increase in edema were overall at the maximum about 8 to 9 days after the final serum administering day and then gradually reduced.

Figure 44:
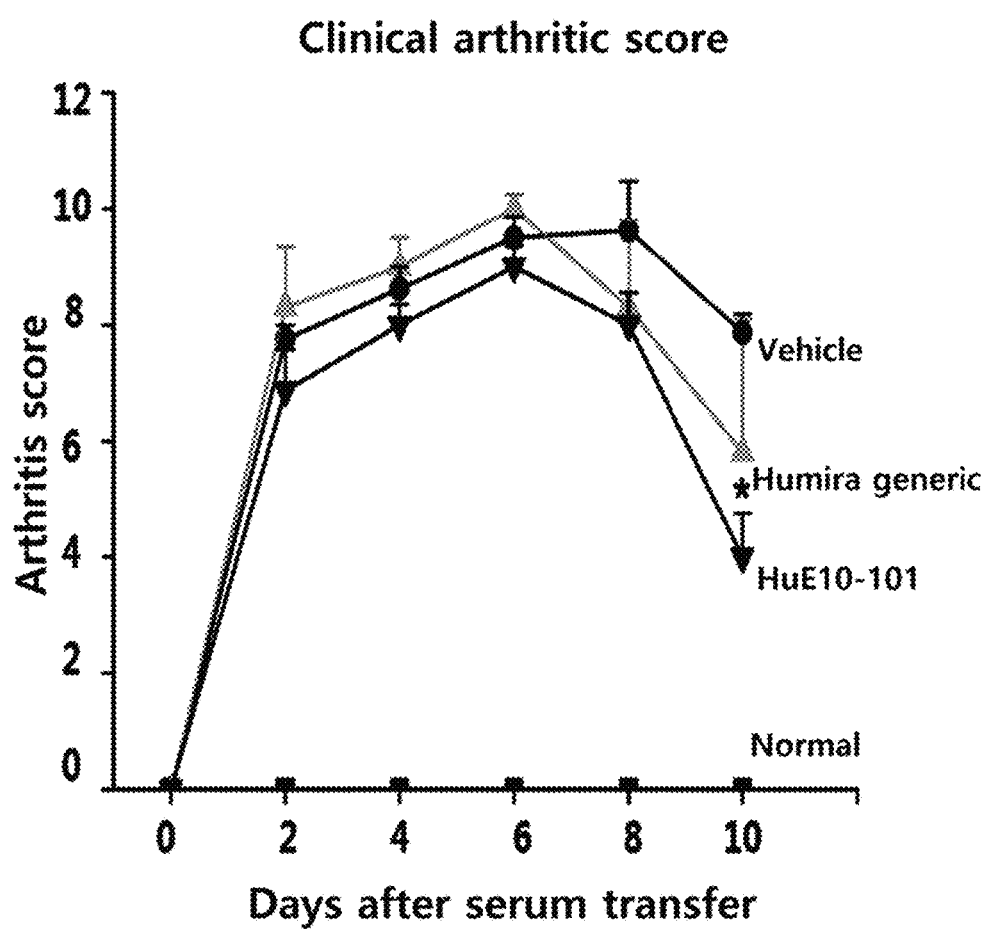
FIG. 44 shows arthritis scores of a K/BxN serum transfer arthritis mouse models.
Figure 45:
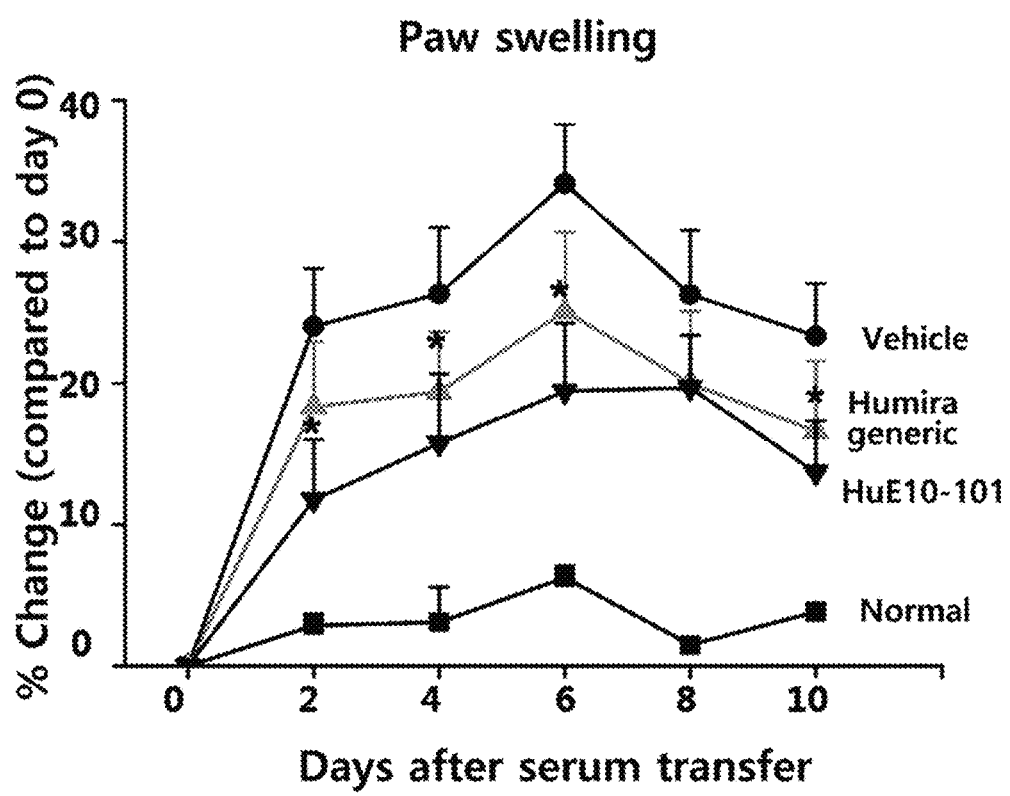
FIG. 45 shows edema changes of the K/BxN serum transfer arthritis mouse models.
Figure 46:
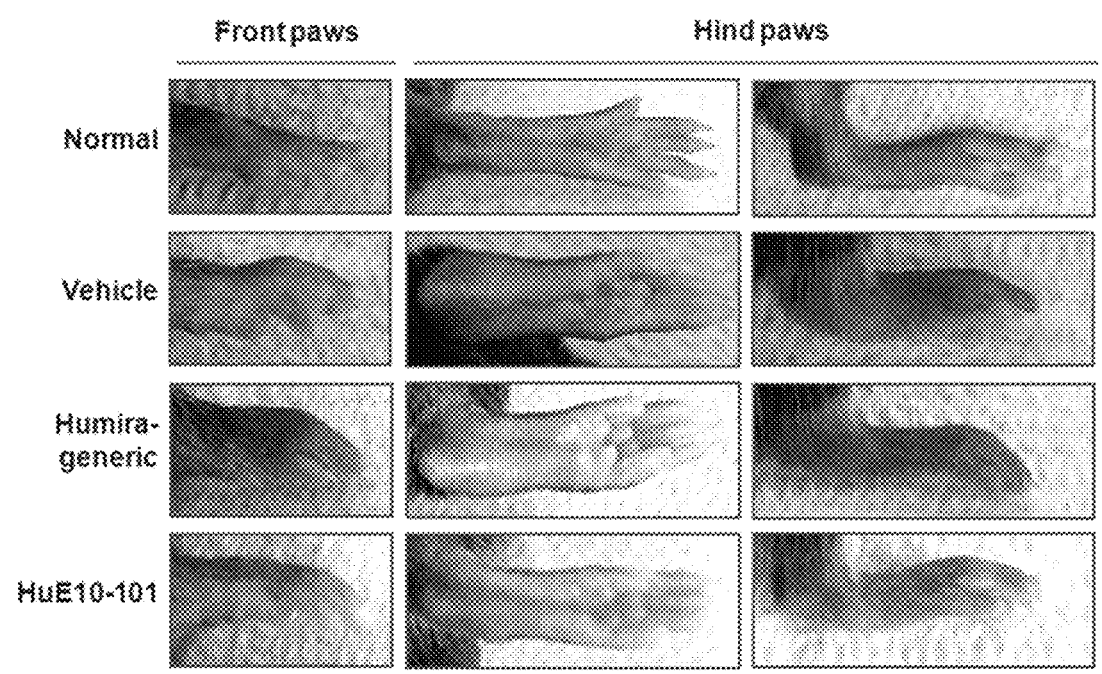
FIG. 46 shows edema changes of the K/BxN serum transfer arthritis mouse models.

According to the arthritis scores obtained from the arthritis mouse models, the arthritis score was 0 in a negative control, that is, a K/B×N serum-free group, 7.87 in a vehicle group, and 5.83 in a control group in which the concentration of Humira-generic antibody was 10 mg/kg. Also, in an experimental group in which the concentration of HuE10-101 was 10 mg/kg, the arthritis score was 4 (FIG. 44). According to the evaluation of the increase rate, the increase rate was 3.83 in the negative control, which is the K/B×N serum-free group, 23.34 in the vehicle group, and 16.58 in the control group in which the concentration of Humira-generic antibody was 10 mg/kg. In an experimental group in which the concentration of HuE10-101 was 10 mg/kg, the increase rate was 13.67 (FIG. 45). According to the clinical evaluation on HuE10-101 using the K/BxN serum transfer mouse model, the HuE10-101 group showed a lower arthritis score and edema increase rate than the control, which is Humira-generic antibody (FIG. 46).

Figure 47:
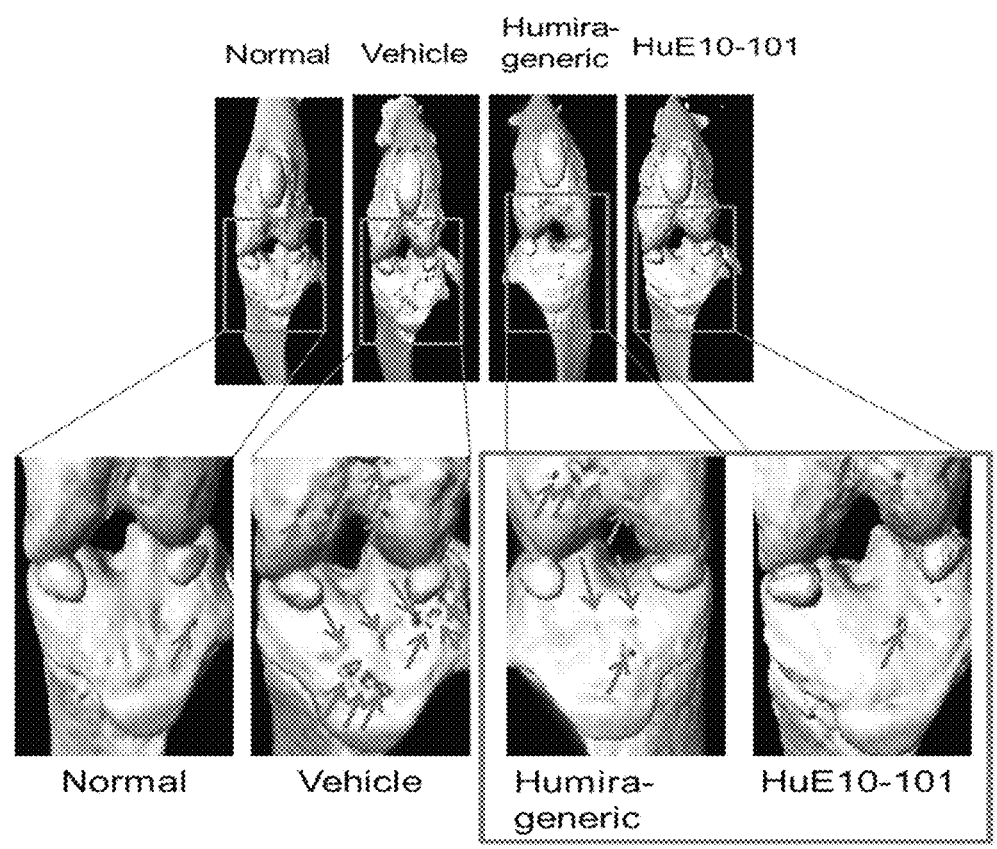
FIG. 47 shows bones of the K/BxN serum transfer arthritis mouse models, analyzed by micro CT.

Also, for analysis of the conditions of a bone joint of the K/BxN serum transfer arthritis mouse model after the experiment had been completed, joints in a hind leg of the mouse were analyzed with a micro CT (NanoFocusRay) instrument. As a result, it was seen that, in the arthritis-induced vehicle group, the morphology of a joint was irregularly changed, and bone damage was considerably advanced. Contrarily, it was confirmed that, in the Humira generic antibody-treated group as a control group and the experimental group, which is HuE10-101-treated group, bone damage was dramatically reduced, compared to the vehicle group. Particularly, in the experimental group, similar to the negative control, that is the K/BxN serum-free group, the bone damage was barely observed (FIG. 47).

Figure 48:
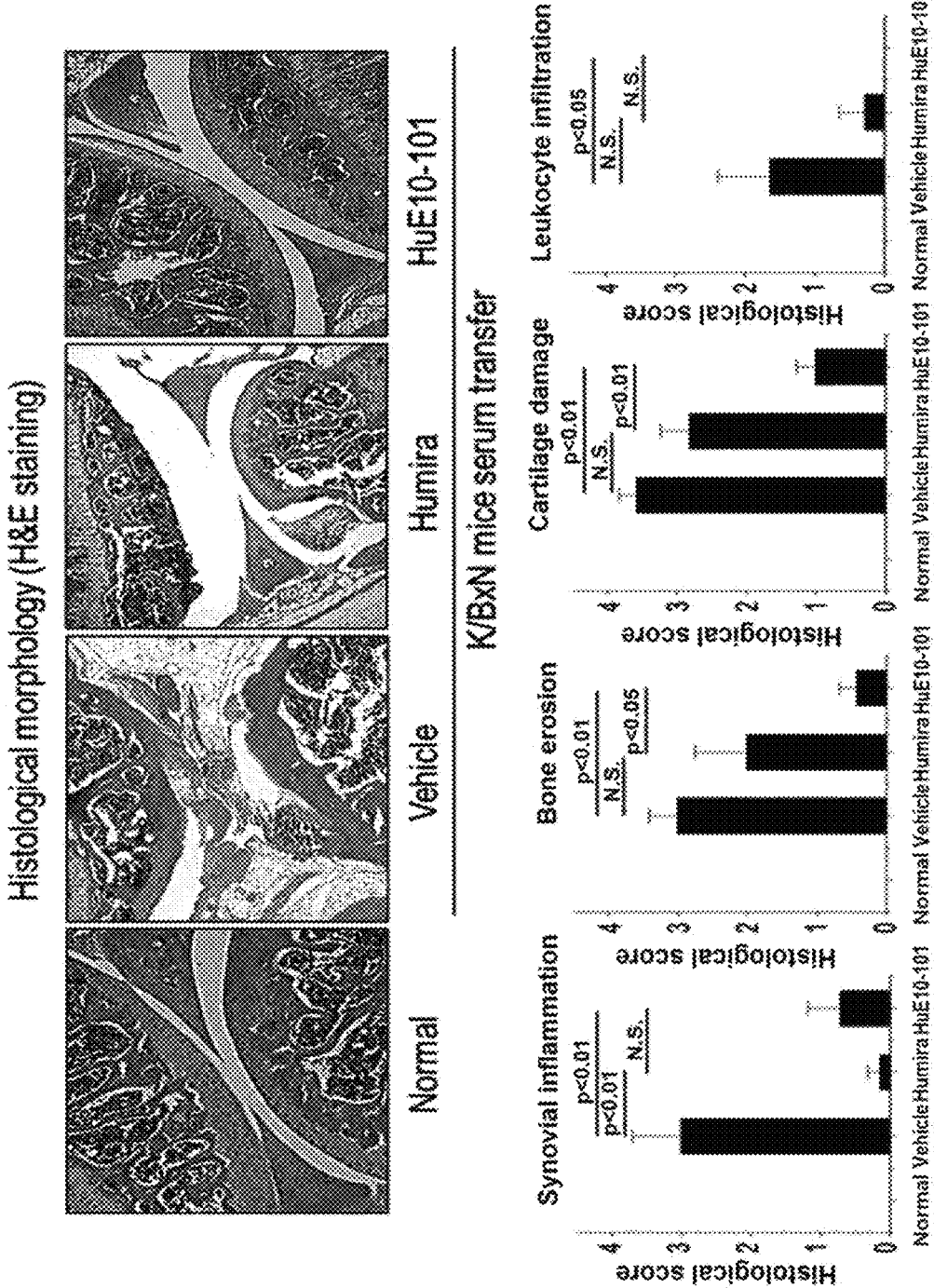
FIG. 48 shows histopathological lesions of the K/BxN serum transfer arthritis mouse models.

To check if the morphological changes were also observed in the histological changes, histological analysis was carried out with tissues obtained from the K/BxN serum transfer arthritis mouse model after the experiments had been completed. The tissues were stained with H&E to observe histological changes, and therefore, in the vehicle group, edema in the joint area, and polymorphonuclear leukocyte, lymphocyte infiltration were apparently shown, and synovial inflammation, thickening, cartilage loss on an articular surface were able to be observed. Contrarily, in the Humira-generic antibody-treated group and HuE10-101-treated group, an inflammatory response on the joint and cartilage damage were dramatically inhibited. By analysis of H&E-stained images, synovial inflammation, bone erosion, cartilage damage, and leukocyte infiltration were analyzed. As a result, the four features of synovial inflammation, bone erosion, cartilage damage and leukocyte infiltration were all reduced in the Humira-generic antibody-treated group and HuE10-101-treated group, compared to the vehicle group, and compared to the control, which is the Humira-treated group, the HuE10-101-treated group showed statistically significant reduction in those features (FIG. 48).

9-3. Evaluation of Efficacy of Bispecific Antibody Using LPS-Induced Inflammatory Bone Loss Mouse Model 9-3-1. LPS-Induced Calvarial Resorption An LPS-induced inflammatory bone loss mouse model is an animal model established by Nishihara et al. in 1995, and used to induce inflammatory bone loss using a pathogenic factor of inflammatory bone damage, such as a lipopolysaccharide (LPS).

The mechanism of increasing bone loss by LPS has not been determined in detail, but it is reported that LPS activates myeloid differentiation protein88 (MyD88) by Toll-Like Receptor4 (TLR4) in osteoblasts, stimulates secretion of signaling materials involved in bone resorption, such as interleukin-1 (IL-1), IL-6, granulocyte macrophage colony stimulating factor (GM-CSF), prostaglandin E2 (PGE2), and nitric oxide (NO), thereby stimulating the expression of RANKL in the osteoblasts, and thus induces differentiation of osteoclasts.

Figure 49:
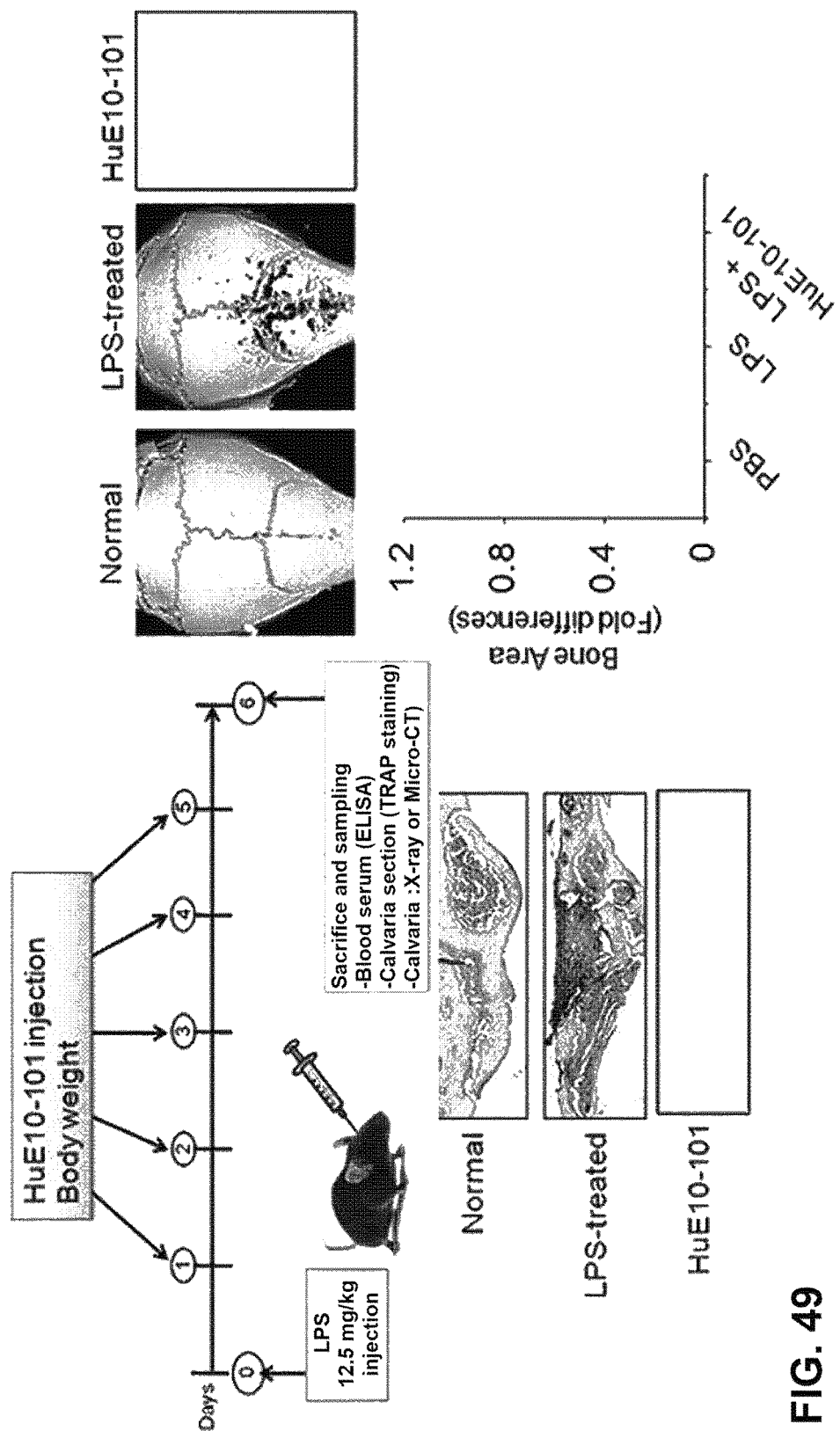
FIG. 49 is a schematic diagram showing evaluation of osteoclast differentiation capacity of HuE10-101 in an LPS-induced inflammatory bone loss mouse model.
Figure 50:
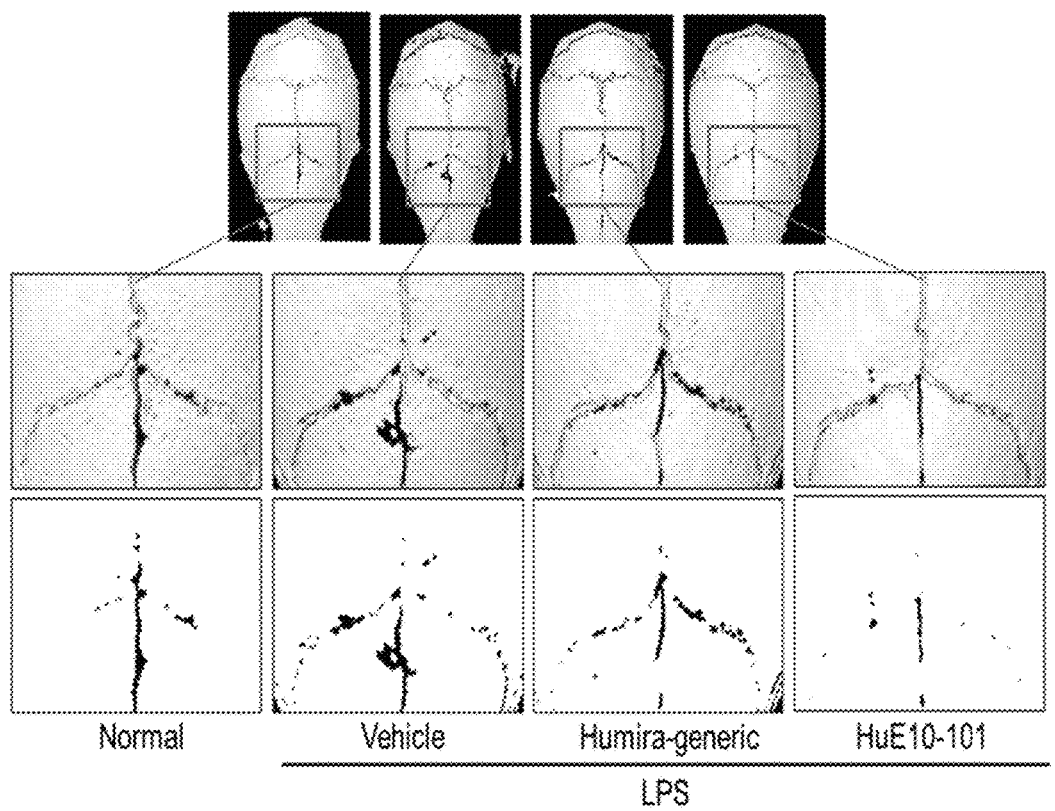
FIG. 50 shows evaluation results on the osteoclast differentiation capacity of HuE10-101 in the LPS-induced inflammatory bone loss mouse model.

The great advantage of the LPS-induced inflammatory bone loss mouse model is, like the arthritis mouse model (K/BxN serum transfer arthritis model), a model is constructed within a relatively short period. The LPS-induced inflammatory bone loss mouse model induces inflammation by single administration of LPS into a mouse skull. Then, every day for 5 days, HuE10-101 was administered into the skull (FIG. 49). LPS-induced inflammatory bone loss was identified by calvarial analysis through micro CT. As a result, in a vehicle group in which bone loss was induced by administration of LPS, a Humira-generic antibody-treated group as a control, a HuE10-101-treated group as an experimental group, and an LPS-free group as a negative control (normal), calvarial bone loss was observed. As a result, it was confirmed that, in the vehicle group, calvarial bone loss was significantly shown. Also, it was confirmed that, in the Humira-generic antibody-treated group and the experimental group, that is, the HuE10-101-treated group, the calvarial bone loss was significantly reduced, compared to the vehicle group. Consequently, it can be confirmed by evaluating in vivo osteoclast differentiation potential of HuE10-101 using the LPS-induced inflammatory bone loss mouse model that HuE10-101 more effectively inhibited osteoclast differentiation than Humira (FIG. 50).

To evaluate the efficacy of an antibody produced from a production cell line, the efficacy evaluation using the LPS-induced inflammatory bone loss mouse model was further carried out.

Figure 51:
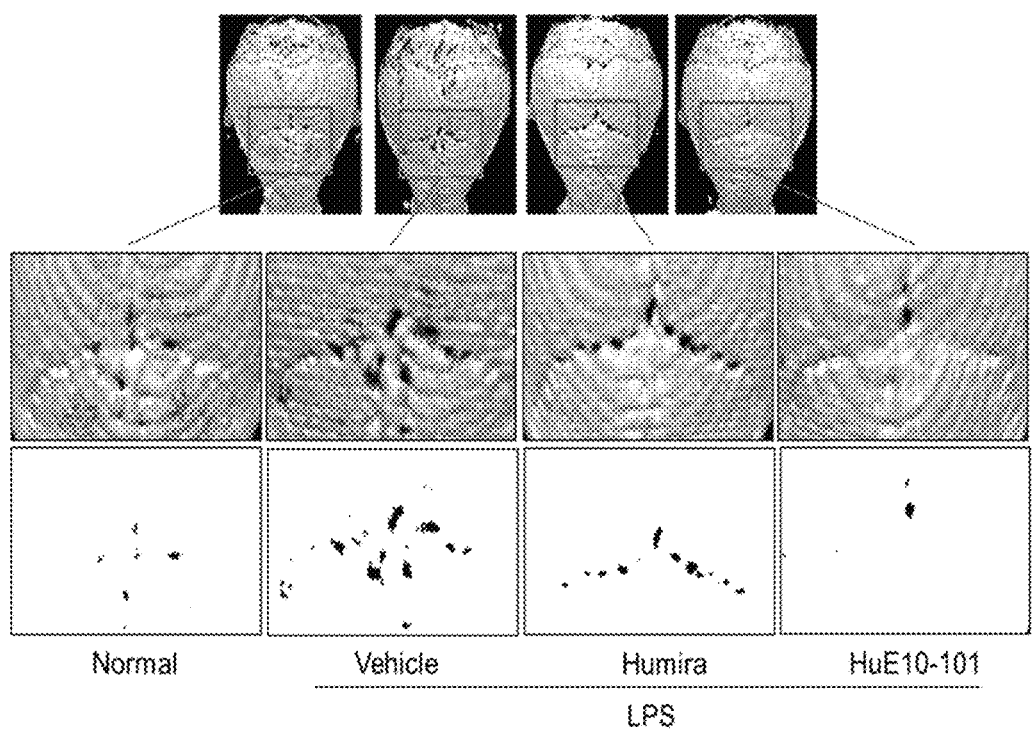
FIG. 51 shows evaluation results on the osteoclast differentiation capacity of HuE10-101 produced in a production cell line of the LPS-induced inflammatory bone loss mouse model.

As a result, a degree of calvarial bone loss was observed in the vehicle group in which bone loss was induced with LPS and only an antibody composition buffer was added, the Humira®-treated group as a control group, the HuE10-101-treate group, and the LPS-free group as a negative control (normal). Consequently, it was confirmed that the calvarial bone loss increased in the vehicle group. It was confirmed that, in Humira®-treated group and the HuE10-101-treate group, compared to the vehicle group, the calvarial bone loss was significantly reduced (FIG. 51).

Figure 52:
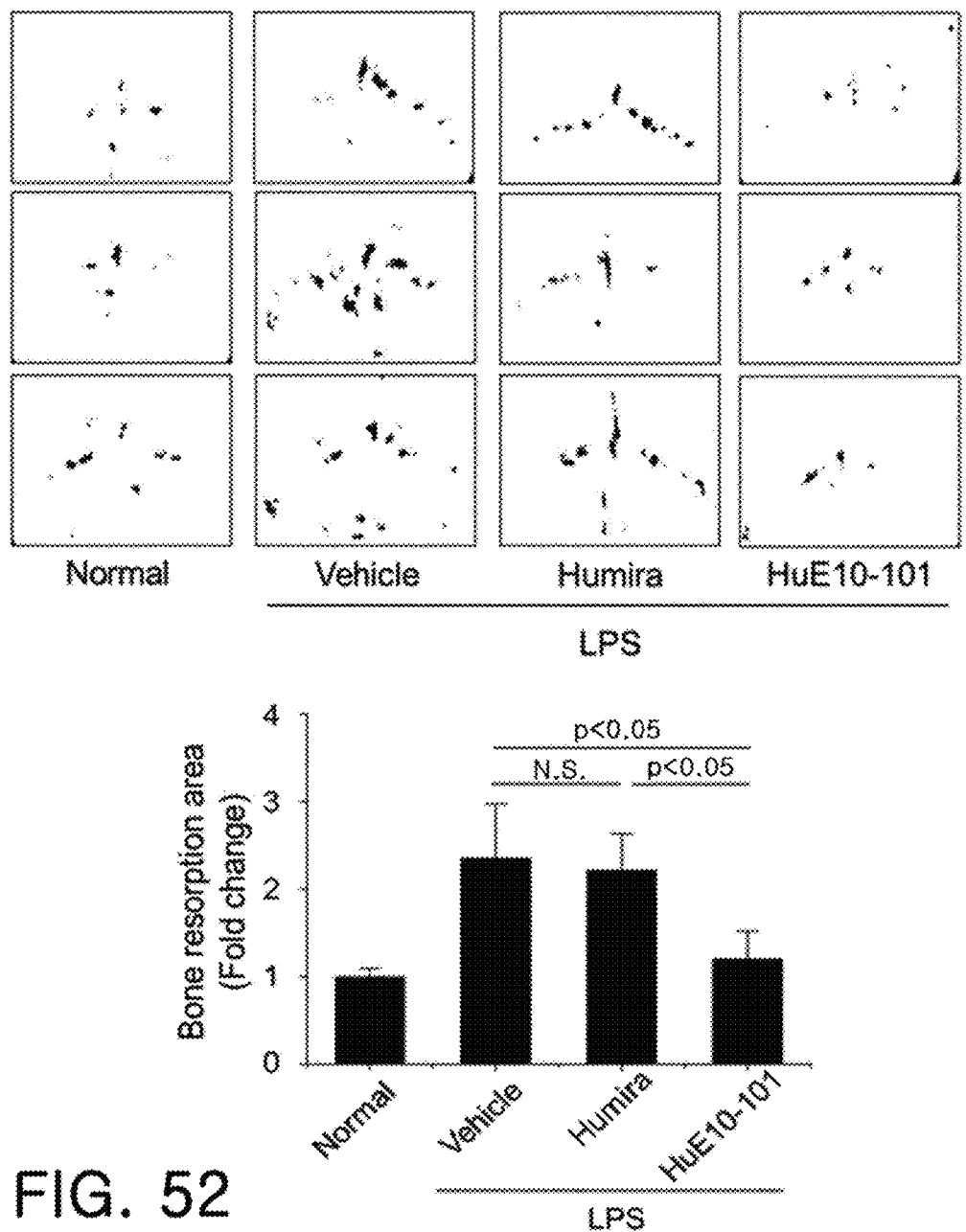
FIG. 52 shows quantitative analysis results for the osteoclast differentiation capacity of HuE10-101 produced in a production cell line in the LPS-induced inflammatory bone loss mouse model.

For closer analysis of the calvarial bone loss, a bone loss area was measured by an image analysis program (Image J). As a result, compared to the negative control, in the vehicle group, the bone loss was increased about 2.35 times, and in the Humira®-treated group, compared to the negative control, the bone loss was increased about 2.15 times, and compared to the vehicle group, increased 0.9 times. In the HuE10-101 group, compared to the negative control, the bone loss was increased about 1.2 times (P value: 0.0428), and compared to the vehicle group, the bone loss was increased 0.5 times, which indicates that the bone loss was reduced by about 48.79% (FIG. 52).

As the result of evaluating in vivo osteoclast differentiation potential of HuE10-101 produced from a production cell line using the LPS-induced inflammatory bone loss mouse model, like the result of the previous study, it was confirmed that HuE10-101 more effectively inhibited osteoclast differentiation than Humira®.

9-5. Evaluation of Efficacy of Bispecific Antibody in Collagen Inducible Arthritis Mouse MODEL A collagen inducible arthritis model created by Trentham in 1977 is a representative autoimmune arthritis model of rheumatoid arthritis, which is the most commonly used. This model was created based on the idea in which an antibody against collagen was found in serum of a patient with rheumatoid arthritis, and type collagen present at a joint was able to serve as an autoantigen.

A characteristic of the collagen inducible arthritis mouse model is that the collagen inducible arthritis mouse model has similar clinical features to human rheumatoid arthritis. The similar clinical features are relevance with a Class II MHC haplotype, pathogenesis reflecting adaptive immunity caused by T and B cell responses specific to autoantigens, involvement of an autoantibody and a complement system in joint tissue damage, proliferation of synoviocytes, lymphocyte infiltration, and pannus formation.

The inventors have confirmed in the previous study that CXCL10 increases in the animal model of rheumatoid arthritis, that is, the collagen inducible arthritis model. Also, through the experiment for inhibiting symptoms of collagen inducible arthritis by a CXCL10 inhibiting antibody, they determined that CXCL10 is associated with bone resorption by rheumatoid arthritis and an osteoclast differentiation stimulating factor.

Figure 53:
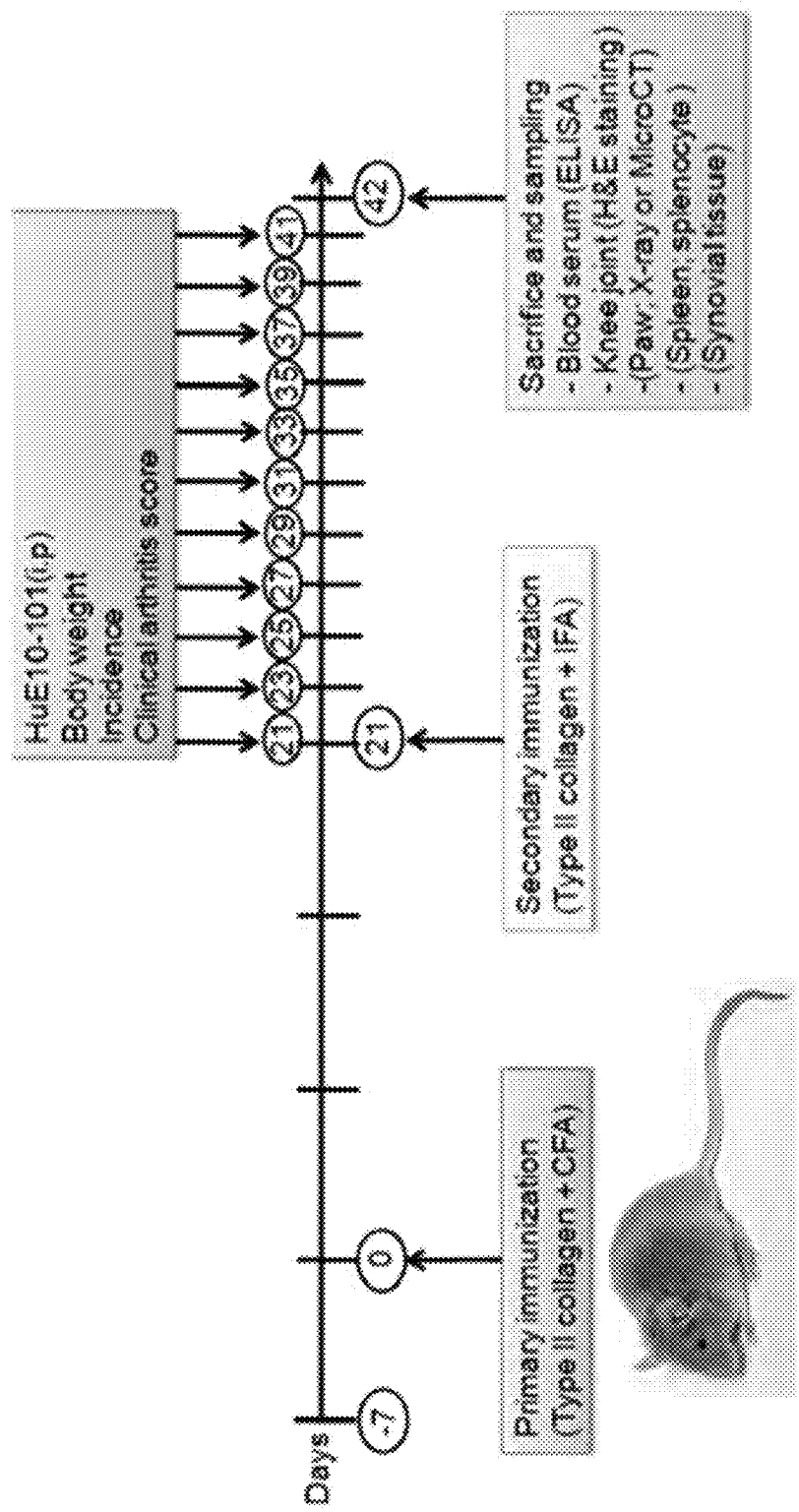
FIG. 53 is a schematic diagram for evaluating the efficacy of HuE10-101 in a collagen-inducible arthritis mouse model.

In the collagen inducible arthritis mouse model, bovine-type collagen (2, 4 mg/mL) was dissolved in acetic acid (0.05-0.1 M) at 4° C., and suspended with an equal amount of Freund's adjuvant. 0.1 mL of the suspension was subcutaneously injected into a base of the tail of male DBA/1J mice (5 to 9-week-old) (first injection), and three weeks later, the suspension (0.1 to 0.2 ml) was additionally subcutaneously injected into the base of the tail (booster or second injection) (FIG. 53).

Clinical evaluation on the collagen inducible arthritis mouse model was evaluated by arthritis scores with the same criteria as the efficacy evaluation using the TNF transgenic mouse model, and will be evaluated in combination with a pathological test and immunostaining, measurement of inflammatory cytokines.

Example 10: Cross Reactivity Test for Antibodies

In the case of an antibody medicine, when identical or related antigen determining regions were expressed in human cells or tissues, other than target cells, an antibody may also bind to a tissue.

Figure 54:
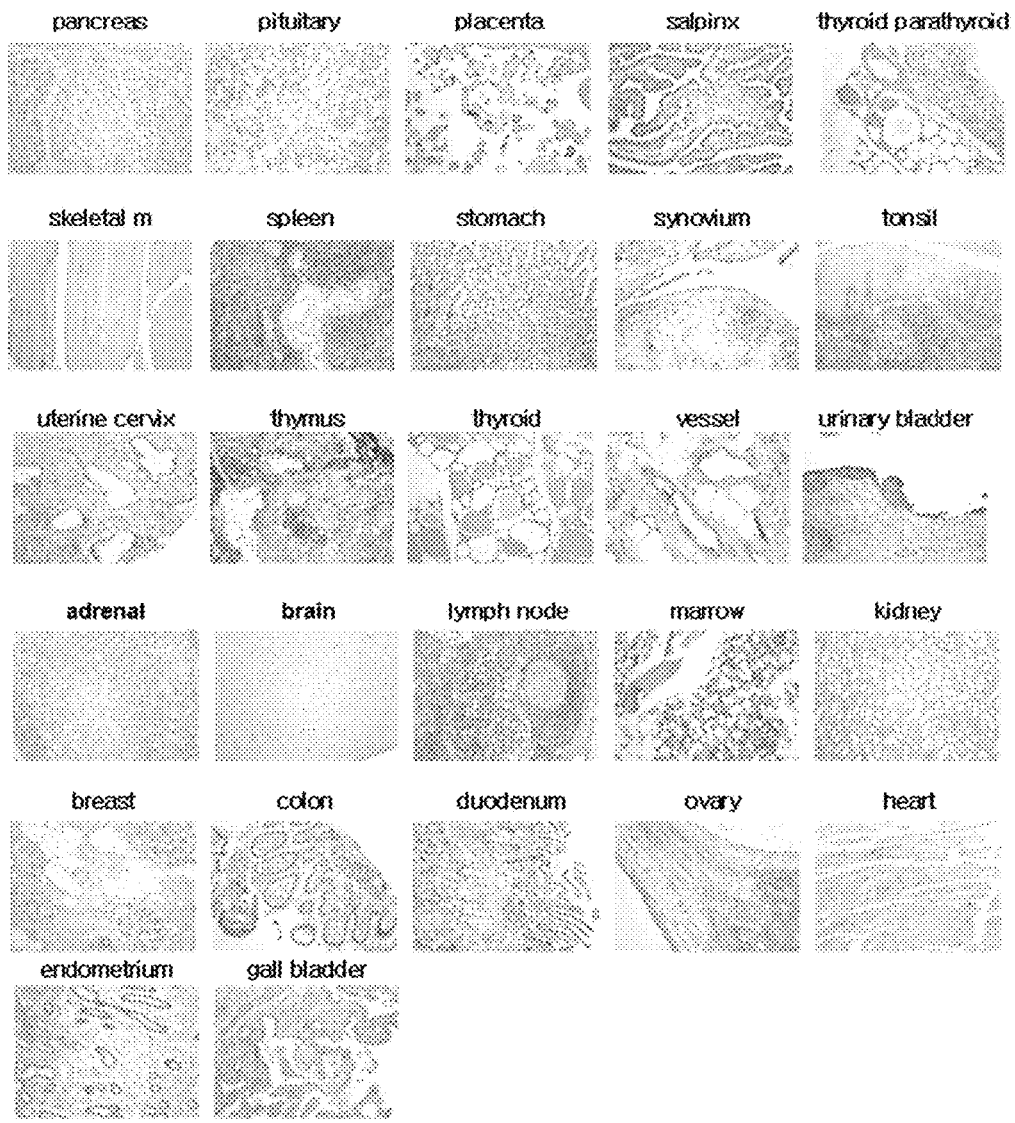
FIG. 54 is a result of a cross-reaction of HuE10-101 using 32 unduplicated types of tissue from three people.

To determine cross reactivity or binding to a non-specific tissue, a cross reactivity study for human tissues has to be always performed in a non-clinical stage. A cross reactivity test was carried out with reference to the guideline on tissue cross reactivity testing (KFDA, 2013) specified in the guide on evaluation for monoclonal antibody medicine. For immunohistochemical staining, an EnVision Detection System was used, and a cross reaction was identified using 32 unduplicated types of tissue obtained from three people. As a result, it was confirmed that HuE10-101 does not non-specifically bind to other tissues (FIG. 54).

As described above, the exemplary embodiments of the present invention have been described in detail. Therefore, it will be clearly understood by those of ordinary skill in the art that the detailed descriptions are merely exemplary embodiments, and the scope of the present invention is not limited thereto. Accordingly, the actual range of the present invention will be defined by the accompanying claims and equivalents thereof.

---

The invention claimed is:

1. A TNF-α/CXCL-10 double-targeting antibody, comprising:
 a first antigen-binding site specifically binding to tumor necrosis factor-alpha (TNF-α); and
 a second antigen-binding site specifically binding to C—X-C motif chemokine 10 (CXCL10),
wherein
 the first antigen-binding site comprises a heavy chain variable domain (VH) including a heavy chain complementarity determining region (HCDR) 1 having the amino acids of SEQ ID NO: 1, an HCDR2 having the amino acids of SEQ ID NO: 2, and an HCDR3 having the amino acids of SEQ ID NO: 3, and a light chain variable domain (VL) including a light chain complementarity determining region (LCDR) 1 having the amino acids of SEQ ID NO: 5, an LCDR2 having the amino acids of SEQ ID NO: 6, and an LCDR3 having the amino acids of SEQ ID NO: 7, and the second antigen-binding site comprises a heavy chain variable domain (VH) including an HCDR1 having the amino acids of SEQ ID NO: 9, an HCDR2 having the amino acids of SEQ ID NO: 10, and an HCDR3 having the amino acids of SEQ ID NO: 11, and a light chain variable domain (VL) including an LCDR1 having the amino acids of SEQ ID NOs: 13, an LCDR2 having the amino acids of SEQ ID NO: 14, and an LCDR3 having the amino acids of SEQ ID NO: 15.

2. The antibody of claim 1, wherein the first antigen binding site comprises the heavy chain variable domain (VH) having the amino acids of SEQ ID NO: 4.

3. The antibody of claim 1, wherein the first antigen binding site comprises the light chain variable domain (VL) having the amino acids of SEQ ID NO: 8.

4. The antibody of claim 1, wherein the second antigen-binding site comprises the heavy chain variable domain (VH) having the amino acids of SEQ ID NO: 12.

5. The antibody of claim 1, wherein the second antigen-binding site comprises the light chain variable domain (VL) having the amino acids of SEQ ID NO: 16.

6. The antibody of claim 1, wherein the first antigen binding site comprises a full-length antibody and the second antigen binding site comprises a fragment of full-length antibody and wherein the fragment of full-length antibody comprises a heavy chain variable domain and a light chain variable domain and wherein the fragment of full-length antibody of the second antigen binding site is linked to a C-terminus of a heavy chain constant domain of the first antigen binding site.

7. The antibody of claim 6, wherein the fragment of full-length antibody of the second antigen binding site is a single-chain variable fragment (scFv).

8. The antibody of claim 6, wherein the linkage of the full-length antibody of the first antigen binding site and the fragment of full-length antibody of the second antigen binding site is made by a linker.

9. A transformant cotransfected with an expression vector, wherein said expression vector comprises:
(i) a first polynucleotide encoding a first antigen binding site comprising:
   (a) a first heavy chain variable domain comprising a heavy chain complementarity determining region (HCDR) 1 having the amino acids of SEQ ID NO: 1, an HCDR2 having the amino acids of SEQ ID NO: 2, and an HCDR3 having the amino acids of SEQ ID NO: 3,
   (b) a first light chain variable domain (VL), wherein said light chain variable domain comprises a light chain complementarity determining region (LCDR) 1 having the amino acids of SEQ ID NO: 5, an LCDR2 having the amino acids of SEQ ID NO: 6, and an LCDR3 having the amino acids of SEQ ID NO: 7, and
(ii) a second polynucleotide encoding a second antigen binding site comprising:
   (a) a second heavy chain variable domain (VH) comprising: an HCDR1 having the amino acids of SEQ ID NO: 9, an HCDR2 having the amino acids of SEQ ID NO: 10, and an HCDR3 having the amino acids of SEQ ID NO: 11, and
   (b) a second light chain variable domain (VL) comprising an LCDR1 having the amino acids of SEQ ID NOs: 13, an LCDR2 having the amino acids of SEQ ID NO: 14, and an LCDR3 having the amino acids of SEQ ID NO: 15.

10. A method of producing a TNF-α/CXCL10 double targeting antibody, comprising the steps of:
(a) culturing a transformant of claim 9 to produce a TNF-α/CXCL-10 double-targeting antibody; and
(b) isolating said TNF-α/CXCL-10 double-targeting antibody from a cell culture obtained in the step (a).

11. A method of inhibiting TNF-α or CXCL-10 in a subject in need thereof, said method comprising administering to said subject an effective amount of a composition comprising a TNF-α/CXCL-10 double targeting antibody of claim 1.

12. The method of claim 11, wherein said subject is suffering from an autoimmune disease or inflammatory disease.

13. A method of treating a subject having an autoimmune disease or inflammatory disease selected from the group consisting of rheumatoid arthritis, inflammatory bowel disease, psoriasis, asthma, atopic dermatitis, allergic rhinitis, chronic obstructive pulmonary disease and eczema, said method comprising administering to said subject a therapeutically effective amount of a composition comprising a TNF-α/CXCL-10 double targeting antibody of claim 1.

* * * * *